(12) United States Patent
Miyazaki et al.

(10) Patent No.: US 6,800,644 B2
(45) Date of Patent: Oct. 5, 2004

(54) NITROGEN-CONTAINING HETEROCYCLIC COMPOUNDS AND MEDICAMENTS CONTAINING THE COMPOUNDS

(75) Inventors: Kazuki Miyazaki, Ibaraki (JP); Yasutaka Takase, Brookline, MA (US); Takao Saeki, Ibaraki (JP)

(73) Assignee: Eisai Co., Ltd., Tokyo (JP)

(*) Notice: Subject to any disclaimer, the term of this patent is extended or adjusted under 35 U.S.C. 154(b) by 0 days.

(21) Appl. No.: 09/985,412

(22) Filed: Nov. 2, 2001

(65) Prior Publication Data

US 2002/0055516 A1 May 9, 2002

Related U.S. Application Data

(62) Division of application No. 09/600,995, filed as application No. PCT/JP99/00215 on Jan. 21, 1999, now Pat. No. 6,352,989.

(30) Foreign Application Priority Data

Jan. 26, 1998 (JP) .............................. 10-13062

(51) Int. Cl.$^7$ .................... A61K 31/47; A61K 31/44; C07D 215/38; C07D 217/00; C07D 471/00
(52) U.S. Cl. ................ 514/313; 514/310; 514/292; 514/290; 514/260; 514/259; 544/284; 544/291; 544/293; 546/159; 546/160; 546/143; 546/144; 546/81; 546/80
(58) Field of Search .................... 514/259, 260, 514/290, 292, 310, 313; 544/284, 291, 293; 546/159, 160, 143, 144, 81, 80

(56) References Cited

U.S. PATENT DOCUMENTS 6,596,735 B1 * 7/2003 Yang .................... 514/313

FOREIGN PATENT DOCUMENTS

| JP | B1-4020866 | 9/1965 |
| JP | A5888369 | 5/1983 |
| JP | A5-2299987 | 9/1993 |
| JP | A6192099 | 7/1994 |
| JP | 09059255 A | 3/1997 |
| WO | A1-9307124 | 4/1993 |

OTHER PUBLICATIONS

Radwan, A.M. et al., "A new route for the synthesis of 1,2,4–triazole and 3,4–disubstituted cinnoline derivatives", Chemical Abstract, 1995, vol. 124, Abstract #117193.*
Berkow R., Merck Manual, 16$^{th}$ Edition, (c) 1992, pp. 1488–1490.*
Giembycz, M. A. et al, Clinical and Experimental Allergy, 1992, vol. 22, pp. 337–344.
Semmler, J. et al, Int. J. Immunopharmac, vol. 15, No. 3, pp. 409–413, 1993.
Prabhakar, U. et al, Int. J. Immunopharmac, vol. 16, No. 10, pp. 805–816, 1994.
Abdel–Hadi et al., Pol. J. Pharmacol. Pharm., vol. 38, No. 1, pp. 99–106 (1992).

* cited by examiner

*Primary Examiner*—Richard L. Raymond
*Assistant Examiner*—Tamthom N. Truong
(74) *Attorney, Agent, or Firm*—Birch, Stewart, Kolasch & Birch, LLP

(57) ABSTRACT

The present invention provides a novel nitrogen-containing heterocyclic compound useful as a phosphodiesterase-4 inhibitor, and a medicament comprising the same. Further, the present invention provides a nitrogen-containing heterocyclic compound represented by the following formula, its salt or hydrates thereof, and a medicament comprising the same.

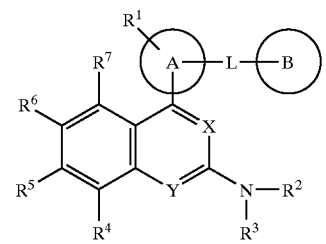

33 Claims, No Drawings

NITROGEN-CONTAINING HETEROCYCLIC COMPOUNDS AND MEDICAMENTS CONTAINING THE COMPOUNDS

This application is a divisional of application Ser. No. 09/600,995, filed on Jul. 26, 2000 now U.S. Pat. No. 6,352,989, and for which priority is claimed under 35 U.S.C. §120. Application Ser. No. 09/600,995 is the national phase of PCT International Application No. PCT/JP99/00215 filed on Jan. 21, 1999 under 35 U.S.C. §371. The entire contents of each of the above-identified applications are hereby incorporated by reference. This application also claims priority of application Ser. No. 10-13062 filed in Japan on Jan. 26, 1998 under 35 U.S.C. §119.

TECHNICAL FIELD

The present invention relates to a nitrogen-containing heterocyclic compound derivative useful as a phosphodiesterase-4 inhibitor, its salt or hydrates thereof, and a medicament comprising the same. More specifically, it relates to a prophylactic and therapeutic agent comprising a nitrogen-containing heterocyclic compound, its salt or hydrates thereof for inflammatory diseases, asthma, autoimmune disease such as allograft rejection, graft versus host disease, chronic joint rheumatism and multiple sclerosis, sepsis, psoriasis, osteoporosis or diabetes.

PRIOR ART

In a group of a series of decomposition enzymes called phosphodiesterase (referred to hereinafter as "PDE"), the presence of 7 families of PDE1 to PDE7 is confirmed. One family PDE4 is an enzyme specific to a secondary messenger, cyclic adenosine-3',5'-monophosphate (cyclic AMP), and is known to regulate the concentration of cyclic AMP by decomposition. Cyclic AMP is increased in vivo upon stimulation with hormone, to exhibit a wide variety of physiological actions such as formation of specific enzymes or regulation of metabolic functions, and in e.g. human leukocytes, cyclic AMP has an important role in activation of cells and regulation of immune response. Under this background, the physiological significance of PDE4 has been regarded as important in recent years, and it is expected that a PDE4 inhibitor can work effectively as a prophylactic and therapeutic agent against various diseases in which cyclic AMP is involved. For example, since PDE4 is present widely in mast cells eosinophils monocytes macrophages T-lymphocytes, epithelial cells, and respiratory smooth muscles, there have been proposed the possibility of the PDE4 inhibitor as an anti-asthma agent (Clin. Exp. Allergy, 22, 337–44, 1992) and the possibility of the PDE4 inhibitor as an agent for treating arthritis, cachexia, multiple sclerosis and sepsis on the basis of a report on the inhibition of tumor-necrosis-factor α (TNFα) by the PDE4 inhibitor (Int. J. Immunopharmacol., 15, 409–13, 1993; Int. J. Immunopharmacol., 16, 805–16, 1994). With these findings as the background, a large number of reports on those compounds inhibiting PDE4 have been made. For example, JP-A 5-229987 and JP-A 9-59255 disclose an invention relating to naphthalene compounds as PDE4 inhibitors. On the other hand, JP-B 40-20866 and JP-B 6-192099 disclose an invention relating to quinazoline compounds as inhibitors of production of TNFα.

Heretofore, theophylline is famous as a PDE4 inhibitor, but is poor in specificity for PDE4 and inhibits the PDE family unspecifically, thus bringing about side effects in cardiac blood vessels or in the central system. Further, other PDE4 inhibitors also cause the problems of nausea, emesis, headache etc., and therefore, none of effective PDE4 inhibitors have been created.

DISCLOSURE OF INVENTION

Under these circumstances, the present inventors made extensive study for the purpose of providing a PDE4 inhibitor effective for the inflammatory diseases and immune diseases. As a result, they found that a nitrogen-containing heterocyclic compound having a novel structure, its salt or hydrates thereof, exhibit superior activity as a PDE4 inhibitor, and also that it is useful as an inhibitor of production of TNFα. Further, the present inventors found that the PDE4 inhibitor of the present invention has the action of lowering blood sugar and is useful as a prophylactic and therapeutic agent for diabetes. Thus, they have accomplished the present invention.

That is, the present invention relates to a nitrogen-containing heterocyclic compound represented by the following formula, its salt or hydrates thereof, and a medicament comprising the same.

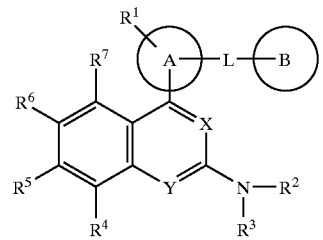

Wherein the ring A is an aromatic hydrocarbon ring which may have a heteroatom, the ring B represents:
1) a saturated hydrocarbon ring which may have a substituent group,
2) an unsaturated hydrocarbon ring which may have a substituent group,
3) a saturated heterocyclic ring which may have a substituent group or
4) an unsaturated heterocyclic ring which may have a substituent group, $R^1$ represents:
1) hydrogen atom,
2) a halogen atom,
3) a $C_{1-6}$ alkyl group which may be substituted with a halogen atom,
4) a $C_{1-6}$ alkoxy group which may be substituted with a halogen atom or
5) an amino group which may be substituted with a $C_{1-6}$ alkyl group or an acyl group, $R^2$ and $R^3$ are the same as or different from and represent:
1) hydrogen atom,
2) a $C_{1-6}$ alkyl group which may have a substituent group,
3) a $C_{3-7}$ cycloalkyl group which may have a substituent group,
4) a $C_{2-6}$ alkenyl group which may have a substituent group or
5) an acyl group, $R^4$, $R^5$, $R^6$ and $R^7$ are the same as or different from and represent:
1) hydrogen atom,
2) a halogen atom, 3) a $C_{1-6}$ alkyl group which may be substituted with a halogen atom, 4) a $C_{3-7}$ cycloalkyl group which may have a substituent group, 5) an aryl group which may have a substituent group, 6) a $C_{1-6}$ alkoxy group which may have a substituent group, 7) a $C_{3-7}$ cycloalkoxy group which may have a substituent group, 8) an aryl alkoxy group which may have a substituent group, or 9) a $C_{1-6}$ alkylthio group which may have a substituent group, 10) a hydroxyl group, 11) an amino group which may be substituted with a $C_{1-6}$, alkyl group or an acyl group, 12) a nitro group, 13) a cyano group, 14) a carboxyl group or 15) a $C_{1-6}$ alkoxy carbonyl group, or 16) neighboring $R^3$, $R^4$, $R^5$ and $R^6$ may be combined to form a ring which may be substituted with a $C_{1-6}$ alkyl group, and the ring being a ring which may form a heterocyclic ring containing one or more atoms selected from the group consisting of a nitrogen atom, an oxygen atom and a sulfur atom, L represents:

1) a single bond, 2) a $C_{1-6}$ alkylene group which may have a substituent group, 3) a $C_{2-6}$ alkenylene group which may have a substituent group, 4) a $C_{2-6}$ alkynylene group which may have a substituent group, or 5) a group represented by the formula —E—G— (wherein E represents:

a) an oxygen atom, b) a sulfur atom, c) formula —CO—, d) —SO—, e) —SO$_2$—, f) —N($R^8$)— (wherein $R^8$ represents hydrogen atom, a $C_{1-6}$ alkyl group or an acyl group), g) —N($R^9$)—CO— (wherein $R^9$ represents hydrogen atom or a $C_{1-6}$ alkyl group) or h) —(CH$_2$)$_m$— which may have a substituent group (wherein m is an integer of 0 to 6), and G represents:

a) a sulfonyl group, b) formula —N($R^{10}$)— (wherein $R^{10}$ represents hydrogen atom, a $C_{1-6}$ alkyl group or an acyl group), or c) —(CH$_2$)$_n$— (wherein n is an integer of 0 to 6)), and X and Y are the same as or different from each other and each represents:

1) a nitrogen atom,

2) =CH— or 3) a carbon atom which may be substituted with a $C_{1-6}$ alkyl group which may have a substituent group, provided that X and Y are not simultaneously carbon atoms which may be substituted with a $C_{1-3}$ alkyl group.

Preferably, X and/or Y is a nitrogen atom.

Further, the present invention provides a phosphodiesterase-4 inhibitor comprising the above-mentioned nitrogen-containing heterocyclic compound, its salt or hydrates thereof. In addition, it provides an inhibitor of production of TNFα, comprising the above-mentioned nitrogen-containing heterocyclic compound, its salt or hydrates thereof. Furthermore, it provides a pharmaceutical composition comprising a pharmacologically effective amount of the above-mentioned nitrogen-containing heterocyclic compound, its salt or hydrates thereof and a pharmaceutically acceptable carrier. Also, it provides a method of preventing or treating diseases against which an inhibitory action on phosphodiesterase-4 is effective for therapy, which comprises administering a pharmacologically effective amount of the above-mentioned nitrogen-containing heterocyclic compound, its salt or hydrates thereof to a patient for whom an inhibitory action on phosphodiesterase-4 is effective for therapy. Further, it provides use of the above-mentioned nitrogen-containing heterocyclic compound, its salt or hydrates thereof in production of a phosphodiesterase-4 inhibitor.

The present invention also encompasses nitrogen-containing heterocyclic compound shown in the following mode, its salt or hydrates thereof.

That is, in the formula, the ring A is a monocyclic or bicyclic aryl group which may have a substituent group and a heteroatom, the ring B represents:

1) a $C_{3-7}$ cycloalkyl group which may have a substituent group and a heteroatom, or 2) a monocyclic or bicyclic unsaturated cycloalkyl group which may have a substituent group and a heteroatom, $R^1$ represents:

1) a hydrogen atom, 2) a halogen atom, 3) a straight-chain or branched $C_{1-6}$ alkyl group which may be substituted with a halogen atom, 4) a $C_{1-6}$ alkoxy group which may be substituted with a halogen atom, or 5) an amino group which may be substituted with a $C_{1-6}$ alkyl or acyl group, $R^2$ and $R^3$ are the same or different and represent:

1) hydrogen atom, 2) a straight or branched $C_{1-6}$ alkyl group which may be substituted with a halogen atom, 3) a $C_{3-7}$ cycloalkyl group, 4) a $C_{2-4}$ alkenyl group, or 5) an acyl group, $R^4$, $R^5$, $R^6$ and $R^7$ are the same or different and represent:

1) hydrogen atom, 2) a halogen atom, 3) a straight or branched $C_{1-6}$ alkyl group which may be substituted with a halogen atom, 4) a $C_{3-7}$ cycloalkyl group, 5) an aryl group which may have a substituent group, 6) a $C_{1-6}$ alkoxy group which may be substituted with a halogen atom, 7) a $C_{3-7}$ cycloalkoxy group, 8) an aryl alkoxy group which may have a substituent group, 9) a $C_{1-6}$ alkylthio group, 10) a hydroxy group, 11) an amino group which may be substituted with a $C_{1-6}$ alkyl group or an acyl group, 12) a nitro group,
13) a cyano group,
14) a carboxyl group or
15) a $C_{1-6}$ alkoxycarbonyl group, or
16) neighboring $R^3$, $R^4$, $R^5$ and $R^6$ may be combined to form an alkylene dioxy ring which may be substituted with a $C_{1-3}$ alkyl group, L represents:
1) a $C_{1-6}$ alkylene group which may have a substituent group,
2) a $C_{2-6}$ alkenylene group which may have a substituent group,
3) a $C_{2-6}$ alkynylene group which may have a substituent group, or
4) formula —E—G—, (wherein E represents:
   a) an oxygen atom,
   b) a sulfur atom which may be oxidized,
   c) an alkylene group represented by the formula —(CH$_2$)$_m$— which may have a substituent group, wherein m is 0 or an integer of 1 to 6,
   d) a group shown in the formula —CO—,
   e) a group represented by the formula —N(R$^8$)— (wherein R$^8$ represents hydrogen atom, a $C_{1-6}$ alkyl group or an acyl group), or
   f) a group represented by the formula —N(R$^9$)— (wherein R$^9$ represents a hydrogen atom or a $C_{1-6}$ alkyl group, and G represents:
   a) a sulfonyl group,
   b) formula —N(R$^{10}$)— (wherein R$^{10}$ represents hydrogen atom, a $C_{1-6}$ alkyl group or an acyl group), or
   c) formula —N(CH$_2$)$_n$— (wherein n is 0 or an integer of 1 to 6), provided that when both E and G are alkylene groups, L is a $C_{1-6}$ alkylene group), and X and Y are the same as or different from each other and each represent:
1) a nitrogen atom, or
2) a carbon atom which may be substituted with a $C_{1-6}$ alkyl group, provided that X and Y are not simultaneously carbon atoms which may be substituted with a $C_{1-3}$ alkyl group.

DETAILED DESCRIPTION OF THE INVENTION

The present invention is as described above, and preferably it is a nitrogen-containing heterocyclic compound of the formula (I), wherein the ring A is a benzene or pyridine ring which may have a substituent group; and the ring B is an unsaturated hydrocarbon ring which may have a substituent group or an unsaturated heterocyclic ring which may have a substituent group, its salt or hydrates thereof, and is a medicament comprising the same.

More preferably, it is a nitrogen-containing heterocyclic compound of the formula (I), wherein the ring A is a benzene or pyridine ring which may have a substituent group; the ring B is an aromatic hydrocarbon ring which may have a substituent group or an aromatic heterocyclic ring which may have a substituent group; L is a single bond, $C_{1-6}$ alkylene group, $C_{2-6}$ alkenylene group, $C_{2-6}$ alkynylene group, the formula —N(R$^8$)—CO—(CH$_2$)$_1$— (wherein R$^8$ has the same meanings as defined above and 1 is an integer of 0 to 6), —N(R$^8$)—SO$_2$— (wherein R$^8$ has the same meanings as defined above), —N (R$^8$)—(CH$_2$)$_1$— (wherein R$^8$ and 1 have the same meanings as defined above) or —CO—N(R$^{10}$)— (wherein R$^{10}$ has the same meanings as defined above); and both X and Y are nitrogen atoms, its salt or hydrates thereof, and is a medicament comprising the same.

Further preferably, it is a nitrogen-containing heterocyclic compound of the formula (I), wherein the ring A is a benzene or pyridine ring; the ring B is a $C_{3-7}$ hydrocarbon ring which may have a substituent group, a benzene ring which may have a substituent group, a naphthalene ring which may have a substituent group, a pyridine ring which may have a substituent group, a pyrrole ring which may have a substituent group, a quinoline ring which may have a substituent group, an imidazopyridine ring which may have a substituent group, an isoindole ring, a phthalimide ring or a benzene ring which may be substituted with an alkylene dioxy group; L is a single bond, —CH$_2$—, —(CH$_2$)$_2$—, —(CH$_2$)$_3$—, —CH=CH—, —C≡C—, the formula —NH—CO—, —CO—NH— or —NH—SO$_2$—; both X and Y are nitrogen atoms; $R_2$ and $R_3$ are the same as or different from and represent hydrogen atom or a $C_{1-6}$ alkyl group which may be substituted with a halogen atom; both $R^4$ and $R^7$ are hydrogen atoms, $R^5$ and $R^6$ are the same as or different from and represent a $C_{1-6}$ alkoxy group which may be substituted with a halogen atom, a $C_{3-7}$ cycloalkoxy group which may have a substituent group, an aryl group which may have a substituent group or an aryl alkoxy group, its salt or hydrates thereof, and is a medicament comprising the same.

In the specification, the structural formulae of these compounds may, for convenience sake, indicate a certain isomer, but the present invention encompasses every possible isomer such as geometric isomer, optical isomer, stereoisomer and tautomer based on asymmetric carbon, which can occur in the structures of these compounds, and mixtures of such isomers, and is not limited to the formulae shown for convenience+ sake.

Hereinafter, the words and phrases used in the specification are described more in detail.

In the formula (I), the phrase "which may have a substituent group" in the definition of the ring A means that the ring A may be substituted with a substituent group such as hydroxyl group; thiol group; nitro group; morpholino group; thiomorpholino group; halogen atom such as fluorine, chlorine, bromine and iodine; nitrile group; azide group; formyl group; alkyl group such as methyl group, ethyl group, propyl group, isopropyl group and butyl group; alkenyl group such as vinyl group, allyl group and propenyl group; alkynyl group such as ethynyl group, butynyl group and propargyl group; alkoxy group such as methoxy group, ethoxy group, propoxy group and butoxy group corresponding to a lower alkyl group; halogenoalkyl group such as fluoromethyl group, difluoromethyl group, trifluoromethyl group and halogenoethyl group; hydroxyalkyl group such as hydroxymethyl group, hydroxyethyl group and hydroxypropyl group; guanidino group; formimidoyl group; acetoimidoyl group; carbamoyl group; thiocarbamoyl group; carbamoyl alkyl group such as carbamoyl methyl group and carbamoyl ethyl group; alkyl carbamoyl group such as methyl carbamoyl group and dimethyl carbamoyl group; carbamide group; alkanoyl group such as acetyl group; amino group; alkyl amino group such as methyl amino group, ethyl amino group and isopropyl amino group; dialkyl amino group such as dimethyl amino group, methyl ethyl amino group and diethyl amino group; amino alkyl group such as amino methyl group, amino ethyl group and amino propyl group; carboxy group; alkoxycarbonyl group such as methoxycarbonyl group, ethoxycarbonyl group and propoxycarbonyl group; alkoxycarbonyl alkyl group such as methoxycarbonyl methyl group, ethoxycarbonyl methyl group, propoxycarbonyl methyl group, methoxycarbonyl ethyl group, ethoxycarbonyl ethyl group and propoxycarbonyl ethyl group; alkyloxyalkyl group such as methyloxymethyl group, methyloxyethyl group, ethyloxymethyl group and ethyloxyethyl group; alkylthioalkyl group such as methylthiomethyl group, methylthioethyl group, ethylthiomethyl group and ethylthioethyl group; aminoalkyl aminoalkyl group such as aminomethyl aminomethyl group and aminoethyl aminoethyl group; alkyl carbonyloxy group such as methyl carbonyloxy group, ethyl carbonyloxy group and isopropyl carbonyloxy group; cycloalkoxy group such as cyclopropoxy group, cyclobutoxy group, cyclopentoxy group and cyclohexanoxy group; arylalkoxy group such as phenoxy group, benzyloxy group and phenethyloxy group; arylalkoxy alkoxy alkyl group such as benzyloxy methyl oxymethyl group and benzyloxy ethyloxy ethyl group; hydroxyalkoxyalkyl group such as hydroxyethyloxymethyl group and hydroxyethyloxyethyl group; arylalkoxyalkyl group such as benzyloxymethyl group, benzyloxyethyl group and benzyloxypropyl group; quaternary ammonio group such as trimethyl ammonio group, methyl ethyl methyl ammonio group and triethyl ammonio group; cycloalkyl group such as cyclopropyl group, cyclobutyl group, cyclopentyl group and cyclohexyl group; cycloalkenyl group such as cyclopropenyl group, cyclobutenyl group, cyclopentenyl group and cylohexenyl group; aryl group such as phenyl group, pyridinyl group, thienyl group, furyl group and pyrrolyl group; alkylthio group such as methylthio group, ethylthio group, propylthio group and butylthio group; arylthio group such as phenylthio group, pyridinylthio group, thienylthio group, furylthio group and pyrrolylthio group; aryl lower alkyl group such as benzyl group, trityl group and dimethoxy trityl group; substituted sulfonyl group such as sulfonyl group, mesyl group and p-toluene sulfonyl group; aryloyl group such as benzoyl group; halogenoaryl group such as fluorophenyl group and bromophenyl group; and oxyalkoxy group such as methylene dioxy group.

Hereinafter, the phrase "may have a substituent group" in the specification has the same meaning as defined above.

The heteroatom in the phrase "may have a heteroatom" means an oxygen atom, sulfur atom, nitrogen atom, phosphorus, antimony, bismuth, silicon, germanium, tin and lead, preferably an oxygen atom, sulfur atom and nitrogen atom, more preferably a nitrogen atom.

Hereinafter, the heteroatom in the phrase "may have a heteroatom" in the specification has the same meaning as defined above.

The aromatic hydrocarbon ring means a benzene ring, pentalene ring, indene ring, naphthalene ring, azulene ring, heptalene ring and benzocycloctene ring. The aryl ring means groups based on the above-mentioned aromatic hydrocarbon rings.

The phrase "aromatic hydrocarbon ring which may have a heteroatom" means an aromatic heterocyclic ring, that is, an aromatic hydrocarbon ring wherein any of 1 to 4 carbon atoms in an aromatic hydrocarbon ring having the same meaning as defined above may be a heteroatom. Examples of such aromatic heterocyclic rings include a pyridine ring, pyrrole ring, imidazole ring, pyrazole ring, pyrazine ring, pyrimidine ring, pyridazine ring, thiophene ring, furan ring, pyran ring, isothiazole ring, isoxazole ring, furazane ring, indolyzine ring, indole ring, isoindole ring, indazole ring, purine ring, quinolidine ring, isoquinoline ring, phthalazine ring, naphthylidine ring, quinoxaline ring, quinazoline ring, cinoline ring, pteridine ring, benzothiophene ring, isobenzofuran ring, benzoxazole ring, benzthiazole ring, benzthiadiazole ring, benzimidazole ring, imidazopyridine ring, pyrrolopyridine ring, pyrrolopyrimidine ring and pyridopyrimidine ring, among which a pyridine ring, pyrimidine ring, imidazole ring and quinoline ring are preferable.

In the specification, the heteroaryl group means groups based on the above-mentioned aromatic heterocyclic rings.

In the formula (I), the phrase "$C_{3-7}$ saturated hydrocarbon ring which may have a substituent group" in the ring B means e.g. 3- to 7-memberred rings such as cyclopropane, cyclobutane, cyclopentane, cyclohexane and cycloheptane, and these hydrocarbon rings may have substituent groups having the same meanings as defined above.

In the specification, the $C_{3-7}$ cycloalkyl group means groups based on the above-mentioned $C_{3-7}$ saturated hydrocarbon rings.

The saturated heterocyclic ring means rings wherein any of 1 to 4 carbon atoms in the above-mentioned $C_{3-7}$ saturated hydrocarbon rings is a heteroatom, and examples of such rings include aziridine, pyrrolidine, piperidine, imidazolidine, pyrazolidine, piperazine, morpholine, oxysilane and oxathiolane. These saturated heterocyclic rings may have substituent groups having the same meanings as defined above.

The phrase "unsaturated hydrocarbon ring which may have a substituent group" means a $C_{3-7}$ saturated hydrocarbon ring having the same meanings as defined above except that the ring has a carbon-carbon double bond, and examples of such rings include monocyclic or bicyclic unsaturated hydrocarbon rings such as cyclopropene, cyclobutene, cyclopentene, cyclohexene and cycloheptene or aromatic hydrocarbon rings having the same meanings as defined above.

The unsaturated heterocyclic ring means an unsaturated hydrocarbon ring having the same meanings as defined above except that any of 1 to 4 carbon atoms therein is a heteroatom, and example of such rings include the same aromatic heterocyclic rings as defined above and unsaturated condensed rings such as phthalimide and succinimide. These unsaturated heterocyclic rings may have substituent groups having the same meanings as defined above.

In the phase "may be substituted with a halogen atom" in $R^1$ in the formula (I), the halogen atom means fluorine, chlorine, bromine, iodine.

Hereinafter, the halogen atom in the specification has the same meanings as defined above.

Examples of the $C_{1-6}$ alkyl group include straight or branched $C_{1-6}$ alkyl groups such as methyl group, ethyl group, n-propyl group, i-propyl group, sec-propyl group, n-butyl group, i-butyl group, sec-butyl group, t-butyl group, n-pentyl group, i-pentyl group, sec-pentyl group, t-pentyl group, n-hexyl group, i-hexyl group, 1,2-dimethyl propyl group, 2-ethyl propyl group, 1-methyl-2-ethyl propyl group, 1-ethyl-2-methyl propyl group, 1,1,2-trimethyl propyl group, 1,2,2-trimethyl propyl group, 1,1-dimethyl butyl group, 2,2-dimethyl butyl group, 2-ethyl butyl group, 1,3-dimethyl butyl group, 2-methyl pentyl group and 3-methyl pentyl group, preferably methyl group, ethyl group, n-propyl group, i-propyl group, sec-propyl group, t-propyl group, n-butyl group, i-butyl group, sec-butyl group, n-pentyl group, i-pentyl group, sec-pentyl group, t-pentyl group, n-hexyl group, i-hexyl group, 1,2-dimethyl propyl group, 2-ethyl propyl group, 1,1-dimethyl butyl group, 2,2- dimethyl butyl group, 2-ethyl butyl group, 1,3-dimethyl butyl group, 2-methyl pentyl group and 3-methyl pentyl group, more preferably methyl group, ethyl group, n-propyl group, i-propyl group, sec-propyl group, n-butyl group, i-butyl group, sec-butyl group, t-butyl group, 1,2-dimethyl propyl group, 2-ethyl propyl group, 1,1-dimethyl butyl group, 2,2-dimethyl butyl group, 2-ethyl butyl group and 1,3-dimethyl butyl group, further preferably methyl group, ethyl group, n-propyl group, i-propyl group, t-propyl group, 1,2-dimethyl propyl group and 2-ethyl propyl group, and most preferably methyl group, ethyl group, n-propyl group, i-propyl group and sec-propyl group.

Hereinafter, the $C_{1-6}$ alkyl group in the specification has the same meanings as defined in above.

The "$C_{1-6}$ alkyl group which may be substituted with a halogen atom" means the $C_{1-6}$ alkyl group defined above provided that any of carbon atoms therein may be substituted with the halogen atom defined above, and examples of such groups include a trifluoromethyl group, 2-chloroethyl group, 1,2-dichloroethyl group, 2-bromoethyl group, 3-bromopropyl group, 3,3,3-trifluoropropyl group, 4-chlorobutyl group, 1,1-dimethyl-3-chloroethyl group and 2,2-dimethyl-4-bromobutyl group.

In the specification, the "$C_{1-6}$ alkyl group which may be substituted with a halogen atom" has the same meanings as defined above.

The $C_{1-6}$ alkoxy group includes alkoxy groups that correspond to the $C_{1-6}$ alkyl groups defined above, and specifically, this group includes a methoxy group, ethoxy group, n-propoxy group, i-propoxy group, sec-propoxy group, n-butoxy group, i-butoxy group, sec-butoxy group, t-butoxy group, n-pentyloxy group, i-pentyloxy group, sec-pentyloxy group, t-pentyloxy group, n-hexyloxy group, i-hexyloxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,2,2-trimethylpropoxy group, 1,1-dimethylbutoxy group, 2,2-dimethylbutoxy group, 2-ethylbutoxy group, 1,3-dimethylbutoxy group, 2-methylpentyloxy group and 3-methylpentyloxy group. The phrase "$C_{1-6}$ alkoxy group which may be substituted with a halogen atom" means a $C_{1-6}$ alkoxy group in which any of carbon atoms may be substituted with the halogen atom defined above, and examples of such groups include a trifluoromethoxy group, 2-chloroethoxy group, 1,2-dichloroethoxy group, 2-bromoethoxy group, 3-bromopropyloxy group, 3,3,3-trifluoropropyloxygroup, 4-chlorobutyloxy group, 1,1-dimethyl-3-chloroethoxy group and 2,2-dimethyl-4-bromobutyloxy group.

In the specification, the "$C_{1-6}$ alkoxy group which may be substituted with a halogen atom" has the same meanings as defined above.

In the phrase "may be substituted with a $C_{1-6}$ alkyl group or acyl group", the acyl group includes e.g. a formyl group, acetyl group, propionyl group, butyryl group, isobutyryl group, valeryl group, isovaleryl group, pivaloyl group, hexanoyl group, acryloyl group, methacryloyl group, crotonyl group, chloroformyl group, pivaloyl group, oxazalo group, methoxalyl group, ethoxalyl group and benzoyl group.

Hereinafter, the acyl group in the specification has the same meanings as defined above.

In the phrase "amino group which may be substituted with a $C_{1-6}$ alkyl group or acyl group", the amino group means an amino group which may be substituted with the same $C_{1-6}$ alkyl group or the same acyl group as defined above, and examples of such groups include a N-formyl amino group, N-acetyl amino group, N-propionyl amino group, N-pivaloyl amino group, N-benzoyl amino group, N-methyl-N-formyl amino group, N-methyl-N-benzoyl amino group, N-methyl amino group, N,N-dimethyl amino group, N-methyl-N-ethyl amino group, N-(n-propyl) amino group, N-(i-propyl) amino group and N-(t-butyl) amino group.

Hereinafter, the "amino group which may be substituted with a $C_{1-6}$ alkyl group or acyl group" in the specification has the same meanings as defined above.

In the formula (I), the "$C_{1-6}$ alkyl group which may be substituted with a halogen atom", the "$C_{3-7}$ cycloalkyl group" and the "acyl group" in the definition of $R^2$ and $R^3$ have the same meanings as defined above.

Specifically, the "$C_{2-6}$ alkenyl group" means e.g. a vinyl group, allyl group, isopropenyl group, 1-propene-2-yl group, 1-butene-1-yl group, 1-butene-2-yl group, 1butene-3-yl group, 2-butene-1-yl group and 2-butene-2-yl group.

In the formula (I), the "halogen atom", the "straight or branched $C_{1-6}$ alkyl group which may be substituted with a halogen atom", the "$C_{3-7}$ cycloalkyl group", the "aryl group which may have a substituent group", the "$C_{1-6}$ alkoxy group which may be substituted with a halogen atom" and the "amino group which may be substituted with a $C_{1-6}$ alkyl group or acyl group" have the same meanings as defined above.

The phrase "$C_{3-7}$ cycloalkoxy group" means cycloalkoxy groups that correspond to the $C_{3-7}$ cycloalkyl groups defined above, and examples include a cyclopropyloxy group, cyclobutyloxy group, cyclopentyloxy group and cyclohexyloxy group.

The phrase "aryl alkoxy group" means an alkoxy group having the same meanings as defined above except that it is substituted with an aryl group having the same meanings as defined above.

The phrase "$C_{1-6}$ alkylthio group" means alkylthio groups that correspond to the $C_{1-6}$ alkyl groups defined above, and examples include a methyl thio group, ethyl thio group, n-propyl thio group, i-propyl thio group, sec-propyl thio group, n-butyl thio group, i-butyl thio group, sec-butyl thio group, t-butyl thio group, 1,2-dimethyl propyl thio group, 2-ethyl propyl thio group, 1,1-dimethyl butyl thio group, 2,2-dimethyl butyl thio group, 2-ethyl butyl thio group and 1,3-dimethyl butyl thio group.

The phrase "$C_{1-6}$ alkoxy carbonyl group" means alkoxy carbonyl groups that correspond to the $C_{1-6}$ alkoxy groups defined above, and examples include a methoxy carbonyl group, ethoxy carbonyl group, n-propoxy carbonyl group, i-propoxy carbonyl group, sec-propoxy carbonyl group, n-butoxy carbonyl group, i-butoxy carbonyl group, 1,2-dimethyl propoxy carbonyl group and 2-ethyl propoxy carbonyl group.

The phrase "neighboring $R^3$, $R^4$, $R^5$ and $R^6$ may be combined to form a ring which may be substituted with a $C_{1-6}$ alkyl group" means that neighboring groups among the substituent groups $R^3$, $R^4$, $R^5$ and $R^6$ may linked to one another to form a heterocyclic ring containing one or more atoms selected from the group consisting of a nitrogen atom, oxygen atom and sulfur atom, and this ring, together with carbon atoms in the benzene ring, forms a 5- to 7-memberred ring. Specifically, such a ring includes rings represented by the formula —O—$(CH_2)_n$—O— (n is an integer of 1 to 3), such as a 2,4-methylene dioxy ring as 5-memberred ring, 2,5-ethylene dioxy ring as 6-memberred ring and 2,6-propylene dioxy ring as 7-memberred ring.

Further, these alkylene dioxy rings may be substituted with $C_{1-3}$ alkyl group. The $C_{1-3}$ alkyl group corresponds to the $C_{1-3}$ alkyl group out of the $C_{1-6}$ alkyl group defined above, and examples include a methyl group, ethyl group, n-propyl group, i-propyl group and sec-propyl group.

In the phrase "$C_{1-6}$ alkylene group which may have a substituent group" in the definition of L in the formula (I), the alkylene group refers to a divalent group derived from a straight-chain $C_{1-6}$ saturated hydrocarbon by removing one hydrogen atom from each of both terminal carbon atoms thereof. Specific examples include a methylene group, ethylene group, propylene group, butylene group, pentylene group and hexylene group, preferably methylene group, ethylene group, propylene group, butylene group and pentylene group, more preferably methylene group, ethylene group, propylene group and butylene group, further preferably methylene group and ethylene group.

In the phrase "$C_{2-6}$ alkenylene group which may have a substituent group", the alkenylene group means a divalent group, which similar to the above-described alkylene group, is derived from a straight-chain $C_{2-6}$ unsaturated hydrocarbon having a carbon-carbon double bond by removing one hydrogen atom from each of both terminal carbon atoms thereof. Specific examples include a vinylene group, propenylene group, butenylene group, pentenylene group and hexenylene group, preferably vinylene group, propenylene group, butenylene group and pentenylene group, more preferably vinylene group, propenylene group and butenylene group, further preferably vinylene group and propenylene group.

In the phase "$C_{2-6}$ alkynylene group which may have a substituent group", the alkynylene group refers to a divalent group, which similar to the groups described above, is derived from a straight $C_{2-6}$ unsaturated hydrocarbon having a carbon-carbon triple bond by removing one hydrogen atom from each of both terminal carbon atoms thereof. Specific examples include an ethynylene group, propynylene group, butynylene group, pentynylene group and hexynylene, preferably ethynylene group, propynylene group, butynylene group and pentynylene group, more preferably ethynylene group, propynylene group and butynylene group, further preferably ethynylene group and propynylene group.

In the formula —E—G—, E is defined to be an oxygen atom, a sulfur atom, the formula —CO—, —SO—, —SO$_2$—, —N(R$^8$)— (wherein, R$^8$ represents hydrogen atom, $C_{1-6}$ alkyl group or acyl group), —N(R$^9$)—CO— (wherein, R$^9$ represents hydrogen atom or $C_{1-6}$ alkyl group) or —(CH$_2$)$_m$— which may have a substituent group (wherein, m is an integer of 0 to 6), and G is defined to be a sulfonyl group, the formula —N(R$^{10}$)— (wherein, R$^{10}$ represents hydrogen atom, $C_{1-6}$ alkyl group or acyl group) or —(CH$_2$)$_n$— (wherein, n is an integer of 0 to 6).

Specifically, the following structures can be mentioned.

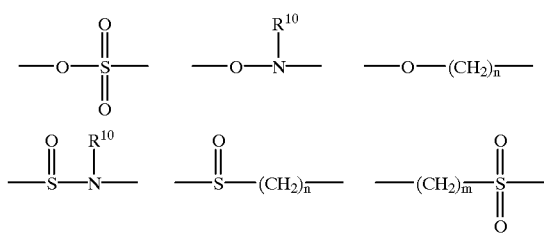

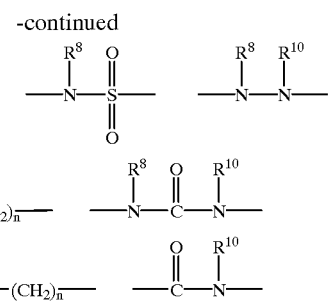

When m is 0 in the above definition, E is a single bond so that the ring A is linked directly to G. When n is 0, G is a single bond so that the ring B is linked directly to E. When m and n are simultaneously 0, L as a whole represents a single bond so that the ring A is linked directly to the ring B. L may be bound to any position of the rings A and B.

X and Y are the same or different and represent a nitrogen atom, =CH— or a carbon atom which may be substituted with a $C_{1-6}$ alkyl group which may have a substituent group. The phrase "may be substituted with a $C_{1-6}$ alkyl group" means that the carbon atom may be substituted with any of the $C_{1-6}$ alkyl groups defined above.

However, the compounds represented by the formula (I) do not include those wherein X and Y are simultaneously carbon atoms which may be substituted with a $C_{1-3}$ alkyl group, its salt or anhydrides thereof. The $C_{1-3}$ alkyl group in this case means $C_{1-3}$ alkyl groups out of the $C_{1-6}$ alkyl groups defined above.

In the present invention, the salts include e.g. inorganic acid salts such as hydrofluorate, hydrochloride, hydrobromate, hydroiodate, sulfate, nitrate, perchlorate, phosphate, carbonate and bicarbonate; organic carboxylic acid salts such as acetate, maleate, tartrate and fumarate; organic sulfonic acid salts such as methane sulfonate, trifluoromethane sulfonate, ethane sulfonate, benzene sulfonate and toluene sulfonate; amino acid salts such as alginate, aspartate and glutamate; amine salts such as trimethyl amine salt, triethylamine salt, procaine salt, pyridine salt and phenethyl benzyl amine salt; alkali metal salts such as sodium salt and potassium salt; and alkaline earth metal salts such as magnesium salt and calcium salt.

Although the dosage of the medicament according to the present invention is varied depending on the severeness of symptoms, age, sex, body weight, administration form and the type of disease, the medicament is given daily in one portion or in divided portions in a daily dose, per man, of usually about 30 µg to 10 g, preferably 100 µg to 5 µg, more preferably 100 µg to 100 mg for oral administration, or about 30 µg to 1 g, preferably 100 µg to 500 mg, more preferably 100 µg to 30 mg for injection.

The administration form of the compound of the present invention is not particularly limited and may be administered orally or parenterally in a usual manner. For example, it can be administered as a pharmaceutical preparation in the form of e.g. tablets, powder, granules, capsules, syrups, troches, inhalations, suppositories, injections, ointments, eye ointments, eye drops, nose drops, ear drops, poultices and lotions.

These pharmaceutical preparations are produced in a usual manner by blending generally used ingredients as starting materials, where ordinarily used fillers, binders, lubricants, coloring agents, taste and odor correctives and as necessary stabilizers, emulsifiers, absorption promoters, surfactants, pH adjusters, preservatives and antioxidants can be used for pharmaceutical manufacturing.

These ingredients include e.g. animal and vegetable oils such as soybean oil, tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicon resin; silicon oil; surfactants such as polyoxyethylene fatty ester, sorbitan fatty ester, glycerin fatty ester, polyoxyethylene sorbitan fatty ester, polyoxyethylene hardened castor oil and polyoxyethylene polyoxypropylene block copolymer; water-soluble polymers such as hydroethyl cellulose, polyacrylic acid, carboxyvinyl polymer, polyethyleneglycol, polyvinyl pyrrolidone and methyl cellulose; lower alcohols such as ethanol and isopropanol; polyvalent alcohols such as glycerin, propylene glycol, dipropylene glycol and sorbitol; sugars such as glucose and sucrose; and inorganic powder such as silicic anhydride, aluminum magnesium silicate and aluminum silicate, and pure water.

For example, the compounds represented by the formula (I) can be produced in the following manner.

Production Method 1

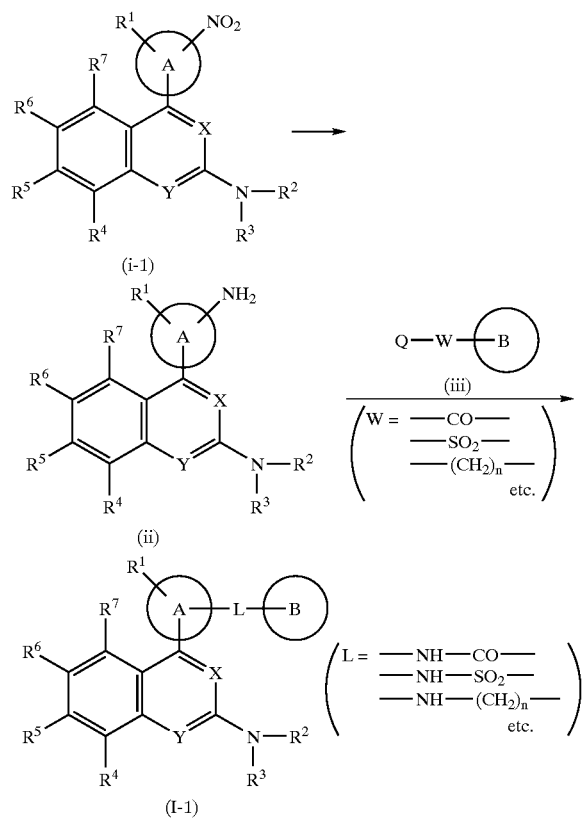

Wherein, X, Y, $R^1$ to $R^7$, ring A, ring B and L have the same meanings as defined above. Q means a halogen atom such as chlorine, bromine and iodine, or a hydroxyl group. In Production Method 1, Compound (i-1) having a nitro group is converted by reduction reaction into an amine (ii), and then (ii) is reacted with (iii) to give Compound (I-1) wherein L is e.g. $-N(R^9)-CO-(CH_2)_n-$ ($R^9$ and n have the same meanings as defined above), $-N(R^8)-SO_2-$ ($R^8$ has the same meanings as defined above), $-N(R^8)-(CH_2)_n-$ ($R^8$ and n have the same meanings as defined above) etc.

The reduction reaction for obtaining (ii) from (i-1) can be conducted for example by catalytic hydrogenation with a catalyst, reduction with a metal such as iron and a metal salt, or by a metal-hydrogen complex compound having a Lewis acid or a metal salt combined with sodium borohydride, among which catalytic hydrogenation in a usual manner is most preferable when the compound has substituent groups which are stable even under catalytic hydrogenation. In the case of catalytic hydrogenation, any metal catalyst such as 10% palladium-carbon powder (hydrate), which allows the reaction to proceed, can be used. The solvent used may be any solvent which does not affect the reaction, and for example, an alcohol type solvent such as ethanol, an ether type solvent such as tetrahydrofuran or a mixed solvent thereof can be mentioned. By adding a tertiary amine such as triethylamine, further good results can also be obtained. If (i-1) has substituent groups which are not suitable for catalytic hydrogenation, the reduction thereof with a metal such as iron is preferable.

Preferable examples of (iii) are carboxylic acid compounds and sulfonic acid compounds having an eliminating group Q and a ring corresponding to the ring B. For example, a carbonyl chloride compound or a carboxylic acid compound corresponding to the ring B is allowed to react at room temperature to 60° C. for 0.5 to 6 hours in the presence of an organic base such as pyridine and any salt such as potassium carbonate, sodium carbonate and barium carbonate, whereby Compound (I-1) wherein L is $-N(R^9)-CO-(CH_2)_n-$ ($R^9$ and n have the same meanings as defined above) can be obtained. In other cases where (iii) is an alkyl halide compound, a sulfonyl chloride compound, an isocyanate compound, a 2,5-dimethoxy tetrahydrofuran compound or a phthalic carbaldehyde compound, each of these compounds is reacted with (ii), whereby Compound (I-1) can be obtained as its corresponding alkyl amino compound, sulfonamide compound, ureido compound, pyrolyl compound or isoindolynyl compound. The reaction solvent includes e.g. ether type solvents such as tetrahydrofuran and 1,4-dioxane, dimethylformamide, N-methyl-2-pyrrolidine, and a mixed solvent thereof, and the reaction can be conducted in the absence of a solvent. (I-1) can also be produced by reacting (ii) with the carboxylic acid compound in the presence of a dehydrogenation condensation agent and as necessary a tertiary amine such as triethylamine. In this case, further good results can be obtained by adding e.g. 1-hydroxybenzotriazole. The dehydration condensation agent includes e.g. N-ethyl-N'-(3-dimethylaminopropyl)carbodiimide hydrochloride and dicyclohexyl carbodiimide, and the solvent includes e.g. acetonitrile, dimethylformamide and N-methyl-2-pyrrolidinone.

Production Method 2

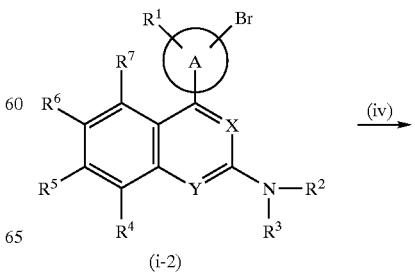

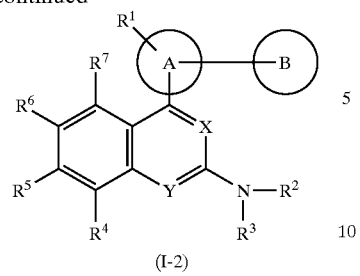

(I-2)

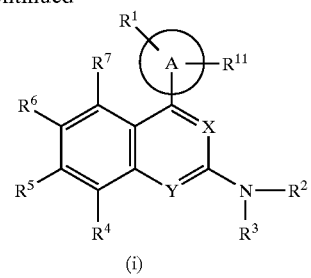

(i)

Compound (I), wherein L is a single bond, a $C_{2-6}$ alkenylene group which may have a substituent group or a $C_{2-6}$ alkynylene group which may have a substituent group, can be produced by Production Method 2 shown above. In this reaction scheme, Compound (iv) means boric acid, dialkoxy borane, dialkyl borane and a trialkyl tin compound, all of which have a ring corresponding to the ring B, or the corresponding alkene or the corresponding alkyne.

In this method, (i-2) is reacted with (iv) in the presence of a catalyst. The reaction is conducted at about 40 to 80° C. for approx. 1 to 24 hours in a nitrogen stream, where any solvent which does not affect the reaction, for example a 2-phase solvent composed of an organic solvent such as toluene, tetrahydrofuran and a mixed solvent thereof and 2 M aqueous sodium carbonate, and a mixed solvent of dimethylformamide and triethylamine, can be used. As the catalyst, any palladium complex allowing the reaction to proceed can be used, and tetrakis(triphenyl phosphine)palladium or bis(triphenyl phosphine)palladium chloride is preferably used. By adding copper iodide etc. depending on the case, further good results can be obtained.

Compound (I-2) obtained in this production method can be easily converted into Compound (I) wherein L is an alkylene chain. That is, Compound (I-2) wherein L is an alkynylene-chain is subjected to an ordinarily known reaction of reducing —C≡C—, for example a reaction with a Lindlar catalyst/triethylamine etc., whereby Compound (I) having the desired alkylene chain can be easily obtained.

Compounds (i-1) and (i-2) in Production Methods 1 and 2 can be produced respectively in synthetic methods known in the art. One of such methods is Production Method 3 below.

Production Method 3

Production Method 3 is a method wherein (v) is reacted in the presence of a catalyst with (vi), that is, boric acid, dialkoxy borane, dialkyl borane or trialkyl tin compound, thus producing (vii), and (vii) is then reacted with an amine to produce the desired product (i). In the reaction scheme, $R^{11}$ means a substituent group such as nitro group and halogen atom.

As the catalyst in the reaction of (v) with (vi), a non-valent or divalent palladium complex such as tetrakis(triphenyl phosphine)palladium can be used. The reaction can be conducted in a two-phase solvent of an organic solvent and 2 M aqueous sodium carbonate in a nitrogen stream at about 40 to 80° C. for about 1 to 24 hours. Any solvent which does not affect the reaction can be used as the organic solvent, and for example, toluene, tetrahydrofuran and mixed solvents thereof can be mentioned. The reaction between (vii) and the amine can be conducted in a usual manner with or without the solvent at about 60 to 180° C. for approx. 1 to 24 hours. In this case, any solvent which does not affect the reaction can be used, and preferable examples include alcohol type solvents such as isopropyl alcohol, ether type solvents such as tetrahydrofuran and 1,4-dioxane, dimethylformamide, N-methyl-2-pyrrolidinone, and mixed solvents thereof. In this reaction, further good results can be obtained by adding salts such as potassium carbonate, sodium carbonate and barium carbonate, and tertiary amines such as triethylamine, diisopropyl ethylamine and DBU, among which tertiary amines such as triethylamine, diisopropyl ethylamine and DBU are preferably used.

In the case of (v) wherein both X and Y are nitrogen atoms, the quinazoline compound (x) corresponding to (v) can be produced by Production Method 4 below.

Production Process 4

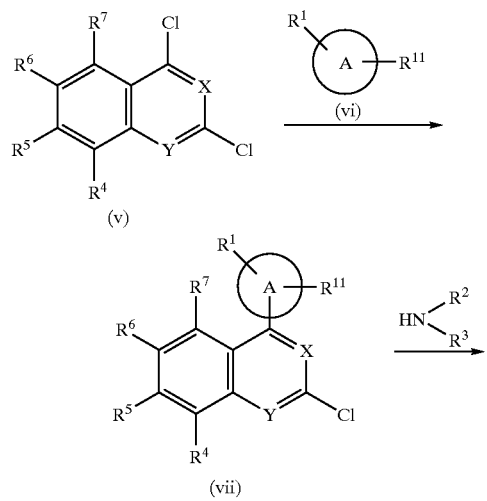

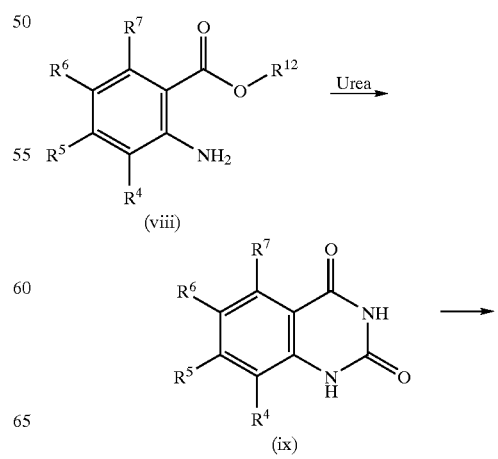

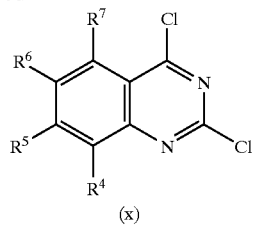
(x)

In this production method, a reaction product (ix) obtained from (viii) and urea is treated with a chlorinating reagent thereby producing (v). Herein, $R^{12}$ may be a group such as $C_{1-6}$ alkyl group insofar as —$OR^{12}$ can function as an eliminating group. The reaction of (viii) with urea can be conducted with or without a solvent such as N-methyl-2-pyrrolidinone. In the reaction of obtaining (v) from (ix), e.g. achlorinating reagent such as phosphorus oxychloride and phosphorus pentachloride can be used, and this reaction can be conducted in a solvent such as tertiary amine e.g. diisopropyl ethylamine or N,N-dimethylformamide, which does not adversely affect the reaction.

In the case of (vii) wherein both X and Y are nitrogen atoms, its corresponding quinazoline compound can be produced in Production Method 5 below.

Production Method 5

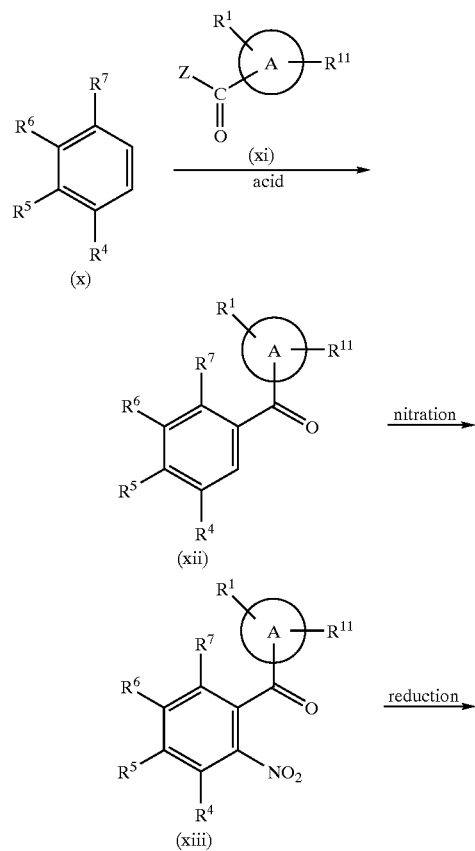

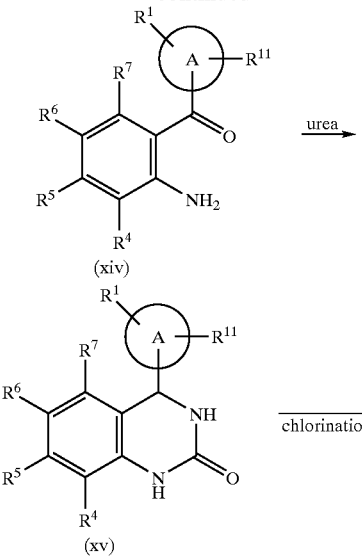

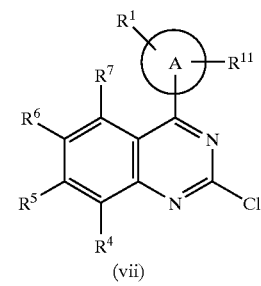

$R^{11}$ in (xi) have the same meanings as defined above. The coupling of (x) with (xi) is conducted in the presence of an acid such as Lewis acid in any solvent not affecting the reaction. (xi) represents an aryl carbonyl halide which may have a substituent group, or its carboxylic acid, or heteroaryl carbonyl halide which may have a substituent group, or its carboxylic acids. As the Lewis acid, e.g. tin tetrachloride can be used. The solvent may be e.g. a halogen type solvent such as dichloromethane.

(xiii) is obtained by nitrating (xii) with a nitrating agent such as nitric acid, a mixed acid consisting of nitric acid and sulfuric acid, metal nitrates such as sodium nitrate and copper nitrate, acetyl nitrate, or nitronium salts such as nitronium tetrafluoroborate. As the nitrating agent, copper nitrate is particularly preferable. The solvent used may be any solvent such as acetic anhydride, which allows the reaction to proceed.

The reduction reaction of converting (xiii) into (xiv) can be conducted in the same manner as in the reduction reaction of (i-1) in Production Method 1. The reaction of (xiv) with urea can be carried out in a solution or suspension with or without the solvent at about 150 to 200° C. for approx. 1 to 6 hours. The solvent is preferably e.g. N-methyl-2-pyrrolidinone etc.

The reaction of obtaining (xvi) from (xv) can be conducted in a usual manner by treating (xv) with phosphorus oxychloride or phosphorus pentachloride. Although any solvent which does not affect the reaction can be used, tertiary amines such as diisopropyl ethylamine, or N,N-dimethylformamide, is preferably used.

The above-mentioned compound (xiv) can also be produced in Production Method 6 below.

Production Method 6

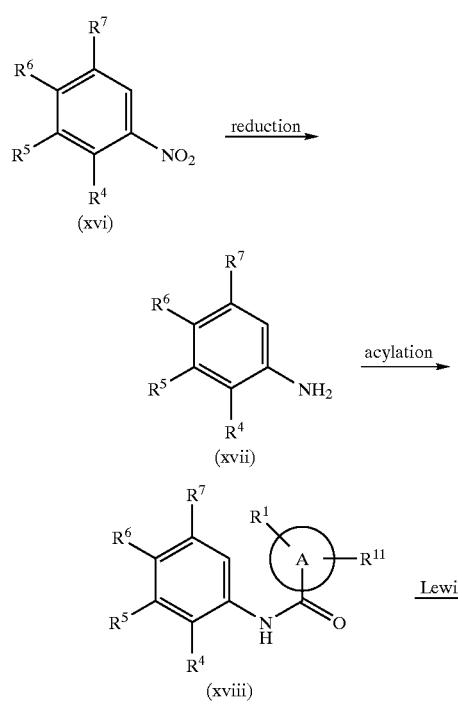

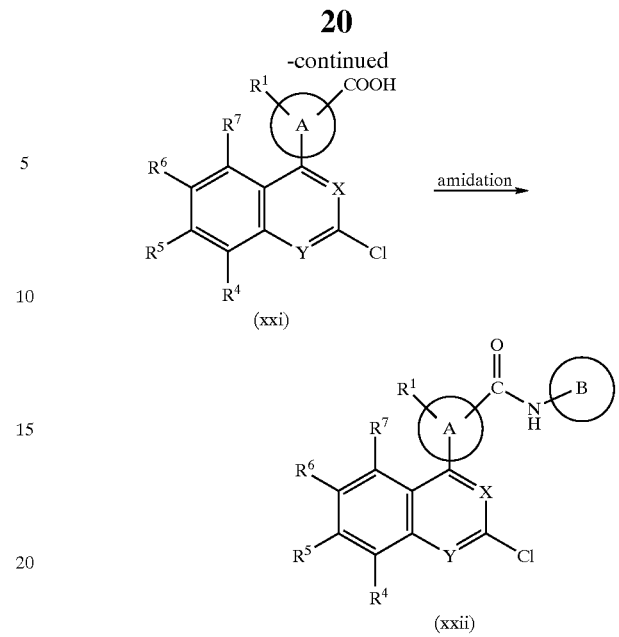

Compound (xvii) can be obtained by treating (xvi) in the same manner as in the reduction reaction of (i-1) in the above Production Method 1. Compound (xviii) can be obtained by treating the resulting (xvii) with the corresponding carbonyl chloride compound or carboxylic acid compound in the same manner as in the acylation reaction for obtaining (I) from (ii) in the above Production Method 1.

The reaction of obtaining (xiv) from (xviii) can be conducted by the transition reaction of (xviii). That is, (xviii) is allowed to react together with a Lewis acid such as aluminum chloride with or without a solvent at about 180 to 250° C. for approx. 0.1 to 2 hours, where any solvent not affecting the reaction can be used.

A typical process for producing Compound (I) wherein L is —CO—N($R^{10}$)— ($R^{10}$ has the same meanings as defined above) is shown in Production Method 7 below.

Production Example 7

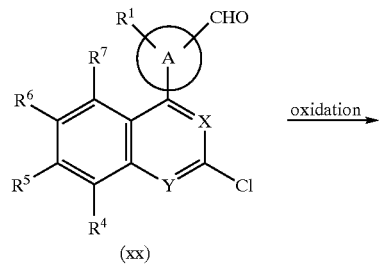

In this process, the desired compound (xxii) is produced by amidation of the —CHO group in (xx). First, the reaction of oxidizing the —CHO group in (xx) into —COOH group can be conducted in a usual manner by use of an usual oxidizing agent. For example, there is a method of reacting (xx) with a Jones reagent at about 0 to 80° C. for approx. 1 to 6 hours in a solvent such as acetone not influencing the reaction. The amidation of the —COOH group in (xxi) can be effected in a usual manner by use of an amine compound corresponding to the ring B and a dehydration condensation agent. For example, Compound (xxi) the amino compound, the dehydration condensation agent and as necessary a tertiary amine such as triethylamine are dissolved in a solvent and reacted at about 0 to 60° C. for approx. 1 to 24 hours, whereby the desired compound can be produced. In this case, further good results can be obtained by adding 1-hydroxybenzotriazole etc. Although the dehydration condensation agent may be any one which allows the reaction to proceed, N-ethyl-N'-(3-dimethylaminopropyl) carbodiimide hydrochloride, dicyclohexyl carbodiimide etc. are preferable. Although the solvent may be any solvent which does not influence the reaction, acetonitrile, dimethylformamide, N-methyl-2-pyrrolidinone etc. are preferable. Further, similar results can also be obtained by chlorinating it with thionyl chloride and subsequent reaction with the corresponding amine compound.

After the reaction is completed, the product can be purified as desired by conventional treatment methods such as column chromatography on silica gel, adsorption resin etc. or recrystallization from a suitable solvent.

The pharmacological actions of the compound according to the present invention were confirmed by the following test methods.

TEST EXAMPLE 1
Inhibitory Action on PDE4

PDE4D was cloned from human placental mRNA by PCR techniques, and cDNA after an alternative spliced site (Mol. Cell. Biol., 13, 6558, 1993) was expressed in BHK cells. Two clones of BHK cells expressing PDE4 activity which was 100 or more times as high as endogenous PDE4 activity were obtained, and one of the clones was cultured in a large amount, and its homogenate was used as an enzyme source of PDE4.

50 mM Tris-HCl (pH 8.0), 0.1 mM EGTA, 0.1 mM MgCl$_2$, 1 μM [$^3$H]-cGMP (100,000 dpm/tube) or 1 μM [$^3$H]-cAMP (100,000 dpm/tube) was added to the above homogenate, and 0.2 ml of the mixture was incubated at 30° C. for 10 to 20 minutes in the presence or absence of a test compound. The enzyme reaction was stopped by incubating the mixture at 95° C. for 1.5 minutes, and after cooling on ice, 50 μl nucleotidase (10 units/ml) was added thereto and incubated at 30° C. for 10 minutes. 550 μl of AG1-X2 resin slurry (H$_2$O:resin=2:1) was added to the reaction mixture, then left at 4° C. for 10 minutes and centrifuged (10,000 rpm, 2.5 minutes, 4° C.), and 450 μl of the supernatant was measured for radioactivity.

The activity was compared in terms of IC$_{50}$ (concentration of the compound at which 50% of the enzyme activity is inhibited). IC$_{50}$ was determined by plotting of the concentration of cAMP as the substrate and the concentration of the compound on logarithmic graph paper. The results shown in Table 1 are the average in triplicate measurements. The test compound was first dissolved in DMSO and then diluted with the above-mentioned buffer for use.

TABLE 1

| Ex. No. | PDE4 Inhibition IC$_{50}$ (nM) |
|---|---|
| 2 | 8.5 |
| 14 | 4 |
| 17 | 4.2 |
| 18 | 1.4 |
| 21 | 2.2 |
| 30 | 2.6 |
| 31 | 2.5 |
| 32 | 2.6 |
| 34 | 3.1 |
| 44 | 2.5 |
| 45 | 0.72 |
| 49 | 1.1 |
| 51 | 3.2 |
| 52 | 1.8 |
| 53 | 0.63 |
| 54 | 1.7 |
| 56 | 1.2 |
| 58 | 2.8 |
| 60 | 0.22 |
| 61 | 0.6 |
| 62 | 1.9 |
| 63 | 0.6 |
| 64 | 0.19 |
| 65 | 2.5 |

TEST EXAMPLE 2
Inhibitory Action on Production of TNF

Human peripheral blood was collected in heparin (1%) and centrifuged (1000 rpm, 10 minutes, at room temperature) to remove platelet rich plasma, and then the blood sample was mixed with Hank's balanced salt solution (HBSS) (with an equal volume to the removed plasma) containing penicillin (100 units/ml) and streptomycin (100 μg/ml) (referred to hereinafter as "p, s"). Ficoll-paque (Pharmacia) with an volume of 3/5 relative to the sample mixture was layered on the lower layer and centrifuged at 1500 rpm for 30 minutes at room temperature, and the monocyte nucleus fraction was collected. The resulting monocyte nucleus fraction was washed twice with p, s-containing HBSS and prepared as a cell float at a cell density of 2–4×10$^6$ cells/ml in p, s-containing RPMI1640 (containing 10% FCS). 400 μl of the prepared cell float was added to a 48-wells culture plate, and 50 μl LPS (100 ng/ml of saline) and 50 μl of each of compound solutions prepared at various concentrations were added to each well, followed by incubation at 37° C. in a 5% CO$_2$ mixed air. After incubation for 18 to 24 hours, the incubated buffer was separated, and TNFα thus released from the cells was measured by an ELISA kit (Amasham).

The inhibitory action of the compound on production of TNFα was determined in terms of IC$_{50}$ by plotting the concentrations of the compound and the amount of produced TNFα (% relative to the control) on semilogarithmic graph paper. The control (100%) for the amount of TNFα produced was obtained by subtracting the amount of TNFα produced in the (basal) group where neither LPS nor the compound was added, from the amount of TNFα produced in the (control) group where the compound was not added. The results are shown in Table 2.

After the compound was dissolved at a concentration of 10 mM in DMSO, a DMSO solution containing the compound at a concentration which was 1000 times as high as the final concentration, and then the solution was diluted with RPMI1640 containing 10% FCS and p, s, to prepare a solution containing the compound at a concentration which was 10 times as high as the final concentration. In place of the compound solution, RPMI1640 (1% DMSO, 10% FCS) containing p, s was added to the control group and basal group. In place of the LPS solution, physiological saline was added to the basal group.

TABLE 2

| Ex. No. | TNF$^\alpha$ Inhibition IC$_{50}$ (nM) |
|---|---|
| 2 | 4.7 |
| 14 | 1.6 |
| 18 | 3.3 |
| 32 | 2.3 |
| 49 | 1.7 |

TEST EXAMPLE 3
Blood Sugar-Depressing Action (ZDF Rat)

A test compound was suspended in 0.5% MC, and the suspension was orally administered to an animal once every day for 1 week. After the administration, the rat was allowed to fast for 4 hours, and blood was collected from the tail vein, added immediately to 0.6 M HClO$_4$ (blood: 0.6 M HClO$_4$=1:9), and centrifuged to give a supernatant which was then measured for glucose level by Glucose CII Test Wako Kit (Wako Pure Chemical Industries, Ltd., JP). In the table, values in the parentheses under the blood sugar level (mg/dl) indicate glucose levels relative to those (=100%) before the administration of the test compound.

TABLE 3

| Ex. No. | Before the administration (mg/dl) | After the continuous administration for 1 week (mg/dl) |
|---|---|---|
| Control | 478.3 ± 38.2 (100) | 530.3 ± 69.5 (110.9) |
| 32 | 478.5 ± 7.3 (100) | 349.3 ± 44.3 (73.0) |
| 62 | 478.6 ± 24.0 (100) | 369.1 ± 37.3 (77.1) |

From the above results, the compound of the present invention is useful as a PDE4 inhibitor, and on the basis of this inhibitory action, the compound is further useful as an inhibitor of production of TNFα. The compound of the present invention is very useful as a prophylactic and therapeutic agent for diseases in which cyclic AMP or TNFα is involved, such as inflammatory diseases such as arthritis, chronic joint rheumatism and asthma, immune diseases such as autoimmune disease, allograft rejection and graft versus host disease, central diseases such as multiple sclerosis, and sepsis, psoriasis and osteoporosis.

Further, the present inventors found that the compound of the present invention useful as a PDE4 inhibitor lowers blood sugar levels significantly in animals with diabetes. The compound of the present invention is also very useful as a prophylactic and therapeutic agent against diabetes.

Hereinafter, the present invention is described in more detail with reference to Production Examples and Examples. However, it goes without saying that the present invention is not limit thereto.

PRODUCTION EXAMPLE 1

2-Chloro-6,7-dimethoxy-4-(3-nitrophenyl) quinazoline

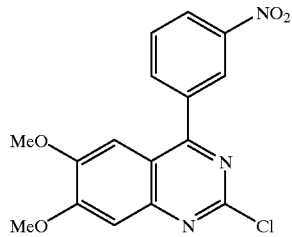

3.16 g of 3,4-dichloro-6,7-dimethoxy quinazoline, 2.04 g of 3-nitrophenyl boric acid and 1.00 g tetrakis(triphenyl phosphine)palladium were suspended in a mixed solvent of 200 ml toluene and 100 ml of 2 M aqueous sodium carbonate and stirred at 60° C. for 15 hours in a nitrogen stream. The organic layer was recovered, washed with water and then with brine, and then dried over anhydrous magnesium sulfate. The solvent was evaporated and the crude product was purified and separated by silica gel column chromatography (hexane:ethyl acetate=2:1). The product was recrystallized from ethanol to give 3.50 g of the title compound as colorless crystals.

$^1$H-NMR (400 MHz, CDCl$_3$) δ; 3.92(3H, s), 4.09(3H, s), 7.19(1H, s) 7.38(1H, s), 7.80(1H, dd, J=8.2, 7.7 Hz), 8.16 (1H, ddd, J=7.7, 1.6, 1.2 Hz), 8.44(1H, ddd, J=8.2, 2.1, 1.2 Hz), 8.68(1H, dd, J=2.1, 1.6 Hz).

m.p.; 228–230° C.

MASS 346 (MH$^+$)

PRODUCTION EXAMPLE 2

4-(3-Biphenylyl)-2-chloro-6,7-dimethoxy quinazoline

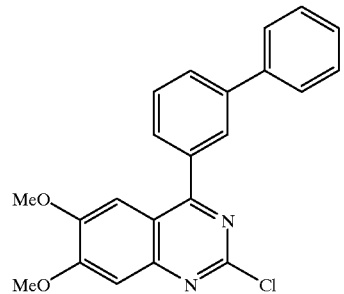

Starting from 3-biphenyl boric acid (1.45 g) obtained from 3-bromobiphenyl according to the method of *J. Org. Chem.*, 56, 3763, 1991. and 3,4-dichloro-6,7-dimethoxyquinazoline (1.50 g), 1.84 g of the title compound was obtained as a colorless crystals in the same manner as in Production Example 1.

$^1$H-NMR (400 MHz, CDCl$_3$) δ; 3.91(3H, s), 4.08 (3H, s), 7.36 (1H, s), 7.37(1H, s) , 7.39(1H, m), 7.47(2H, m), 7.64(1H, t, J=8.0 Hz), 7.65(2H, m), 7.73(1H, dt, J=8.0, 1.6 Hz), 7.80(1H, dt, J=8.0, 1.6 Hz), 8.00(1H, dt, J=1.6 Hz).

PRODUCTION EXAMPLE 3

4-(3-Bromophenyl)-2-chloro-6,7-dimethoxy quinazoline

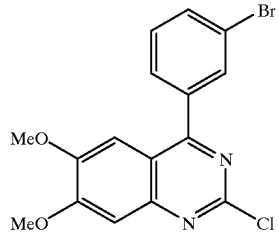

$^1$H-NMR (400 MHz, CDCl$_3$) δ; 3.92(3H, s), 4.08(3H, s), 7.24(1H, s), 7.35(1H, s), 7.45(1H, dd, J=7.9, 7.7 Hz), 7.70(1H, ddd, J=7.7, 1.4, 1.0 Hz), 7.77(1H, ddd, J=7.9, 2.0, 1.0 Hz), 7.94(1H, dd, J=2.0, 1.4 Hz).

PRODUCTION EXAMPLE 4

6,7-Dimethoxy-2-methylamino-4-(3-nitrophenyl) quinazoline

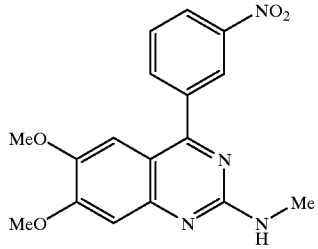

2.50 g of 2-chloro-6,7-dimethoxy-4-(3-nitrophenyl) quinazoline obtained in Production Example 1, 4.89 g methylamine hydrochloride and 11.0 g triethylamine were suspended in 25 ml 1-methyl-2-pyrrolidinone and stirred at 130° C. for 18 hours in a sealed tube. Ethyl acetate and tetrahydrofuran were added thereto, and the reaction solution was washed with water 5 times and then with brine and dried over anhydrous magnesium sulfate. The solvent was evaporated, and the crude product was purified and separated by silica gel column chromatography (hexane:ethyl acetate=1:2). The product was recrystallized from tetrahydrofuran-ethyl acetate to give 1.89 g of the title compound as yellow crystals.

$^1$H-NMR (400 MHz, CDCl$_3$) δ; 3.14(3H, d, J=5.0 Hz), 3.82(3H, s), 4.05(3H, s), 5.14(1H, br s), 6.97(1H, s), 7.10 (1H, s), 7.74(1H, dd, J=8.2, 8.0 Hz), 8.07(1H, ddd, J=8.0, 1.8, 1.1 Hz), 8.39(1H, ddd, J=8.2, 2.1, 1.1 Hz), 8.62(1H, dd, J=2.1, 1.8 Hz).

m.p.; 218–220° C.

MASS 341 (MH$^+$)

PRODUCTION EXAMPLE 5

6,7-Dimethoxy-2-ethylamino-4-(3-nitrophenyl) quninazoline

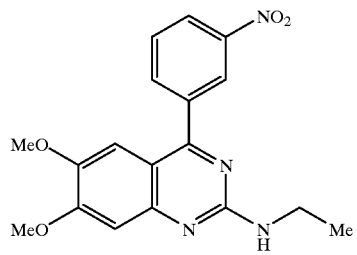

Starting from 500 mg 2-chloro-6,7-dimethoxy-4-(3-nitrophenyl)quinazoline and 1.18 g ethylamine hydrochloride, 183 mg of the title compound was obtained as yellow crystals in the same manner as in Production Example 4.

$^1$H-NMR (400 MHz, CDCl$_3$) δ; 1.31(3H, t, J=7.2 Hz), 3.59(2H, m), 3.82(3H, s), 4.04(3H, s), 5.11(1H, br s), 6.96 (1H, s), 7.08(1H, s), 7.74(1H, dd, J=8.2, 7.7 Hz), 8.06(1H, ddd, J=7.7, 1.6, 1.1 Hz), 8.39(1H, ddd, J=8.2, 2.2, 1.1 Hz), 8.62(1H, dd, J=2.2, 1.6 Hz).

m.p.; 164–166° C.

MASS 355 (MH$^+$)

PRODUCTION EXAMPLE 6

2-Cyclopropylamino-6,7-dimethoxy-4-(3-nitrophenyl)quinazoline

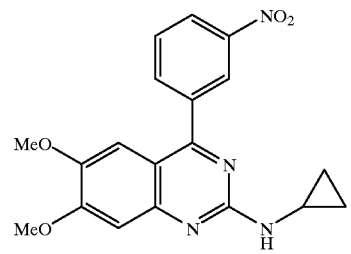

Starting from 500 mg 2-chloro-6,7-dimethoxy-4-(3-nitrophenyl)quinazoline and 414 mg cyclopropylamine hydrochloride, 134 mg of the title compound was obtained in the same manner as in Production Example 4.

$^1$H-NMR (400 MHz, CDCl$_3$) δ; 0.62 (2H, m), 0.89(2H, m), 2.93(1H, m), 3.83(3H, s), 4.05(3H, s), 5.38(1H, brs), 6.98(1H, s), 7.15(1H, s), 7.74(1H, dd, J=8.2, 7.7 Hz), 8.07(1H, ddd, J=7.7, 1.4, 1.1 Hz), 8.39(1H, ddd, J=8.2, 2.2, 1.1 Hz), 8.62(1H, dd, J=2.2, 1.4 Hz).

m.p.; 140–142° C.

MASS 367 (MH$^+$)

PRODUCTION EXAMPLE 7

4-(3-Aminophenyl)-6,7-dimethoxy-2-methylaminoquinazoline

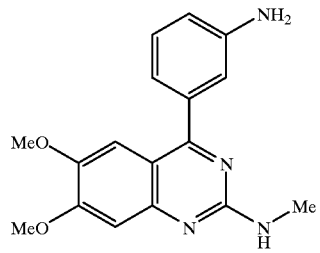

1.83 g of 6,7-dimethoxy-2-methylamino-4-(3-nitrophenyl)quinazoline obtained in Production Example 4, 200 mg of 10% palladium-carbon powder (hydrate) and 1.44 g triethylamine were suspended in a mixed solvent of 10 ml ethanol and 10 ml tetrahydrofuran. After the atmosphere was replaced with hydrogen, the mixture was stirred for 15 hours at ordinary pressure at room temperature. The reaction solution was filtered, then the filtrate was evaporated, and the crude product was purified and separated by silica gel column chromatography (hexane:ethyl acetate=1:3). The product was recrystallized from hexane-ethyl acetate to give 1.22 g of the title compound as pale yellow crystals.

$^1$H-NMR (400 MHz, CDCl$_3$) δ; 3.11(3H, d, J=5.2 Hz), 3.78–3.84(5H, m), 4.03(3H, s), 5.14(1H, br s), 6.82(1H, dd, J=7.9, 2.2 Hz), 6.98(1H, dd, J=2.2, 1.8 Hz),7.03(1H, dd, J=7.7, 1.8 Hz),7.07(1H, s), 7.14(1H, s), 7.30(1H, dd, J=7.9, 7.7 Hz).

m.p.; 197–199° C.

MASS 311 (MH$^+$)

PRODUCTION EXAMPLE 8

4-(3-Bromophenyl)-6,7-dimethoxy-2-methylaminoquinazoline

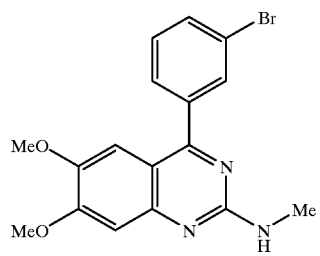

1.50 g of 4-(3-bromophenyl)-2-chloro-6,7-dimethoxyquinazoline obtained in Production Example 3 and 15 ml of 40% methylamine in methanol were suspended in a mixed solvent of 20 ml isopropanol and 20 ml tetrahydrofuran and stirred at 130° C. for 9 hours in a sealed tube. Ethyl acetate was added thereto, and the reaction solution was washed with water twice and then with brine and dried over anhydrous magnesium sulfate. The solvent was evaporated, and the crude product was purified and separated by silica gel column chromatography (ethyl acetate). The product was recrystallized from hexane-chloroform to give 1.39 g of the title compound as pale yellow crystals.

$^1$H-NMR (400 MHz, CDCl$_3$) δ; 3.11(3H, d, J=5.1 Hz), 3.83(3H, s), 4.03(3H, s), 5.15(1H, m), 7.01(1H, s), 7.07(1H, s), 7.41(1H, dd, J=7.9, 7.7 Hz), 7.62(1H, ddd, J=7.7, 1.4, 1.0 Hz), 7.65(1H, ddd, J=7.9, 2.0, 1.0 Hz), 7.86(1H, dd, J=2.0, 1.4 Hz).

m.p.; 246–248° C.

MASS 374, 376 (MH$^+$)

PRODUCTION EXAMPLE 9

1,2-Diethoxybenzene

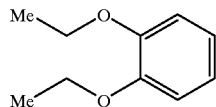

15.0 g of 2-ethoxyphenol, 18.0 ml of iodoethane and 30.0 g of potassium carbonate were suspended in 150 ml dimethylformamide, and the mixture was stirred at 80° C. for 30 hours. Ethyl acetate was added thereto, and the mixture was washed with water for five times and with brine, and then dried over anhydrous magnesium sulfate. The solvent was evaporated to give the title compound quantitatively as a red-brown oil.

$^1$H-NMR (400 MHz, CDCl$_3$) δ; 1.45(6H, t, J=7.0 Hz), 4.09(4H, q, J=7.0 Hz), 6.89(4H, s).

PRODUCTION EXAMPLE 10

4-(3-Bromobenzoyl)-1,2-diethoxybenzene

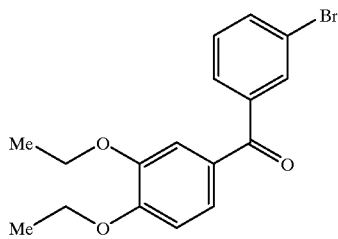

18.9 g of 1,2-diethoxybenzene obtained in Production Example 9 and 22.0 g of 3-bromobenzoyl chloride were dissolved in 100 ml dichloromethane, and 100 ml of 1.0 M tin tetrachloride in dichloromethane was added dropwise thereto under ice-cooling. After the dropwise addition, the mixture was further stirred at room temperature for 15 hours. The reaction solution was poured into ice-cold water to terminate the reaction, and the organic layer was recovered, washed with water twice and with brine, and then dried over anhydrous magnesium sulfate. The solvent was evaporated, and the crude product was recrystallized from hexane-ethyl acetate to give 23.8 g of the title compound as colorless crystals.

$^1$H-NMR (400 MHz, CDCl$_3$) δ; 1.46–1.52(6H, m), 4.13–4.21(4H, m), 6.89(1H, d, J=8.8 Hz), 7.32(1H, dd, J=8.8, 2.0 Hz), 7.35(1H, t, J=7.8 Hz), 7.46(1H, d, J=2.0 Hz), 7.64–7.71(2H, m), 7.88(1H, t, J=1.6 Hz).

PRODUCTION EXAMPLE 11

5-(3-Bromobenzoyl)-1,2-diethoxy-4-nitrobenzene

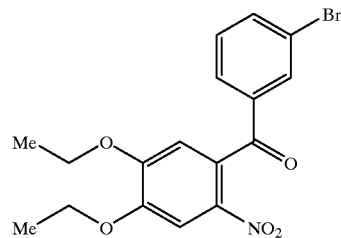

4-(3-Bromobenzoyl)-1,2-diethoxybenzene (20.7 g) obtained in Production Example 10 was dissolved in 80 ml of acetic anhydride, and then 4.5 ml of fuming nitric acid was added dropwise into the mixture under ice-cooling. After the dropwise addition, the mixture was further stirred 15 min under ice-cooling. The reaction mixture was poured into ice-cold water to cease the reaction, and then the resulting crystals were collected by filtration, washed with water and then air-dried to give 23.1 g of the title compound as yellow crystals.

$^1$H-NMR (400 MHz, CDCl$_3$) δ; 1.50(3H, t, J=7.2 Hz), 1.55(3H, t, J=7.2 Hz), 4.17(2H, q, J=7.2 Hz), 4.25(2H, q, J=7.2 Hz), 6.80(1H, s), 7.31(1H, t, J=8.0 Hz), 7.62(1H, ddd, J=8.0, 1.6, 1.2 Hz), 7.68(1H, ddd, J=8.0, 1.6, 1.2 Hz), 7.72(1H, s), 7.87(1H, t, J=1.6 Hz).

PRODUCTION EXAMPLE 12

4-Amino-5-(3-hromobenzoyl)-1,2-diethoxybenzene

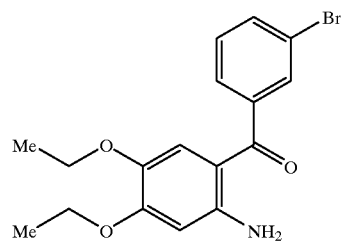

5-(3-Bromobenzoyl)-1,2-diethoxy-4-nitrobenzene (25.6 g) obtained in Production Example 11 and 16. 5 g of iron (powder) were suspended in a mixed solvent of 300 ml of ethanol and 75 ml of acetic acid, and the mixture was heated under reflux for 2 hours. The solvent was evaporated, and then the resulting residue was suspended in ethyl acetate and filtered. The filtrate was evaporated, and the crude product was purified and separated by silica gel column chromatography (hexane:ethyl acetate=1:1). The title compound was obtained quantitatively as yellow crystals.

$^1$H-NMR (400 MHz, CDCl$_3$) δ; 1.33(3H, t, J=7.2 Hz), 1.48(3H, t, J=7.2 Hz), 3.85(2H, q, J=7.2 Hz), 4.11(2H, q, J=7.2 Hz), 6.17(1H, s), 6.89(1H, s), 7.32(1H, t, J=8.0 Hz), 7.51(1H, ddd, J=8.0, 2.0, 1.2 Hz), 7.61(1H, ddd, J=8.0, 1.2, 0.8 Hz), 7.73(1H, dd, J=2.0, 0.8 Hz).

PRODUCTION EXAMPLE 13

4-(3-Bromophenyl)-6,7-diethoxy-2-quinazoline

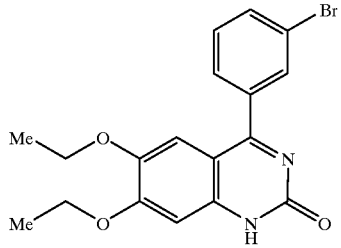

4-Amino-5-(3-bromobenzoyl)-1,2-diethoxybenzene (25.1 g) obtained in Production Example 12 and 50.0 g of urea were suspended in 15 ml of 1-methyl-2-pyrrolidinone, and the mixture was stirred at 200° C. for 1 hour. Water was added thereto, and the resulting crystals were collected by filtration, washed with water and then air-dried to give 23.2 g of the title compound as yellow crystals.

$^1$H-NMR (400 MHz, CDCl$_3$) δ; 1.29(3H, t, J=7.2 Hz), 1.41(3H, t, J=7.2 Hz), 3.91(2H, q, J=7.2 Hz), 4.15(2H, q, J=7.2 Hz), 5.47(1H, br s), 6.17(1H, s), 6.95(1H, s), 7.54(1H, t, J=8.0 Hz), 7.69(1H, dd, J=8.0, 1.6 Hz), 7.80(1H, dd, J=8.0, 1.6 Hz), 7.84(1H, t, J=1.6 Hz).

PRODUCTION EXAMPLE 14

4-(3-Bromophenyl)-2-chloro-6,7-diethoxyquinazoline

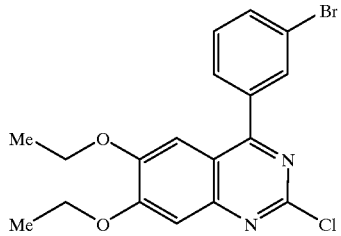

4-(3-Bromophenyl)-6,7-diethoxy-2-quinazoline (11.5 g) obtained in Production Example 13 was suspended in 90 ml of phosphorous oxychloride, and the mixture was heated under reflux for 1 hour. The solvent was evaporated, and the resulting residue was suspended in dimethylformamide and then poured into ice-cold water. The resulting crystals were collected by filtration, washed with water and then air-dried to give 11.8 g of the title compound as yellow crystals.

$^1$H-NMR (400 MHz, CDCl$_3$) δ; 1.50(3H, t, J=7.2 Hz), 1.57(3H, t, J=7.2 Hz), 4.09(2H, q, J=7.2 Hz), 4.29(2H, q, J=7.2 Hz), 7.21(1H, s), 7.31(1H, s), 7.44(1H, t, J=8.0 Hz), 7.66–7.72(2H, m), 7.92(1H, t, J=1.6 Hz).

PRODUCTION EXAMPLE 15

4-(3-Bromophenyl)-6,7-diethoxy-2-methylaminoquinazoline

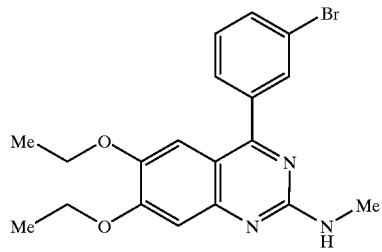

Starting from 12.0 g of 4-(3-bromophenyl)-2-chloro-6,7-diethoxyquinazoline obtained in Production Example 14 and 60 ml of 40% methylamine in methanol, 10.7 g of the title compound was obtained as yellow crystals in the same manner as in Production Example 8.

m.p.; 130–132° C.

MASS 402, 404 (MH$^+$)

$^1$H-NMR (400 MHz, CDCl$_3$) δ; 1.44(3H, t, J=7.2 Hz), 1.54(3H, t, J=7.2 Hz), 3.11(3H, d, J=5.2 Hz), 4.00(2H, q, J=7.2 Hz), 4.25(2H, q, J=7.2 Hz), 5.12(1H, br s), 7.02(1H, s), 7.04(1H, s), 7.40(1H, t, J=8.0 Hz), 7.60(1H, ddd, J=8.0, 1.6, 1.2), 7.64(1H, ddd, J=8.0, 1.6, 1.2), 7.84(1H, t, J=1.6 Hz).

PRODUCTION EXAMPLE 16

2-Chloro-6,7-dimethoxy-4-(3-formylphenyl)quinazoline

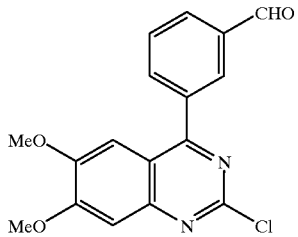

Starting from 3.00 g of 3,4-dichloro-6,7-dimethoxyquinazoline and 2.47 g of 3-formylphenyl boric acid, 3.50 g of the title compound was obtained as colorless crystals in the same manner as in Production Example 1.

$^1$H-NMR (400 MHz, CDCl$_3$) δ; 3.90(3H, s), 4.08(3H, s), 7.23(1H, s), 7.37(1H, s), 7.78(1H, t, J=7.6 Hz), 8.07(1H, dt, J=7.6, 1.4 Hz), 8.10(1H, dt, J=7.6, 1.4 Hz), 8.32(1H, t, J=1.4 Hz), 10.15(1H, s).

PRODUCTION EXAMPLE 17

2-Chloro-4-(3-chloroformylphenyl)-6,7-dimethoxyquinazoline

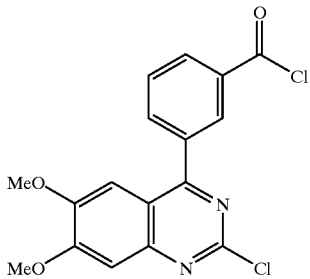

657 mg of 2-chloro-6,7-dimethoxy-4-(3-formylphenyl) quinazoline obtained in Production Example 16 was converted into a carboxylic acid compound by use of Jones reagent and then reacted with thionyl chloride in a usual manner to give 620 mg of the title compound as pale yellow crystals.

$^1$H-NMR (400 MHz, CDCl$_3$) δ; 3.92(3H, s), 4.09(3H, s), 7.21(1H, s), 7.39(1H, s), 7.77(1H, t, J=8.0 Hz), 8.15(1H, d, J=8.0 Hz), 8.32(1H, d, J=8.0 Hz), 8.56(1H, m).

PRODUCTION EXAMPLE 18

6,7-Dimethoxy-4-(3-formylphenyl)-2-methylaminoquinazoline

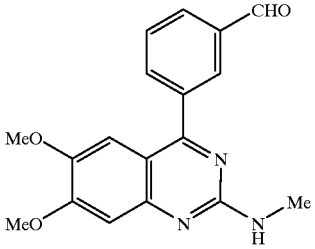

Starting from 1.50 g of 2-chloro-6,7-dimethoxy-4-(3-formylphenyl)quinazoline and 15 ml of 40% methylamine in methanol, 1.00 g of the title compound was obtained as yellow crystals in the same manner as in Production Example 8.

$^1$H-NMR (400 MHz, CDCl$_3$) δ; 3.14(3H, d, J=4.8 Hz), 3.80(3H, s), 4.04(3H, s), 5.13(1H, br s), 6.99(1H, s), 7.09 (1H, s), 7.72(1H, t, J=7.6 Hz), 7.98(1H, dt, J=7.6, 1.4 Hz), 8.05(1H, dt, J=7.6, 1.4 Hz), 8.24(1H, t, J=1.4 Hz), 10.13(1H, s).

PRODUCTION EXAMPLE 19

6-Benzyloxy-2,4-dichloro-7-methoxyquinazoline

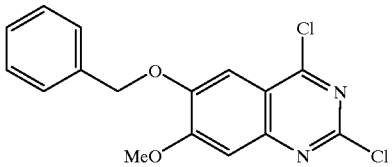

3.16 g of 6-benzyloxy-7-methoxy-2,4-quinazolindione obtained by esterifying 5-benzyloxy-4-methoxy-2-nitrobenzoic acid in a usual manner, then reducing its nitro group and cyclizing it with urea, and 10 ml N,N-diisopropyl ethylamine were suspended in 90 ml phosphorus oxychloride, and the mixture was heated under reflux for 1 hour. The solvent was evaporated, and then ethyl acetate was added to the resulting residue which was then washed with water 5 times and with brine and dried over anhydrous magnesium sulfate. The solvent was evaporated, whereby the title compound was obtained quantitatively as yellow crystals.

$^1$H-NMR (400 MHz, CDCl$_3$) δ; 4.05(3H, s), 5.31(2H, s), 7.29(1H, s), 7.34–7.45(4H, m), 7.49–7.52(2H, m).

PRODUCTION EXAMPLE 20

2-Amino-4-(3-bromophenyl)-6,7-dimethoxyquinazoline

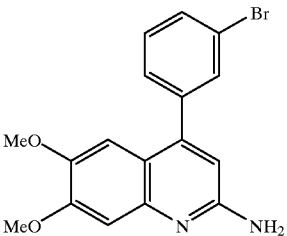

3.66 g of 5-(3-bromobenzoyl)-1,2-dimethoxy-4-nitrobenzene, which was obtained from 1,2-dimethoxybenzene through the processes in Production Example 10 and then in Production Example 11 was subjected in a usual manner to Wittig-Horner reaction with diethyl cyanomethyl phosphonate, and the resulting crude product and 2.23 g iron were suspended in 40 ml methanol, and 20 ml conc. hydrochloric acid was added dropwise thereinto. After the dropwise addition, the mixture was heated under reflux for 8 hours. The solvent was evaporated, then water was added to the residue, and the resulting crystals were collected by filtration. The crystals were returned to the free compound, and purified and separated by silica gel column chromatography (hexane:ethyl acetate= 1:3) to give 950 mg of the title compound as colorless crystals.

$^1$H-NMR (400 MHz, CDCl$_3$) δ; 3.80(3H, s), 4.01(3H, s), 4.59(2H, m), 6.53(1H, s), 6.93(1H, s), 7.15(1H, s), 7.36–7.44(2H, m), 7.61(1H, m), 7.65(1H, dd, J=2.0, 0.4 Hz).

EXAMPLE 1

4-(3-Benzoylaminophenyl)-6,7-dimethoxy-2-methylaminoquinazoline

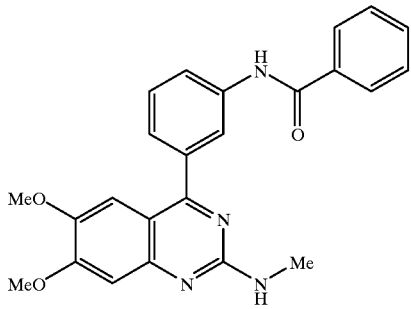

310 mg of 4-(3-aminophenyl)-6,7-dimethoxy-2-methylaminoquinazoline obtained in Production Example 7, 155 mg benzoyl chloride and 119 mg pyridine were suspended in 20 ml tetrahydrofuran, and the mixture was stirred at room temperature for 30 minutes. After ethyl acetate was added thereto, it was washed with saturated aqueous sodium bicarbonate thrice and with brine, and then dried over anhydrous magnesium sulfate. The solvent was evaporated, and the crude product was purified and separated by silica gel column chromatography (hexane:ethyl acetate=1:3). The product was recrystallized from hexane-ethyl acetate to give 343 mg of the title compound as yellow crystals.

$^1$H-NMR (400 MHz, CDCl$_3$) δ; 3.12(3H, d, J=4.9 Hz), 3.88(3H, s), 4.03(3H, s), 5.12(1H, m), 7.07(1H, s), 7.22(1H, s), 7.48–7.59 (5H, m), 7.79(1H, ddd, J=7.7, 2.0, 1.6 Hz), 7.86–7.91(2H, m), 7.96(1H, br s), 8.00(1H, dd, J=2.0, 1.4 Hz).

m.p.; 201–203° C.

MASS 415 (MH$^+$)

EXAMPLE 2

6,7-Dimethoxy-2-methylamino-4-[3-(4-pyridine carbonylamino)phenyl]quinazoline

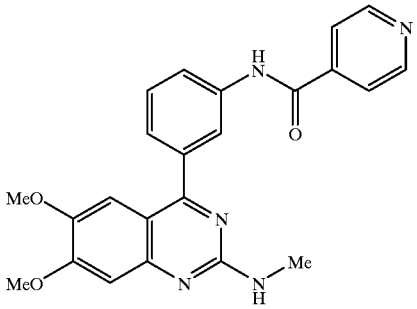

Starting from 196 mg of isonicotinoyl chloride, 220 mg of the title compound was obtained as pale yellow crystals in the same manner as in Example 1.

$^1$H-NMR (400 MHz, CDCl$_3$) δ; 3.11(3H, d, J=4.9 Hz), 3.86(3H, s), 4.02(3H, s), 5.13(1H, m), 7.07(1H, s), 7.19(1H, s), 7.52–7.58 (2H, m), 7.71 (2H, dd, J=4.4, 1.7 Hz), 7.77(1H, ddd, J=6.7, 2.2, 1.5 Hz), 8.00(1H, dd, J=1.5, 1.0 Hz), 8.11(1H, br s), 8.79(2H, dd, J=4.4, 1.7 Hz).

m.p.; 228–230° C.

MASS 416 (MH$^+$)

EXAMPLE 3

6,7-Dimethoxy-2-methylamino-4-[3-(2-pyridinecarbonylamino)phenyl]quinazoline

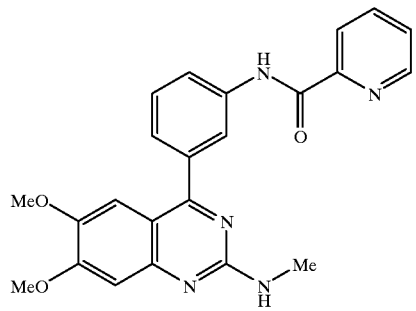

Starting from 196 mg of picolinoyl chloride, 298 mg of the title compound was obtained as pale yellow crystals in the same manner as in Example 1.

$^1$H-NMR (400 MHz, CDCl$_3$) δ; 3.13(3H, d, J=5.0 Hz), 3.86(3H, s), 4.03(3H, s), 5.16(1H, m), 7.08(1H, s), 7.22(1H, s), 7.47–7.53 (2H, m), 7.56(1H, dd, J=8.0, 7.7 Hz), 7.88–7.94(2H, m), 8.16(1H, dd, J=2.0, 1.4 Hz), 8.30(1H, ddd, J=7.9, 1.3, 0.9 Hz), 8.62(1H, ddd, J=4.4, 1.6, 0.9 Hz), 10.16(1H, br s).

m.p.; 175–177° C.

MASS 416 (MH$^+$)

EXAMPLE 4:

6,7-Dimethoxy-2-methylamino-4-[3-(3-pyridinecarbonylamino)phenyl]quinazoline

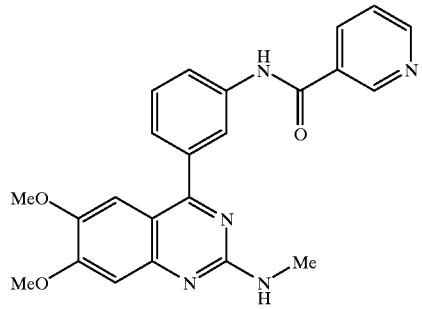

Starting from 196 mg of picolinoyl chloride, 263 mg of the title compound was obtained as yellow crystals in the same manner as in Example 1.

$^1$H-NMR (400 MHz, CDCl$_3$) δ; 2.91(3H, d, J=4.6 Hz), 3.76(3H, s), 3.93(3H, s), 6.97–7.05(2H, m), 7.18(1H, s), 7.47–7.62(3H, m), 7.90(1H, ddd, J=7.2, 2.2, 0.7 Hz), 8.21 (1H, dd, J=2.2, 1.4 Hz), 8.32(1H, ddd,7.7, 2.2, 1.6 Hz), 8.78(1H, dd, J=4.7, 2.2 Hz), 9.13(1H, d, J=1.6 Hz), 10.63 (1H, br s).

m.p.; 251–253° C.

MASS 416 (MH$^+$)

EXAMPLE 5

6,7-Dimethoxy-2-methylamino-4-[3-(3,4-methylenedioxybenzoylamino)phenyl]quinazoline

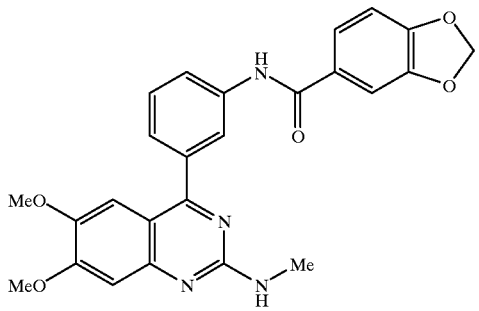

Starting from 369 mg of piperonyloyl chloride, 466 mg of the title compound was obtained as yellow crystals in the same manner as in Example 1.

$^1$H-NMR (400 MHz, CDCl$_3$) δ; 3.12(3H, d, J=4.9 Hz), 3.87(3H, s), 4.03(3H, s), 5.12(1H, m), 6.06(2H, s), 6.88(1H, d, J=8.0 Hz), 7.07(1H, s), 7.21(1H, s), 7.37(1H, d, J=1.8 Hz), 7.41(1H, dd, J=8.0, 1.8 Hz), 7.48(1H, ddd, J=7.8, 1.4, 1.2 Hz), 7.53(1H, dd, J=8.0, 7.8 Hz), 7.75(1H, ddd, J=8.0, 2.0, 1.2 Hz), 7.83(1H, br s), 7.97(1H, dd, J=2.0, 1.4 Hz).

m.p.; 205–207° C.

MASS 459 (MH$^+$)

EXAMPLE 6

6,7-Dimethoxy-2-methylamino-4-[3-(phenylacetylamino)phenyl]quinazoline

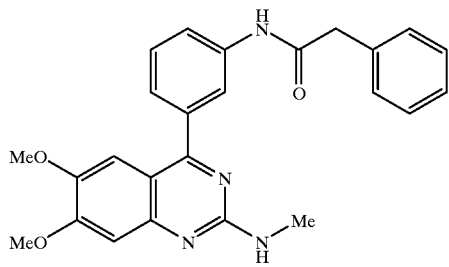

Starting from 155 mg of 4-(3-aminophenyl)-6,7-dimethoxy-2-methylaminoquinazoline obtained in Production Example 7 and 154 mg of phenyacetyl chloride, 184 mg of the title compound was obtained as pale yellow crystals in the same manner as in Example 1.

$^1$H-NMR (400 MHz, CDCl$_3$) δ; 3.09(3H, d, J=5.1 Hz), 3.76(2H, s), 3.82(3H, s), 4.02(3H, s), 5.11(1H, m), 7.05(1H, s), 7.11(1H, s), 7.21(1H, br s), 7.30–7.47(7H, m), 7.60–7.68 (2H, m).

m.p.; 175–177° C.

MASS 429 (MH$^+$)

EXAMPLE 7

6,7-Dimethoxy-2-methylamino-4-[3-(3-phenylpropanoylamino)phenyl]quinazoline

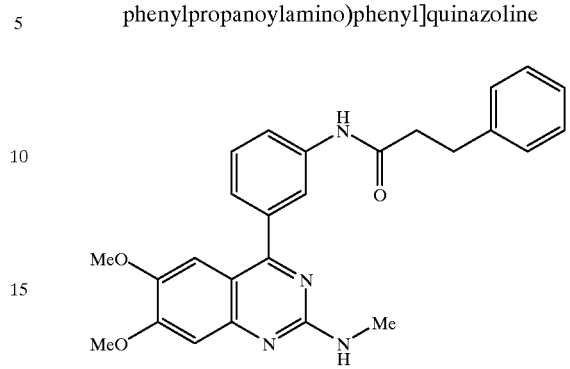

Starting from 169 mg of 3-phenylpropanoyl chloride, 176 mg of the title compound was obtained as pale yellow crystals in the same manner as in Example 6.

$^1$H-NMR (400 MHz, CDCl$_3$) δ; 2.68(2H, t, J=7.5 Hz), 3.06(2H, t, J=7.5 Hz), 3.11(3H, d, J=4.9 Hz), 3.85(3H, s), 4.03(3H, s), 5.11(1H, m), 7.06(1H, s), 7.12–7.32(7H, m), 7.42–7.48 (2H, m), 7.54(1H, ddd, J=7.5, 5.4, 0.4 Hz), 7.81(1H, dd, J=0.8, 0.4 Hz).

m.p.; 180–182° C.

MASS 443 (MH$^+$)

EXAMPLE 8

4-[3-(2-Chlorobenzoylamino)phenyl]-6,7-dimethoxy-2-methylaminoquinazoline

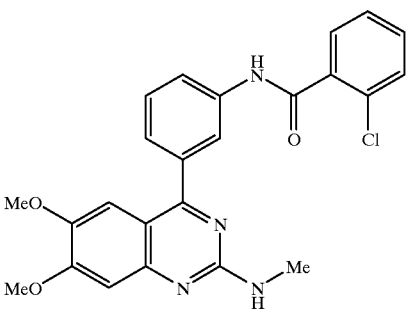

Starting from 175 mg of 2-chlorobenzoyl chloride, 200 mg of the title compound was obtained as pale yellow crystals in the same manner as in Example 6.

$^1$H-NMR (400 MHz, CDCl$_3$) δ; 3.12(3H, d, J=4.9 Hz), 3.87(3H, s), 4.03(3H, s), 5.16(1H, m), 7.08(1H, s), 7.22(1H, s), 7.36–7.48 (3H, m), 7.50–7.58(2H, m), 7.75–7.80(2H, m), 8.02(1H, br s) 8.05(1H, dd, J=0.8, 0.4 Hz).

m.p.; 197–199° C.

MASS 449 (MH$^+$)

EXAMPLE 9

4-[3-(3-Chlorobenzoylamino)phenyl]-6,7-dimethoxy-2-methylaminoquinazoline

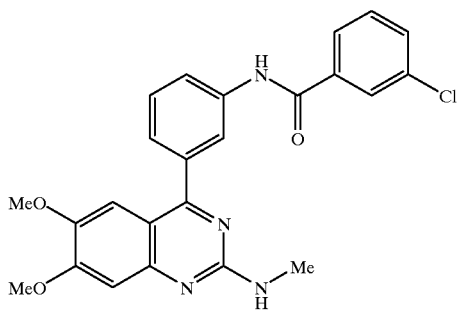

Starting from 175 mg of 3-chlorobenzoyl chloride, 200 mg of the title compound was obtained as pale yellow crystals in the same manner as in Example 6.

$^1$H-NMR (400 MHz, CDCl$_3$) δ; 3.12(3H, d, J=4.7 Hz), 3.87(3H, s), 4.03(3H, s), 5.49(1H, m), 7.08(1H, s), 7.21(1H, s), 7.43(1H, dd, J=8.0, 7.6 Hz), 7.50–7.57(3H, m), 7.72–7.78 (2H, m), 7.87(1H, dd, J=2.0, 1.6 Hz), 7.97–8.02(2H, m).

m.p.; 124–126° C.

MASS 449 (MH$^+$)

EXAMPLE 10

4-[3-(4-Chlorobenzoylamino)phenyl]-6,7-dimethoxy-2-methylaminoquinazoline

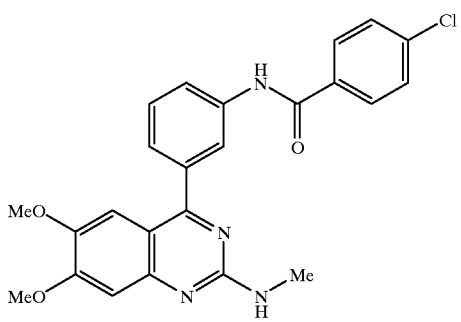

Starting from 175 mg of 4-chlorobenzoyl chloride, 217 mg of the title compound was obtained as yellow crystals in the same manner as in Example 6.

$^1$H-NMR (400 MHz, CDCl$_3$) δ; 3.11(3H, d, J=4.7 Hz), 3.87(3H, s), 4.03(3H, s), 5.74(1H, m), 7.07(1H, s), 7.20(1H, s), 7.43–7.47 (2H, m), 7.48–7.55(2H, m), 7.75(1H, ddd, J=7.2, 2.2, 1.8 Hz), 7.80–7.84(2H, m), 8.04(1H, br s) 8.07(1H, dd, J=1.8, 1.4 Hz).

m.p.; 193–195° C.

MASS 449 (MH$^+$)

EXAMPLE 11

6,7-Dimethoxy-4-[3-(2-methoxybenzoylamino)phenyl]-2-methylaminoquinazoline

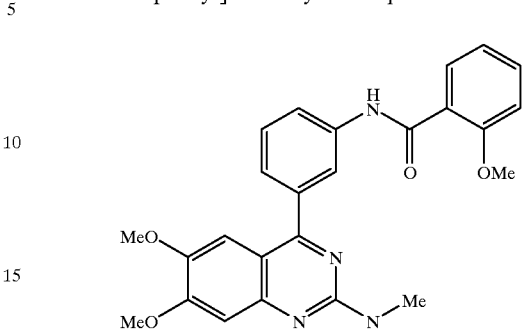

Starting from 171 mg of 2-methoxybenzoyl chloride, 178 mg of the title compound was obtained as pale yellow crystals in the same manner as in Example 6.

$^1$H-NMR (400 MHz, CDCl$_3$) δ; 3.12(3H, d, J=5.0 Hz), 3.87(3H, s), 4.03(3H, s), 4.06(3H, s), 5.17(1H, m), 7.05(1H, dd, J=8.2, 0.8 Hz), 7.08(1H, s), 7.15(1H, ddd, J=8.0, 7.2, 0.8 Hz), 7.22(1H, s), 7.44–7.55 (3H, m), 7.86(1H, ddd, J=7.9, 2.0, 1.2 Hz), 7.98(1H, dd, J=2.0, 1.8 Hz), 8.29(1H, dd, J=8.0, 1.8 Hz), 9.92(1H, br s).

m.p.; 194–196° C.

MASS 445 (MH$^+$)

EXAMPLE 12

6,7-Dimethoxy-4-[3-(3-methoxybenzoylamino)phenyl]-2-methylaminoquinazoline

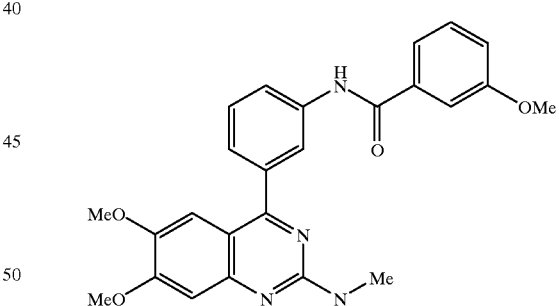

Starting from 171 mg of 3-methoxybenzoyl chloride, 187 mg of the title compound was obtained as pale yellow crystals in the same manner as in Example 6.

$^1$H-NMR (400 MHz, CDCl$_3$) δ; 3.12(3H, d, J=4.7 Hz), 3.87(3H, s), 3.88(3H, s), 4.03(3H, s), 5.24(1H, m), 7.06–7.12(2H, m), 7.22(1H, s), 7.38–7.42(2H, m), 7.45(1H, dd, J=1.8, 1.4 Hz), 7.50(1H, ddd, J=7.7, 1.4, 1.4 Hz), 7.54(1H, dd, J=7.9, 7.7 Hz), 7.79(1H, ddd, J=7.9, 1.8, 1.4 Hz), 7.95(1H, br s), 8.00(1H, dd, J=1.8, 1.4 Hz).

m.p.; 193–195° C.

MASS 445 (MH$^+$)

EXAMPLE 13

6,7-Dimethoxy-4-[3-(4-methoxyphenzoylamino)phenyl]-2-methylaminoquinazoline

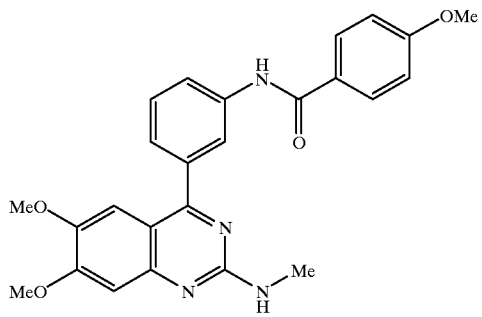

Starting from 171 mg of 4-methoxybenzoyl chloride, 178 mg of the title compound was obtained as pale yellow crystals in the same manner as in Example 6.

$^{1}$H-NMR (400 MHz, CDCl$_3$) δ; 3.11(3H, d, J=5.0 Hz), 3.87(3H, s), 3.88(3H, s), 4.02(3H, s), 5.14(1H, m), 6.95–7.00(2H, m), 7.07(1H, s), 7.22(1H, s), 7.48(1H, ddd, J=7.7, 1.4, 1.4 Hz), 7.53(1H, dd, J=7.9, 7.7 Hz), 7.78(1H, ddd, J=7.9, 2.0, 1.4 Hz), 7.83–7.88(2H, m), 7.90(1H, brs), 7.97(1H, dd, J=2.0, 1.4 Hz).

m.p.; 219–221° C.

MASS 445 (MH$^+$)

EXAMPLE 14

6,7-Dimethoxy-4-[3-(3,4-dimethoxybenzoylamino)phenyl]-2-methylaminoquinazoline

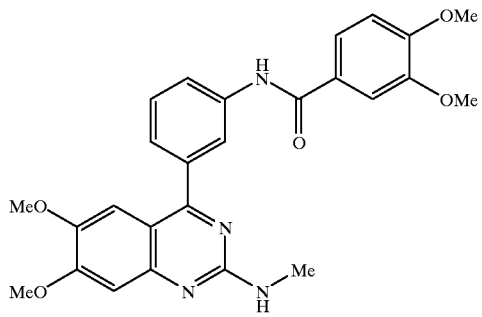

Starting from 171 mg of 4-methoxybenzoyl chloride, 178 mg of the title compound was obtained as pale yellow crystals in the same manner as in Example 6.

$^{1}$H-NMR (400 MHz, CDCl$_3$) δ; 3.12(3H, d, J=4.9 Hz), 3.87(3H, s), 3.95(3H, s), 3.96(3H, s), 4.03(3H, s), 5.15(1H, m), 6.92(1H, d, J=8.4 Hz), 7.07(1H, s), 7.21(1H, s), 7.41(1H, dd, J=8.4, 2.0 Hz), 7.46–7.51(2H, m), 7.54(1H, dd, J=7.9, 7.7 Hz), 7.82(1H, ddd, J=7.9, 2.0, 1.4 Hz), 7.92(1H, br s), 7.96(1H, dd, J=2.0, 1.4 Hz).

m.p.; 128–130° C.

MASS 475 (MH$^+$)

EXAMPLE 15

4-[3-(3,4-Dichlorobenzoylamino)phenyl]-6,7-dimethoxy-2-methylaminoquinazoline

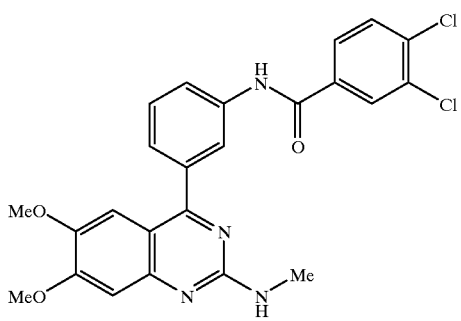

Starting from 210 mg of 3,4-dichlorobenzoyl chloride, 183 mg of the title compound was obtained as pale yellow crystals in the same manner as in Example 6.

$^{1}$H-NMR (400 MHz, CDCl$_3$) δ; 3.12(3H, d, J=5.0 Hz), 3.87(3H, s), 4.04(3H, s), 5.68(1H, m), 7.08(1H, s), 7.21(1H, s), 7.51–7.59 (3H, m), 7.70(1H, dd, J=8.4, 2.1 Hz), 7.74(1H, ddd, J=7.9, 2.0, 1.4 Hz), 7.96–8.02(3H, m).

m.p.; 134–136° C.

MASS 483 (MH$^+$)

EXAMPLE 16

4-(3-Cyclopropanoylaminophenyl)-6,7-dimethoxy-2-methylaminoquinazoline

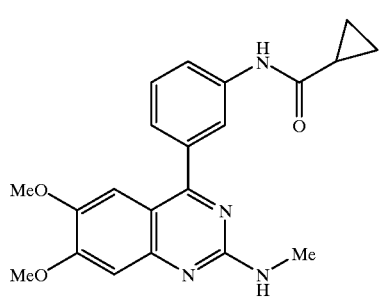

Starting from 105 mg of cyclopropanecarbonyl chloride, 152 mg of the title compound was obtained as pale yellow crystals in the same manner as in Example 6.

$^{1}$H-NMR (400 MHz, CDCl$_3$) δ; 0.84–0.90(2H, m), 1.08–1.12(2H, m), 1.48–1.55(1H, m), 3.11(3H, d, J=4.9 Hz), 3.83(3H, s), 4.02(3H, s), 5.12(1H, m), 7.06(1H, s), 7.16(1H, s), 7.40–7.53(3H, m), 7.65(1H, ddd, J=7.9, 2.0, 1.4 Hz), 7.86(1H, dd, J=2.0, 1.4 Hz).

m.p.; 205–207° C.

MASS 379 (MH$^+$)

EXAMPLE 17

4-[3-(3-Cyclopentyloxy-4-methoxybenzoylamino)phenyl]-6,7-dimethoxy-2-methylaminoquinazoline

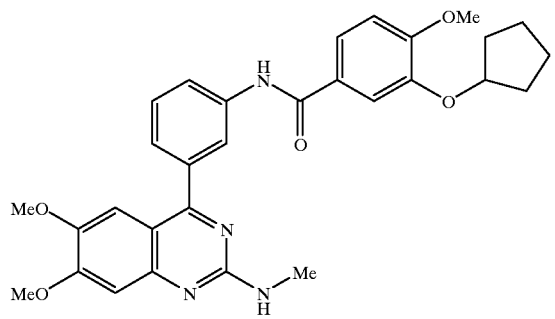

Starting from 255 mg of 3-cyclopentyloxy-4-methoxybenzoyl chloride, 202 mg of the title compound was obtained as pale yellow crystals in the same manner as in Example 6.

$^1$H-NMR (400 MHz, CDCl$_3$) δ; 1.57–1.67(2H, m), 1.80–2.05(6H, m), 3.12(3H, d, J=5.0 Hz), 3.87(3H, s), 3.91(3H, s), 4.03(3H, s), 4.88(1H, m), 5.15(1H, m), 6.90 (1H, d, J=8.4 Hz), 7.07(1H, s), 7.21(1H, s), 7.38(1H, dd, J=8.4, 2.2 Hz), 7.46–7.50(2H, m), 7.53(1H, dd, J=7.9, 7.7 Hz), 7.80(1H, ddd, J=7.9, 2.0, 1.4 Hz), 7.90(1H, br s), 7.96(1H, dd, J=2.0, 1.4 Hz).

m.p.; 129–131° C.

MASS 529 (MH$^+$)

EXAMPLE 18

4-[3-(3-Chloro-4-methoxybenzoylamino)phenyl]-6,7-dimethoxy-2-methylaminoquinazoline

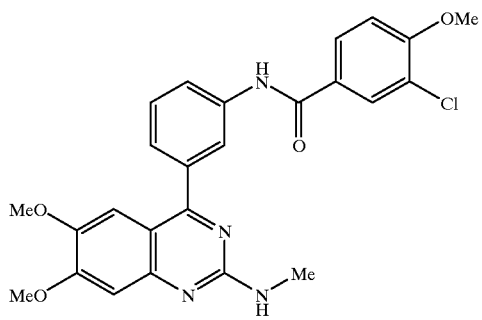

Starting from 205 mg of 3-chloro-4-methoxybenzoyl chloride, 152 mg of the title compound was obtained as pale yellow crystals in the same manner as in Example 6.

$^1$H-NMR (400 MHz, CDCl$_3$) δ; 3.11(3H, d, J=4.7 Hz), 3.87(3H, s), 3.97(3H, s), 4.03(3H, s), 5.32(1H, m), 6.99(1H, d, J=8.6 Hz), 7.07(1H, s), 7.21(1H, s), 7.48–7.56(2H, m), 7.74–7.85(2H, m), 7.90–7.93(2H, m), 7.98(1H, dd, J=2.0, 1.4 Hz).

m.p.; 130–132° C.

MASS 479 (MH$^+$)

EXAMPLE 19

6,7-Dimethoxy-4-methylamino-4-[3-(3,4,5-trimethoxybenzoylamino)phenyl]quinazoline

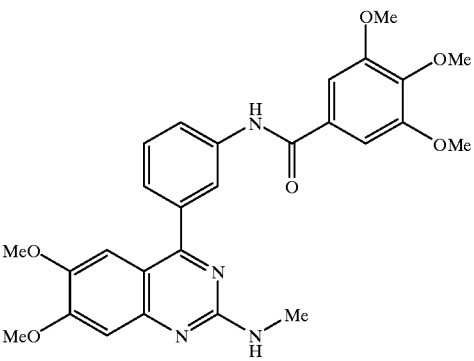

Starting from 231 mg of 3,4,5-trimethoxybenzoyl chloride, 173 mg of the title compound was obtained as pale yellow crystals in the same manner as in Example 6.

$^1$H-NMR (400 MHz, CDCl$_3$) δ; 3.11(3H, d, J=4.8 Hz), 3.86(3H, s), 3.91(3H, s), 3.93(6H, s), 4.03(3H, s), 5.24(1H, m), 7.08(1H, s), 7.09(2H, s), 7.22(1H, s), 7.49(1H, ddd, J=7.7, 1.4, 1.4 Hz), 7.55(1H, dd, J=7.9, 7.7 Hz), 7.83(1H, ddd, J=7.9, 2.0, 1.4 Hz), 7.90–7.94(2H, m).

m.p.; 122–124° C.

MASS 505 (MH$^+$)

EXAMPLE 20

4-[3-(4-Benzyloxybenzoylamino)phenyl]-6,7-dimethoxy-2-methylaminoquinazoline

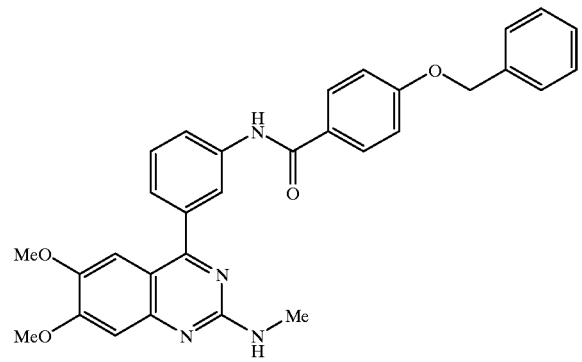

Starting from 4-benzyloxybenzoyl chloride, 516 mg of the title compound was obtained as pale yellow crystals in the same manner as in Example 1.

$^1$H-NMR (400 MHz, CDCl$_3$) δ; 3.12(3H, d, J=4.8 Hz), 3.88(3H, s), 4.03(3H, s), 5.12–5.16(3H, m), 7.04–7.09(3H, m), 7.23(1H, s), 7.32–7.46(5H, m), 7.49(1H, ddd, J=7.6, 1.4, 1.4 Hz), 7.54(1H, dd, J=7.8, 7.6 Hz), 7.77(1H, ddd, J=7.8, 1.8, 1.4 Hz), 7.83–7.88(3H, m), 7.98(1H, dd, J=1.8, 1.4 Hz).

m.p.; 110–112° C.

MASS 521 (MH$^+$)

EXAMPLE 21

6,7-Dimethoxy-4-[3-(4-hydroxybenzoylamino)phenyl]-2-methylaminoquinazoline

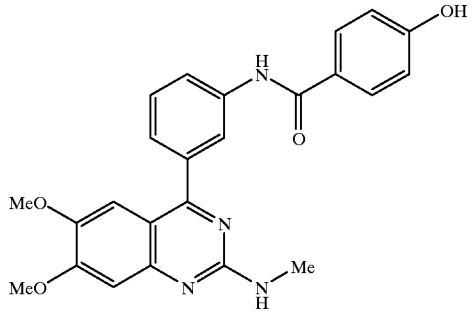

388 mg of 4-[3-(4-benzyloxybenzoylamino)phenyl]-6,7-dimethoxy-2-methylaminoquinazoline obtained in Example 20 and 200 mg of 10% palladium-carbon powder (hydrate) were suspended in a mixed solvent of 10 ml ethyl acetate and 10 ml tetrahydrofuran. After the atmosphere was replaced with hydrogen, the mixture was stirred for 3 days at ordinary pressure at room temperature. The reaction solution was filtered, and the filtrate was evaporated. Then, the crude product was recrystallized from hexane-ethyl acetate to give 278 mg of the title compound as pale yellow crystals.

$^1$H-NMR (400 MHz, CDCl$_3$) δ; 3.12(3H, d, J=4.8 Hz), 3.85(3H, s), 4.02(3H, s), 5.19(1H, m), 6.82–6.90(2H, m), 7.08(1H, s), 7.18(1H, s), 7.43–7.54(2H, m), 7.69–7.84(4H, m), 7.98(1H, dd, J=0.8, 0.4 Hz).

m.p.; 178–180° C.

MASS 431 (MH$^+$)

EXAMPLE 22

4-[3-(3-Benzyloxybenzoylamino)phenyl]-6,7-dimethoxy-2-methylaminoquinazoline

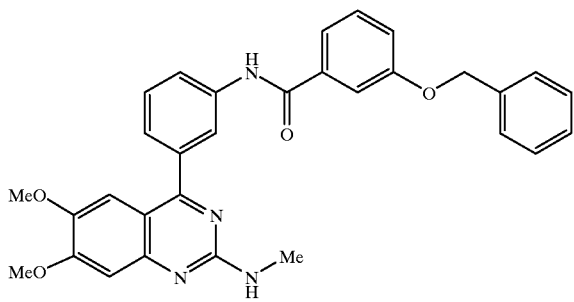

Starting from 3-benzyloxybenzoyl chloride, 518 mg of the title compound was obtained as pale yellow crystals in the same manner as in Example 1.

m.p.; 110–112° C.

MASS 521 (MH$^+$)

$^1$H-NMR (400 MHz, CDCl$_3$) δ; 3.13(3H, d, J=4.8 Hz), 3.87(3H, s), 4.03(3H, s), 5.14(2H, s), 5.31(1H, m), 7.08(1H, s), 7.17(1H, ddd, J=6.5, 2.8, 2.2 Hz), 7.22(1H, s), 7.30–7.47 (7H, m), 7.49–7.57(3H, m), 7.77(1H, ddd, J=8.0, 2.0, 1.2 Hz), 7.91(1H, br s), 8.01(1H, dd, J=2.0, 1.4 Hz).

EXAMPLE 23

6,7-Dimethoxy-4-[3-(3-hydroxybenzoylamino)phenyl]-2-methylaminoquinazoline

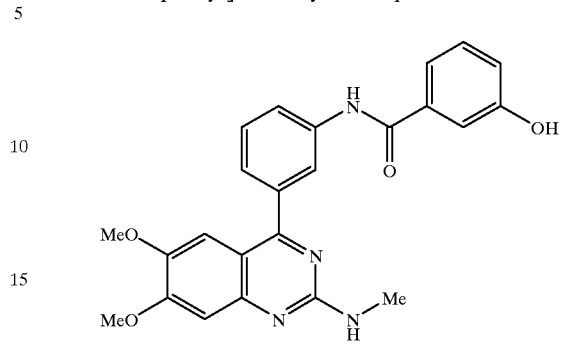

Starting from 448 mg of 4-[3-(3-benzyloxybenzoylamino)phenyl]-6,7-dimethoxy-2-methylaminoquinazoline obtained in Example 22, 220 mg of the title compound was obtained as colorless crystals in the same manner as in Example 21.

$^1$H-NMR (400 MHz, CDCl$_3$) δ; 2.90(3H, d, J=4.8 Hz), 3.76(3H, s), 3.93(3H, s), 6.96–7.03(3H, m), 7.19(1H, s), 7.39–7.46(4H, m), 7.54(1H, dd, J=8.2, 7.6 Hz), 7.87(1H, ddd, J=8.2, 2.0, 1.2 Hz), 7.54(1H, dd, J=2.0, 1.6 Hz), 9.76(1H, s), 10.37(1H, s).

m.p.; 265–267° C.

MASS 431 (MH$^+$)

EXAMPLE 24

4-[3-(2-Benzyloxybenzoylamino)phenyl]-6,7-dimethoxy-2-methylaminoquinazoline

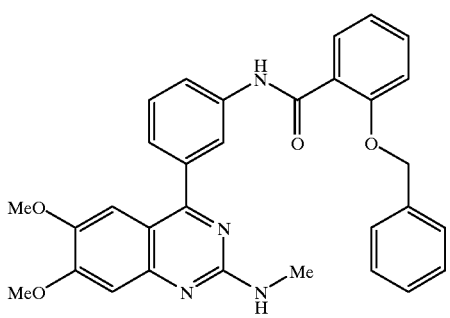

Starting from 2-benzyloxybenzoyl chloride, 500 mg of the title compound was obtained as pale yellow crystals in the same manner as in Example 1.

$^1$H-NMR (400 MHz, CDCl$_3$) δ; 3.15(3H, d, J=4.8 Hz), 3.79(3H, s), 4.06(3H, s), 5.13(1H, m), 5.21(2H, s), 7.03–7.09(2H, m), 7.11(1H, s), 7.13–7.21(2H, m), 7.23–7.31(3H, m), 7.35(1H, ddd, J=7.7, 1.4, 1.4 Hz), 7.39 (1H, dd, J=7.9, 7.7 Hz), 7.46–7.49(2H, m), 7.53(1H, ddd, J=8.2, 2.4, 1.8 Hz), 7.53(1H, ddd, J=7.9, 1.4, 1.8 Hz), 8.34(1H, dd, J=7.8, 1.8 Hz), 10.15(1H, br s).

m.p.; 192–194° C.

MASS 521 (MH$^+$)

EXAMPLE 25

6,7-Dimethoxy-4-[3-(2-hydroxybenzoylamino)phenyl]-2-methylaminoquinazoline

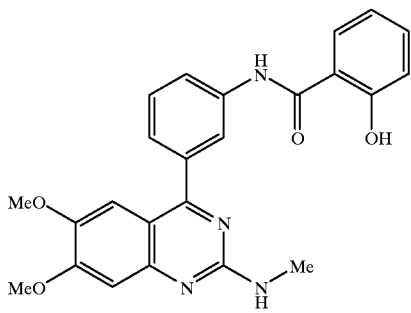

Starting from 388 mg of 4-[3-(2-benzyloxybenzoylamino)phenyl]-6,7-dimethoxy-2-methylaminoquinazoline obtained in Example 24, 278 mg of the title compound was obtained as pale yellow crystals in the same manner as in Example 21.

$^1$H-NMR (400 MHz, CDCl$_3$) δ; 2.91(3H, d, J=4.7 Hz), 3.75(3H, s), 3.93(3H, s), 6.95–7.08(4H, m), 7.18(1H, s), 7.42–7.53(2H, m), 7.57(1H, dd, J=8.0, 7.6 Hz), 7.81(1H, ddd, J=8.0, 2.0, 1.2 Hz), 7.96(1H, dd, J=8.0, 1.6 Hz), 8.17(1H, dd, J=2.0, 1.6 Hz), 10.57(1H, s), 11.72(1H, br s).

m.p.; 212–214° C.

MASS 431 (MH$^+$)

EXAMPLE 26

6,7-Dimethoxy-2-methylamino-4-[3-(4-methylthiobenzoylamino)phenyl]quinazoline

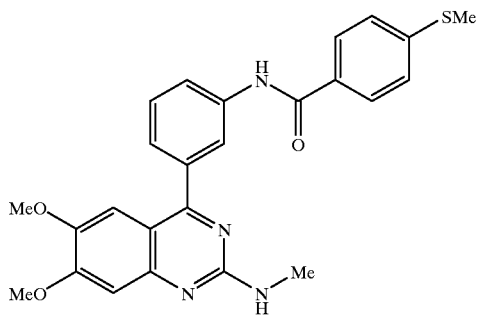

Starting from 930 mg of 4-(3-aminophenyl)-6,7-dimethoxy-2-methylaminoquinazoline obtained in Production Example 7 and 4-methylthiobenzoyl chloride, 1.23 g of the title compound was obtained as pale yellow crystals in the same manner as in Example 1.

$^1$H-NMR (400 MHz, CDCl$_3$) δ; 2.53(3H, s), 3.12(3H, d, J=5.0 Hz), 3.87(3H, s), 4.03(3H, s), 5.12(1H, m), 7.07(1H, s), 7.22(1H, s), 7.30–7.34(2H, m), 7.49(1H, ddd, J=7.7, 1.4, 1.0 Hz), 7.54(1H, dd, J=7.9, 7.7 Hz), 7.76–7.82(3H, m), 7.90(1H, br s), 7.98(1H, dd, J=1.8, 1.4 Hz).

m.p.; 209–211° C.

MASS 461 (MH$^+$)

EXAMPLE 27

6,7-Dimethoxy-2-methylamino-4-[3-(4-methylsulfinylbenzoylamino)phenyl]quinazoline

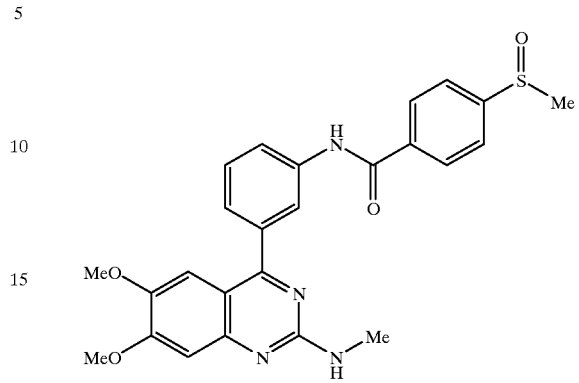

460 mg of 6,7-dimethoxy-2-methylamino-4-[3-(4-methylthiobenzoylamino)phenyl]quinazoline obtained in Example 26 was dissolved in 1 ml chloroform, and a solution of containing 246 mg 3-chloroperbenzoic acid dissolved in 1 ml chloroform was added dropwise thereto under ice-cooling. After the dropwise addition, the mixture was further stirred at 0° C. for 15 minutes. Ethyl acetate was added thereto, and it was washed with saturated aqueous sodium bicarbonate twice and with brine, and then dried over anhydrous magnesium sulfate. The solvent was evaporated, and the crude product was purified and separated by silica gel column chromatography (methanol:ethyl acetate=1:20). The product was recrystallized from hexane-ethyl acetate to give 253 mg of the title compound as yellow crystals.

$^1$H-NMR (400 MHz, CDCl$_3$) δ; 2.74(3H, s), 3.11(3H, d, J=5.0 Hz), 3.87(3H, s), 4.02(3H, s), 5.16(1H, m), 7.07(1H, s), 7.22(1H, s), 7.50–7.59(2H, m), 7.68–7.72(2H, m), 7.85 (1H, ddd, J=7.9, 1.8, 1.4 Hz), 7.98–8.02(2H, m), 8.06(1H, dd, J=1.8, 1.4 Hz), 8.51(1H, br s).

m.p.; 246–248° C.

MASS 477 (MH$^+$)

EXAMPLE 28

6,7-Dimethoxy-2-methylamino-4-[3-(4-methylsulfonylbenzoylamino)phenyl]quinazoline

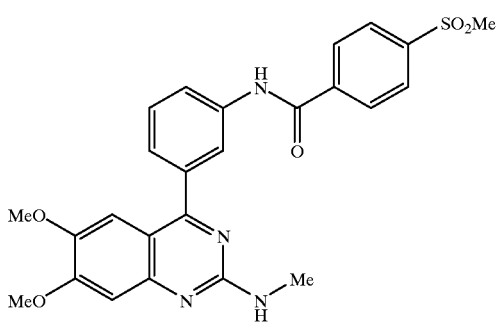

Starting from 230 mg of 6,7-dimethoxy-2-methylamino-4-[3-(4-methylthiobenzoylamino)phenyl]quinazolin in Example 26, 124 mg of the title compound was obtained as pale yellow crystals in the same manner as in Example 27.

¹H-NMR (400 MHz, CDCl₃) δ; 3.09(3H, s), 3.12(3H, d, J=5.0 Hz), 3.87(3H, s), 4.03(3H, s), 5.13(1H, m), 7.08(1H, s), 7.21(1H, s), 7.53–7.59(2H, m), 7.85(1H, ddd, J=7.9, 1.8, 1.4 Hz), 8.02–8.11(6H, m).

m.p.; 277–279° C.

MASS 493 (MH⁺)

EXAMPLE 29

4-[3-(6-Chloronicotinoylamino)phenyl]-6,7-dimethoxy-2-methylaminoquinazoline

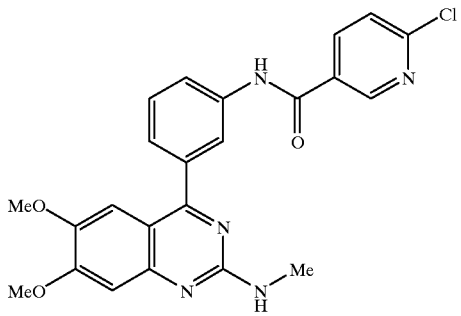

Starting from 6-chloronicotinoyl chloride obtained by chlorinating 965 mg of 6-chloronicotinoic acid with thionyl chloride, 1.44 g of the title compound was obtained as colorless crystals in the same manner as in Example 26.

¹H-NMR (400 MHz, CDCl₃) δ; 3.11(3H, d, J=4.9 Hz), 3.86(3H, s), 4.02(3H, s), 5.13(1H, m), 7.07(1H, s), 7.19(1H, s), 7.47(1H, dd, J=8.5, 0.8 Hz), 7.51–7.58(2H, m), 7.76(1H, ddd, J=7.9, 2.0, 1.4 Hz), 7.98(1H, dd, J=2.0, 1.4 Hz), 8.03(1H, br s), 8.17(1H, dd, J=8.5, 2.6 Hz), 8.87(1H, dd, J=2.6, 0.8)

m.p.; 157–159° C.

MASS 450 (MH⁺)

EXAMPLE 30

6,7-Dimethoxy-4-[3-(6-dimethylaminonicotinoylamino)phenyl]-2-methylaminoquinazoline

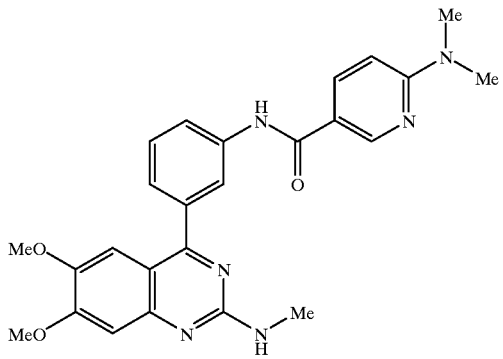

225 mg of 4-[3-(6-chloronicotinoylamino)phenyl]-6,7-dimethoxy-2-methylaminoquinazoline obtained in Example 29, 122 mg dimethylamine hydrochloride and 304 mg triethylamine were suspended in a mixed solvent of 5 ml isopropanol and 5 ml tetrahydrofuran and stirred at 130° C. for 18 hours in a sealed tube. Ethyl acetate was added thereto, and it was washed with water twice and with brine, and then dried over anhydrous magnesium sulfate. The solvent was evaporated, and the crude product was purified and separated by silica gel column chromatography (hexane:ethyl acetate=1:3). The product was recrystallized from hexane-ethyl acetate to give 185 mg of the title compound as pale yellow crystals.

¹H-NMR (400 MHz, CDCl₃) δ; 3.12(3H, d, J=5.0 Hz), 3.17(6H, s), 3.87(3H, s), 4.03(3H, s), 5.14(1H, m), 6.54(1H, dd, J=8.9, 0.6 Hz), 7.07(1H, s), 7.22(1H, s), 7.46(1H, ddd, J=7.7, 1.4, 1.2 Hz), 7.52(1H, dd, J=7.9, 7.7 Hz), 7.75–7.79 (2H, m), 7.94–7.99(2H, m), 8.70(1H, dd, J=2.6, 0.6 Hz).

m.p.; 149–151° C.

MASS 459 (MH⁺)

EXAMPLE 31

6,7-Dimethoxy-2-methylamino-4-[3-(6-pyrrolidinonicotinoylamino)phenyl]quinazoline

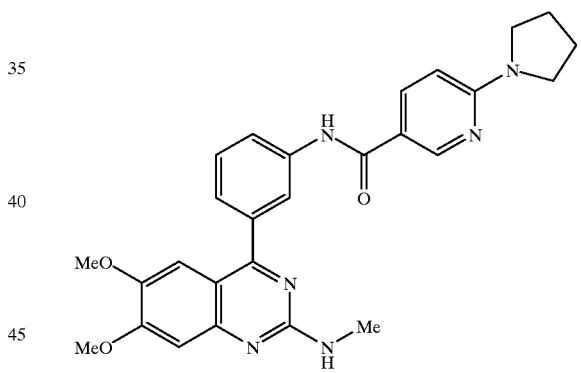

Starting from 167 mg of pyrrolidine, 183 mg of the title compound was obtained as yellow crystals in the same manner as in Example 30.

¹H-NMR (400 MHz, CDCl₃) δ; 2.01–2.08(4H, m), 3.11 (3H, d, J=5.0 Hz), 3.47–3.57(4H, m), 3.87(3H, s), 4.02(3H, s), 5.16(1H, m), 6.39(1H, dd, J=8.9, 0.6 Hz), 7.07(1H, s), 7.22(1H, s), 7.46(1H, ddd, J=7.7, 1.4, 1.2 Hz), 7.52(1-H, dd, J=7.9, 7.7 Hz), 7.73–7.80(2H, m), 7.93–7.97(2H, m), 8.69 (1H, dd, J=2.3, 0.6 Hz).

m.p.; 239–241° C.

MASS 485 (MH⁺)

EXAMPLE 32

6,7-Dimethoxy-2-methylamino-4-[3-(6-methylaminonicotinoylamino)phenyl]quinazoline

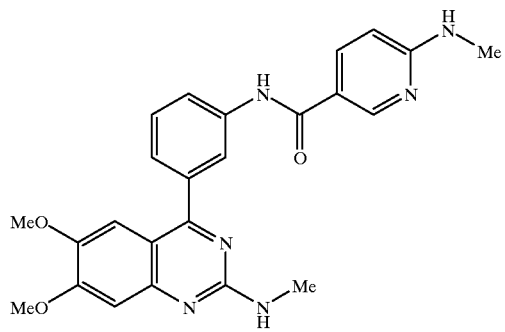

Starting from 5 ml solution of 40% methylamine in methanol, 162 mg of the title compound was obtained as yellow crystals in the same manner as in Example 30.

$^1$H-NMR (400 MHz, CDCl$_3$) δ; 2.99(3H, d, J=5.2 Hz), 3.12(3H, d, J=5.0 Hz), 3.87(3H, s), 4.03(3H, s), 5.00(1H, m), 5.15(1H, m), 6.43(1H, dd, J=8.8, 0.4 Hz), 7.07(1H, s), 7.21(1H, s), 7.44–7.56(2H, m), 7.74–7.80(2H, m), 7.94–7.98(2H, m), 8.64(1H, dd, J=2.2, 0.4 Hz).

m.p.; 193–195° C.

MASS 445 (MH$^+$)

EXAMPLE 33

4-[3-(2-Chloroisonicotinoylamino)phenyl]-6,7-dimethoxy-2-methylaminoquinazoline

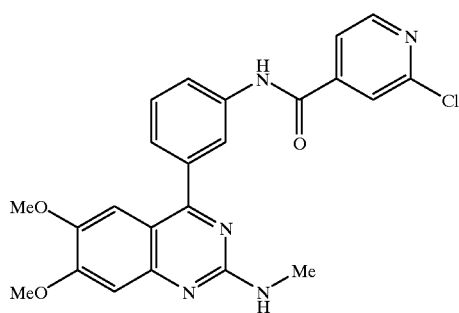

Starting from 2-chloroisonicotinoyl chloride obtained by chlorinating 946 mg of 2-chloroisonicotinoic acid with thionyl chloride, 1.07 g of the title compound was obtained as pale yellow crystals in the same manner as in Example 26.

$^1$H-NMR (400 MHz, CDCl$_3$) δ; 3.11(3H, d, J=4.9 Hz), 3.86(3H, s), 4.03(3H, s), 5.12(1H, m), 7.07(1H, s), 7.18(1H, s), 7.55–7.58 (2H, m), 7.63(1H, dd, J=5.1, 1.4 Hz), 7.72–7.78(2H, m), 8.00(1H, dd, J=1.8, 1.4 Hz), 8.07(1H, br s), 8.56(1H, dd, J=5.1, 0.7 Hz).

m.p.; 151–153° C.

MASS 450 (MH$^+$)

EXAMPLE 34

6,7-Dimethoxy-2-methylamino-4-[3-(2-pyrrolidinonicotinoylamino)phenyl]quinazoline

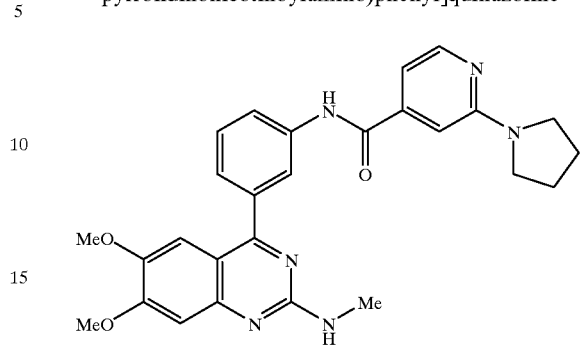

Starting from 225 mg of 4-[3-(2-chloroisonicotinoylamino)phenyl]-6,7-dimethoxy-2-methylaminoquinazol and 5 ml of pyrrolidine, 120 mg of the title compound was obtained as yellow crystals in the same manner as in Example 30.

$^1$H-NMR (400 MHz, CDCl$_3$) δ; 2.00–2.07(4H, m), 3.11 (3H, d, J=5.0 Hz), 3.47–3.54(4H, m), 3.86(3H, s), 4.03(3H, s), 5.13(1H, m), 6.78(1H, dd, J=5.3, 1.5 Hz), 6.81(1H, dd, J=1.5, 0.8 Hz), 7.07(1H, s), 7.19(1H, s), 7.49–7.57(2H, m), 7.80(1H, ddd, J=7.7, 2.0, 1.4 Hz), 7.96–8.00(2H, m), 8.27 (1H, dd, J=5.3, 0.8 Hz).

m.p.; 135–137° C.

MASS 485 (MH$^+$)

EXAMPLE 35

4-(3-Benzenesulfonamidephenyl)-6,7-dimethoxy-2-methylaminoquinazoline

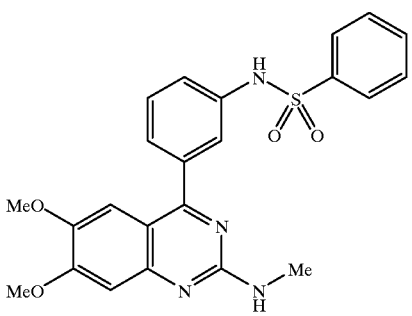

Starting from benzenesulfonyl chloride, 295 mg of the title compound was obtained as pale yellow crystals in the same manner as in Example 1.

$^1$H-NMR (400 MHz, CDCl$_3$) δ; 3.11(3H, d, J=4.8 Hz), 3.79(3H, s), 4.02(3H, s), 5.43(1H, m), 6.95–7.02(2H, m), 7.05(1H, s), 7.26–7.31 (2H, m), 7.39–7.47(3H, m), 7.54(1H, ddd, J=7.4, 2.4, 1.1 Hz), 7.74(1H, br s), 7.78–7.82(2H, m).

m.p.; 230–232° C.

MASS 451 (MH$^+$)

EXAMPLE 36

6,7-Dimethoxy-2-methylamino-4-[3-(3-phenylureido)phenyl]quinazoline

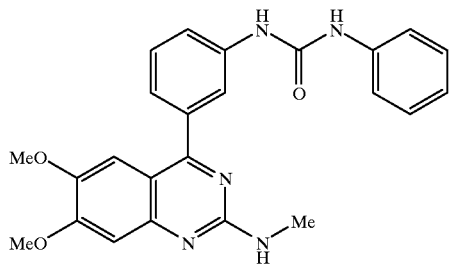

310 mg of 4-(3-aminophenyl)-6,7-dimethoxy-2-methylaminoquinazoline obtained in Production Example 7 and 131 mg of benzene isocyanate were suspended in 20 ml tetrahydrofuran and stirred at room temperature for 1 hour. After ethyl acetate was added thereto, it was washed with water thrice and with brine, and then dried over anhydrous magnesium sulfate. The solvent was evaporated, and the crude product was purified and separated by silica gel column chromatography (ethyl acetate). The product was recrystallized from hexane-ethyl acetate-tetrahydrofuran to give 374 mg of the title compound as colorless crystals.

$^1$H-NMR (400 MHz, CDCl$_3$) δ; 3.10(3H, d, J=4.9 Hz), 3.83(3H, s), 4.01(3H, s), 5.16(1H, m), 6.81(1H, m), 6.90 (1H, m), 7.06(1H, s), 7.10–7.16(2H, m), 7.31–7.40(5H, m), 7.45(1H, dd, J=8.6, 7.7 Hz), 7.56–7.60(2H, m).

m.p.; 218–220° C.

MASS 430 (MH$^+$)

EXAMPLE 37

6,7-Dimethoxy-2-methylamino-4-(3-phthalimide phenyl)quinazoline

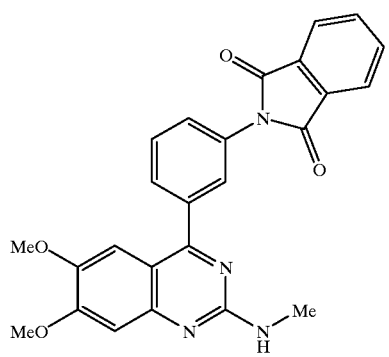

155 mg of 4-(3-aminophenyl)-6,7-dimethoxy-2-methylaminoquinazoline obtained in Production Example 7 and 110 mg of N-carboethoxy phthalimide were suspended in 10 ml tetrahydrofuran and stirred at 60° C. for 18 hours. After 10 ml diisopropyl ether was added thereto, the resulting crystals were collected by filtration, washed with tetrahydrofuran-diisopropyl ether and then air-dried to give 191 mg of the title compound as yellow crystals.

$^1$H-NMR (400 MHz, CDCl$_3$) δ; 2.90(3H, d, J=5.0 Hz), 3.84(3H, s), 3.93(3H, s), 7.01(1H, s), 7.10(1H, m), 7.22(1H, s), 7.66(1H, ddd, J=8.0, 2.0, 1.4 Hz), 7.75(1H, dd, J=8.0, 7.8 Hz), 7.81(1H, ddd, J=7.8, 1.4, 1.4 Hz), 7.85(1H, dd, J=2.0, 1.4 Hz), 7.90–7.95(2H, m), 7.97–8.02(2H, m).

m.p.; 280–282° C.

MASS 441 (MH$^+$)

EXAMPLE 38

4-(3-Benzylaminophenyl)-6,7-dimethoxy-2-methylaminoquinazoline

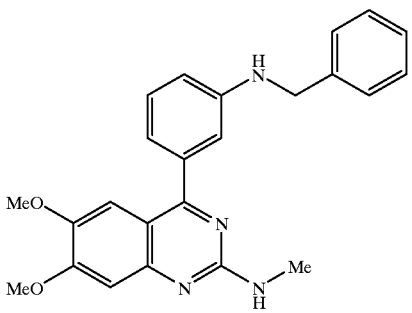

310 mg of 4-(3-aminophenyl)-6,7-dimethoxy-2-methylaminoquinazoline obtained in Production Example 7, 85.5 mg benzyl bromide and 138 mg potassium carbonate were suspended in 10 ml N,N-dimethyl formamide and stirred at room temperature for 2 hours. After ethyl acetate was added thereto, the mixture was washed with water 5 times and with brine, and then dried over anhydrous magnesium sulfate. The solvent was evaporated, and the crude product was purified and separated by silica gel column chromatography (hexane:ethyl acetate=1:1). The product was recrystallized from hexane-ethyl acetate to give 110 mg of the title compound as pale yellow crystals.

$^1$H-NMR (400 MHz, CDCl$_3$) δ; 3.10(3H, d, J=5.0 Hz), 3.76(3H, s), 4.02(3H, s), 4.22(1H, m), 4.38(2H, d, J=4.6 Hz), 5.16(1H, m), 6.76(1H, ddd, J=8.2, 2.4, 0.8 Hz), 6.95 (1H, dd, J=2.4, 1.6 Hz), 7.00(1H, ddd, J=8.6, 1.6, 0.8 Hz), 7.06(1H, s), 7.14(1H, s), 7.25–7.42 (6H, m).

m.p.; 146–148° C.

MASS 401 (MH$^+$)

EXAMPLE 39

4-[3-(N-benzyl-N-methylamino)phenyl]-6,7-dimethoxy-2-methylaminoquinazoline

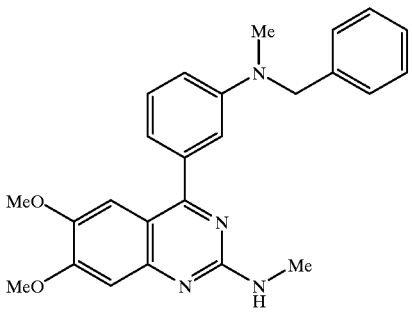

Starting from 100 mg of 4-(3-benzylaminophenyl)-6,7-dimethoxy-2-methylaminoquinazoline obtained in Example 38 and 71.0 mg of methyl iodide, 35.0 mg of the title compound was obtained as a pale yellow oil in the same manner as in Example 38.

$^1$H-NMR (400 MHz, CDCl$_3$) δ; 3.07(3H, s), 3.11(3H, d, J=4.9 Hz), 3.74(3H, s), 4.02(3H, s), 4.60(2H, s), 5.16(1H, m), 6.88(1H, ddd, J=8.4, 2.4, 0.5 Hz), 7.00(1H, dd, J=8.2, 0.5 Hz), 7.04–7.07(2H, m), 7.16(1H, s), 7.21–7.37(6H, m).

MASS 415 (MH$^+$)

EXAMPLE 40

4-[3-(N-benzyl-N-ethylamino)phenyl]-6,7-dimethoxy-2-methylaminoquinazoline

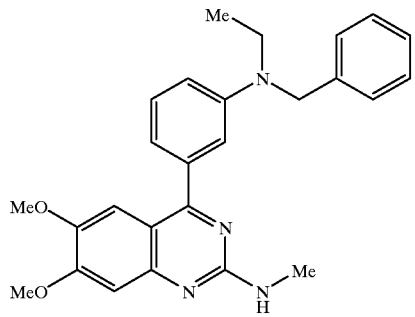

Starting from 78.0 mg of ethyl iodide, 28.0 mg of the title compound was obtained as a pale yellow oil in the same manner as in Example 39.

$^1$H-NMR (400 MHz, CDCl$_3$) δ; 1.23(3H, t, J=7.0 Hz), 3.09(3H, d, J=4.9 Hz), 3.52(2H, q, J=7.0 Hz), 3.75(3H, s), 4.02(3H, s), 4.58(2H, s), 5.12(1H, m), 6.88(1H, ddd, J=8.4, 2.2, 0.5 Hz), 6.96(1H, dd, J=8.2, 0.5 Hz), 7.01(1H, dd, J=2.2, 1.2 Hz), 7.05(1H, s), 7.16(1H, s), 7.20–7.34 (6H, m).

MASS 429 (MH$^+$)

EXAMPLE 41

4-[3-(N-benzyl-N-propylamino)phenyl]-6,7-dimethoxy-2-methylaminoquinazoline

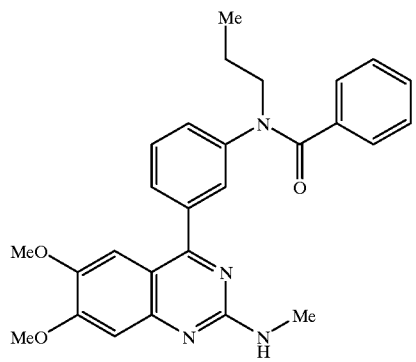

Starting from 200 mg of 4-(3-benzylaminophenyl)-6,7-dimethoxy-2-methylaminoquinazoline obtained in Example 38 and 170 mg of 1-iodopropyl, 66.0 mg of the title compound was obtained as pale yellow crystals in the same manner as in Example 38.

$^1$H-NMR (400 MHz, CDCl$_3$) δ; 0.92(3H, t, J=7.4 Hz), 1.71(2H, m), 3.09(3H, d, J=5.0 Hz), 3.52(2H, t, J=7.3 Hz), 3.74(3H, s), 4.01(3H, s), 4.61(2H, s), 5.12(1H, m), 6.78(1H, ddd, J=8.4, 1.7, 0.7 Hz), 6.94(1H, dd, J=7.6, 0.7 Hz), 6.98(1H, dd, J=2.5, 1.7 Hz), 7.05(1H, s), 7.15(1H, s), 7.20–7.34(6H, m).

m.p.; 75–77° C.

MASS 443 (MH$^+$)

EXAMPLE 42

4-[3-(N-benzoyl-N-methylamino)phenyl]-6,7-dimethoxy-2-methylaminoquinazoline

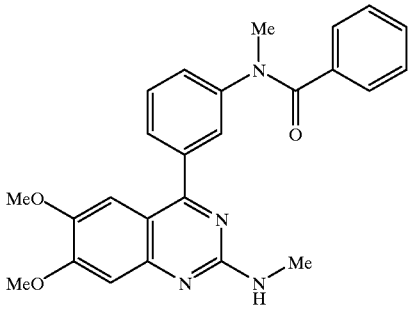

207 mg of 4-(3-benzoylaminophenyl)-6,7-dimethoxy-2-methylaminoquinazoline obtained in Example 1 was dissolved in 5 ml tetrahydrofuran, and 0.667 ml of 1.5 M lithium diisopropylamide in hexane was added dropwise thereto at −70° C. After the dropwise addition, the mixture was stirred at −70° C. for 30 minutes, and then 284 mg of methyl iodide was added thereto. The mixture was returned to room temperature and further stirred for 1 hour. After ethyl acetate was added thereto, the mixture was washed with water twice and with brine, and then dried over anhydrous magnesium sulfate. The solvent was evaporated, and the crude product was purified and separated by silica gel column chromatography (hexane:ethyl acetate=1:3). The product was recrystallized from hexane-ethyl acetate to give 75 mg of the title compound as pale yellow crystals.

$^1$H-NMR (400 MHz, CDCl$_3$) δ; 3.10(3H, d, J=5.0 Hz), 3.55(3H, s), 3.78(3H, s), 4.02(3H, s), 5.11(1H, m), 6.90(1H, s), 7.06(1H, s), 7.13–7.28(4H, m), 7.35–7.40(3H, m), 7.46–7.50(2H, m).

m.p.; 198–200° C.

MASS 429 (MH$^+$)

EXAMPLE 43

6,7-Dimethoxy-2-methylamino-4-[3-(1-pyrrolyl)phenyl]quinazoline

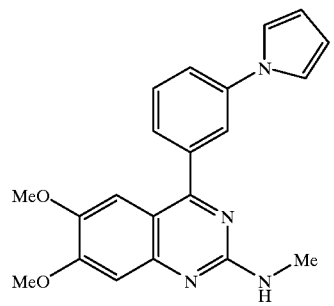

310 mg of 4-(3-aminophenyl)-6,7-dimethoxy-2-methylaminoquinazoline obtained in Production Example 7 and 132 mg of 2,5-dimethoxy tetrahydrofuran were suspended in 1 ml acetic acid and heated under reflux for 15 minutes. After ethyl acetate was added thereto, the mixture was washed with aqueous saturated sodium bicarbonate thrice and with brine, and then dried over anhydrous magnesium sulfate. The solvent was evaporated, and the crude product was purified and separated by silica gel column chromatography (hexane:ethyl acetate=1:1). The product was recrystallized from hexane-ethyl acetate to give 179 mg of the title compound as yellow crystals.

$^1$H-NMR (400 MHz, CDCl$_3$) δ; 3.12(3H, d, J=5.0 Hz), 3.82(3H, s), 4.04(3H, s), 5.17(1H, m), 6.38(2H, t, J=2.2 Hz), 7.08(1H, s), 7.09(1H, s), 7.16(2H, t, J=2.2 Hz), 7.53–7.61 (3H, m), 7.74(1H, dd, J=1.8, 1.4 Hz).

m.p.; 199–201° C.

MASS 361 (MH$^+$)

EXAMPLE 44

6,7-Dimethoxy-4-[3-(2-isoindolynyl)phenyl]-2-methylaminoquinazoline

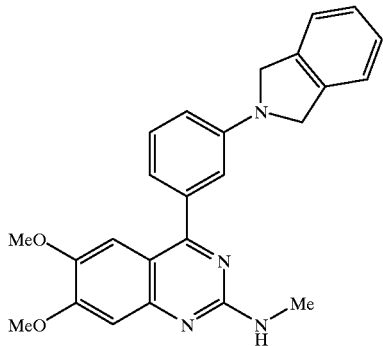

827 mg of 4-(3-aminophenyl)-6,7-dimethoxy-2-methylaminoquinazoline obtained in Production Example 7, 705 mg α, α'-dibromo-o-xylene and 738 mg potassium carbonate were dissolved in 30 ml N,N-dimethylformamide and stirred at 60° C. for 15 hours. After ethyl acetate was added thereto, the mixture was washed with water 5 times and with brine, and then dried over anhydrous magnesium sulfate. The solvent was evaporated, and the crude product was purified and separated by silica gel column chromatography (hexane: ethyl acetate=1:1). The product was recrystallized from hexane-ethyl acetate to give 613 mg of the title compound as yellow crystals.

$^1$H-NMR (400 MHz, CDCl$_3$) δ; 3.13(3H, d, J=4.7 Hz), 3.82(3H, s), 4.03(3H, s), 4.72(4H, s), 5.16(1H, m), 6.82(1H, ddd, J=8.2, 2.4, 0.8 Hz), 6.97(1H, dd, J=2.4, 1.6 Hz), 7.04(1H, ddd, J=7.6, 1.6, 0.8 Hz), 7.09(1H, s), 7.25(1H, s), 7.29–7.38(4H, m), 7.44(1H, dd, J=7.6,8.2 Hz).

m.p.; 194–196° C.

MASS 413 (MH$^+$)

EXAMPLE 45

6,7-Dimethoxy-4-[3-(1-oxo-2-isoindolynyl)phenyl]-2-methylaminoquinazoline

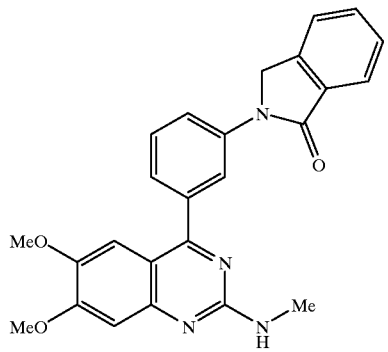

155 mg of 4-(3-aminophenyl)-6,7-dimethoxy-2-methylaminoquinazoline obtained in Production Example 7, 67 mg phthalic carbaldehyde and 5 mg acetic acid were dissolved in 1 ml chloroform and stirred at 50° C. for 1 hour. After ethyl acetate was added thereto, the mixture was washed with water twice and with brine, and then dried over anhydrous magnesium sulfate. The solvent was evaporated, and the crude product was purified and separated by silica gel column chromatography (hexane:ethyl acetate=1:3). The product was recrystallized from hexane-ethyl acetate to give 50.0 mg of the title compound as yellow crystals.

$^1$H-NMR (400 MHz, CDCl$_3$) δ; 3.13(3H, d, J=5.0 Hz), 3.87(3H, s), 4.04(3H, s), 4.93(2H, s), 5.18(1H, m), 7.08(1H, s), 7.24(1H, s), 7.49–7.57(3H, m), 7.58–7.64(2H, m), 7.94 (1H, ddd, J=7.4, 2.0, 1.0 Hz), 8.06(1H, ddd, J=8.2, 2.4, 1.0 Hz), 7.97(1H, dd, J=2.0, 1.4 Hz).

m.p.; 230–232° C.

MASS 427 (MH$^+$)

EXAMPLE 46

4-(3-Biphenylyl)-6,7-dimethoxy-2-methylaminoquinazoline

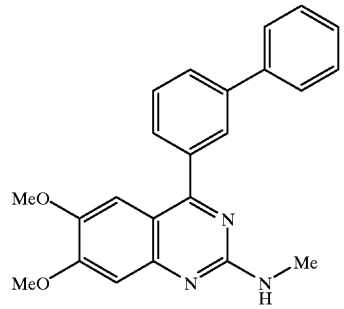

Starting from 90 mg of 4-(3-biphenylyl)-2-chloro-6,7-dimethoxyquinazoline obtained in Production Example 2 and 10 ml solution of 40% methylamine in methanol, 808 mg of the title compound was obtained as a pale yellow crystals in the same manner as in Production Example 8.

$^1$H-NMR (400 MHz, CDCl$_3$) δ; 3.14(3H, d, J=4.8 Hz), 3.82(3H, s), 4.04(3H, s), 4.58(1H, br s), 7.09(1H, s), 7.15 (1H, s), 7.37(1H, m), 7.46(2H, m), 7.60(1H, t, J=7.6 Hz), 7.65(2H, m), 7.67(1H, dt, J=7.6, 1.6 Hz), 7.75(1H, dt, J=7.6, 1.6 Hz), 7.93(1H, t, J=1.6 Hz).

m.p.; 183–185° C.

MASS 372 (MH+)

EXAMPLE 47

6,7-Dimethoxy-2-methylamino-4-[3-(3-pyridyl)phenyl]quinazoline

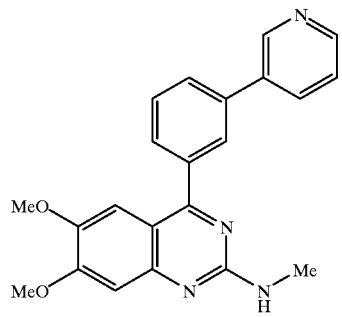

250 mg of 4-(3-bromophenyl)-6,7-dimethoxy-2-methylaminoquinazoline obtained in Production Example 8, 150 mg of 3-pyridyl diethyl borane, 50 mg of tetrakis(triphenyl phosphine)palladium, 50 mg of tetrabutyl ammonium bromide and 120 mg potassium hydroxide were suspended in 10 ml tetrahydrofuran and heated under reflux for 4 hours. After ethyl acetate was added thereto, the mixture was washed with water twice and with brine, and then dried over anhydrous magnesium sulfate. The solvent was evaporated, and the crude product was purified and separated by silica gel column chromatography (dichloromethane:methanol=30:1). The product was recrystallized from hexane-chloroform to give 210 mg of the title compound as pale yellow crystals.

$^1$H-NMR (400 MHz, CDCl$_3$) δ; 3.14(3H, d, J=5.2 Hz), 3.82(3H, s), 4.04(3H, s), 5.13(1H, br s), 7.10(1H, s), 7.11(1H, s), 7.39(1H, m), 7.65(1H, t, J=7.6 Hz), 7.72–7.76(2H, m), 7.92–7.95(2H, m), 8.62(1H, dd, J=4.8, 1.6 Hz), 8.92(1H, dd, J=2.4, 0.8 Hz).

m.p.; 186–188° C.

MASS 373 (MH+)

EXAMPLE 48

6,7-Dimethoxy-4-(3',4'-dimethyl-3-biphenylyl)-2-methylaminoquinazoline

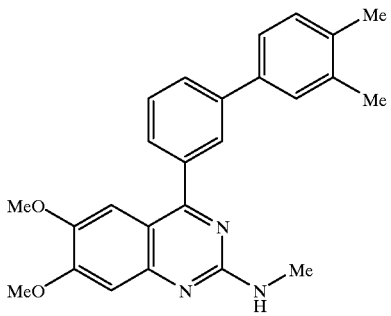

250 mg of 4-(3-bromophenyl)-6,7-dimethoxy-2-methylaminoquinazoline obtained in Production Example 8, 200 mg of 1,2-dimethyl-4-phenyl boric acid obtained from 4-bromo-o-xylene according to the method of J. Org. Chem., 56, 3763 (1991) and 50 mg tetrakis(triphenyl phosphine) palladium were suspended in a mixed solvent of 20 ml toluene, 5 ml methanol and 10 ml of 2 M aqueous sodium carbonate, and the mixture was stirred at 80° C. for 8 hours. The organic layer was recovered, washed with water twice and with brine, and then dried over anhydrous magnesium sulfate. The solvent was evaporated, and the crude product was purified and separated by silica gel column chromatography (hexane:ethyl acetate=1:1). The product was recrystallized from hexane-diisopropyl ether to give 186 mg of the title compound as pale yellow crystals.

$^1$H-NMR (400 MHz, CDCl$_3$) δ; 2.31(3H, s), 2.33(3H, s), 3.14(3H, d, J=4.8 Hz), 3.82(3H, s), 4.04(3H, s), 5.14(1H, br s), 7.09(1H, s), 7.16(1H, s), 7.22(1H, m), 7.39(1H, m), 7.43(1H, m), 7.58(1H, t, J=7.6 Hz), 7.63(1H, dt, J=7.6, 1.6 Hz), 7.73(1H, dt, J=7.6, 1.6 Hz), 7.90(1H, t, J=1.6 Hz).

m.p.; 149–151° C.

MASS 400 (MH+)

EXAMPLE 49

6,7-Dimethoxy-2-methylamino-4-[3-(3-quinolyl)phenyl]quinazoline

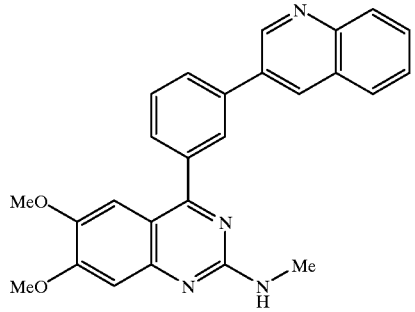

250 mg of 4-(3-bromophenyl)-6,7-dimethoxy-2-methylaminoquinazoline obtained in Production Example 8, 300 mg of 3-quinolyl diethyl borane obtained from 4-bromoquinoline according to the method of Heterocycles, 22, 2471 (1984), 50 mg tetrakis(triphenyl phosphine) palladium, 50 mg tetrabutyl ammonium bromide and 120 mg potassium hydroxide were suspended in 10 ml tetrahydrofuran, and the mixture was heated under reflux for 6 hours. After ethyl, acetate was added thereto, the mixture was washed with water twice and with brine, and then dried over anhydrous magnesium sulfate. The solvent was evaporated, and the crude product was purified and separated by silica gel column chromatography (ethyl acetate:methanol=30:1). The product was recrystallized from hexane-chloroform to give 236 mg of the title compound as pale yellow crystals.

$^1$H-NMR (400 MHz, CDCl$_3$) δ; 3.15(3H, d, J=4.8 Hz), 3.83(3H, s), 4.05(3H, s),5.16(1H, br s), 7.11(1H, s), 7.15(1H, s), 7.60(1H, m), 7.70(1H, t, J=8.0 Hz), 7.73–7.78(2H, m), 7.87–7.90(2H, m), 8.06(1H, t, J=1.6 Hz), 8.16(1H, d, J=8.0 Hz), 8.38(1H, d, J=2.4 Hz), 9.25(1H, d, J=2.4 Hz).

m.p.; 218–220° C.

MASS 423 (MH+)

EXAMPLE 50

6,7-Dimethoxy-4-[3-(imidazo[1,2-a]pyridine-6-yl)phenyl]-2-methylaminoquinazoline

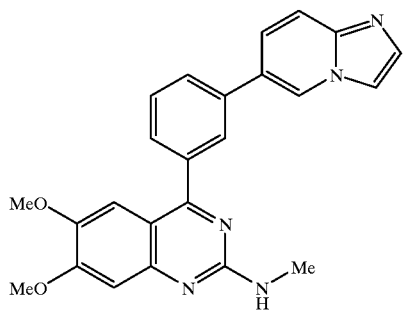

Starting from 250 mg of imidazo[1,2-a]pyridin-6-yl diethyl borane obtained from 6-bromoimidazo[1,2-a]pyridine according to the method of Heterocycles, 22, 2471, 1984., 176 mg of the title compound was obtained as yellow crystals in the same manner as in Example 49.

$^1$H-NMR (400 MHz, CDCl$_3$) δ; 3.14(3H, d, J=4.8 Hz), 3.82(3H, s), 4.04(3H, s), 5.15(1H, br s), 7.10(2H, s), 7.49 (1H, dd, J=5.4, 1.8 Hz), 7.62–7.74(6H, m), 7.91(1H, t, J=1.8 Hz), 8.40(1H, dd, J=1.6, 0.8 Hz).

m.p.; 237–239° C.

MASS 412 (MH$^+$)

EXAMPLE 51

6,7-Dimethoxy-2-methylamino-4-[3-(4-isoquinolyl)phenyl]quinazoline

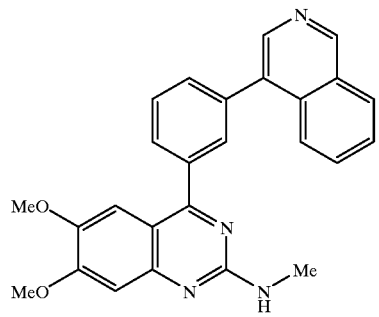

Starting from 250 mg of 4-isoquinolyl diethyl borane obtained from 4-bromoisoquinoline according to the method of Heterocycles, 22, 2471, 1984., 147 mg of the title compound was obtained as yellow crystals in the same manner as in Example 49.

$^1$H-NMR (400 MHz, CDCl$_3$) ) δ; 3.13(3H, d, J=4.8 Hz), 3.85(3H, s), 4.03(3H, s), 5.13(1H, br s), 7.09(1H, s), 7.20 (1H, s), 7.63–7.73 (4H, m), 7.83(1H, m), 7.88(1H, m), 7.98(1H, m), 8.07(1H, m) 8.56(1H, s), 9.29(1H, s).

m.p.; 181–183° C.

MASS 423 (MH$^+$)

EXAMPLE 52

6,7-Dimethoxy-2-methylamino-4-(4'-methylthio-3-biphenylyl)quinazoline

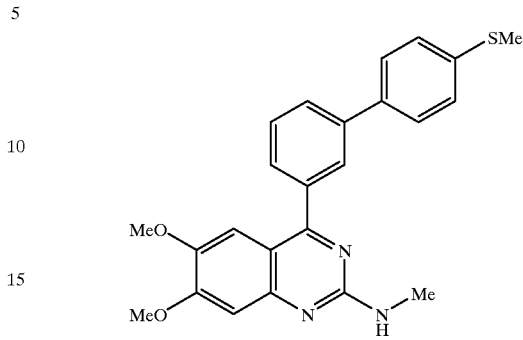

Starting from 450 mg of 4-methylthiophenylboric acid obtained from 750 mg of 4-(3-bromophenyl)-6,7-dimethoxy-2-methylaminoquinazoline obtained in Production Example 8 and 4-bromothioanisole according to the method of J. Org. Chem., 56, 3763, 1991., 523 mg of the title compound was obtained as pale yellow crystals in the same manner as in Example 48.

$^1$H-NMR (400 MHz, CDCl$_3$) δ; 2.53(3H, s), 3.14(3H, d, J=4.8 Hz), 3.81(3H, s), 4.04(3H, s), 5.14(1H, br s),7.09(1H, s), 7.13(1H, s) 7.34(2H, d, J=8.8 Hz), 7.58(2H, d, J=8.8 Hz), 7.60(1H, t, J=7.6 Hz), 7.65(1H, dt, J=7.6, 1.6 Hz), 7.72(1H, dt, J=7.6, 1.6 Hz), 7.90(1H, t, J=1.6 Hz).

m.p.; 140–142° C.

MASS 418 (MH$^+$)

EXAMPLE 53

6,7-Dimethoxy-2-methylamino-4-(4'-methylsulfinyl-3-biphenylyl)quinazoline

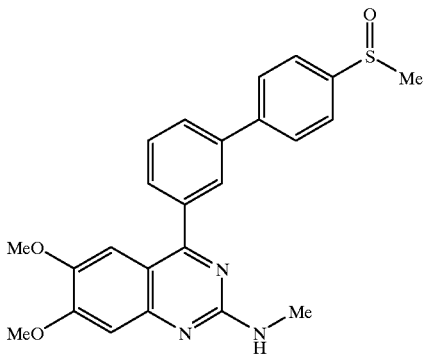

Starting from 250 mg of 6,7-dimethoxy-2-methylamino-4-(4'-methylthio-3-biphenylyl)quinazoline obtained in Example 52, 139 mg of the title compound was obtained as pale yellow crystals in the same manner as in Example 27.

$^1$H-NMR (400 MHz, CDCl$_3$) δ; 2.78(3H, s), 3.13(3H, d, J=4.8 Hz), 3.81(3H, s), 4.04(3H, s), 5.17(1H, br s), 7.10(1H, s), 7.11(1H, s), 7.64(1H, t, J=7.6 Hz), 7.72(1H, dt, J=7.6, 1.6 Hz), 7.74(2H, d, J=8.4 Hz), 7.76(1H, dt, J=7.6, 1.6 Hz), 7.81(2H, d, J=8.8 Hz), 7.94(1H, t, J=1.6 Hz).

m.p.; 153–155° C.

MASS 434 (MH$^+$)

EXAMPLE 54

6,7-Dimethoxy-2-methylamino-4-(3'-methylthio-3-biphenylyl)quinazoline

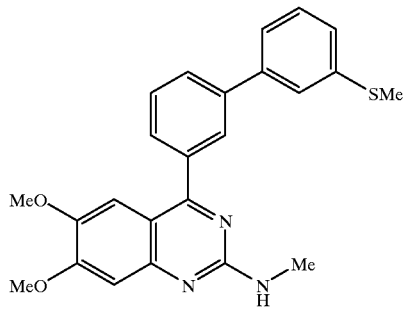

Starting from 450 mg of 3-methylthiophenylboric acid obtained from 3-bromothioanisole according to the method of *J. Org. Chem.*, 56, 3763, 1991., 485 mg of the title compound was obtained as pale yellow crystals in the same manner as in Example 52.

$^1$H-NMR (400 MHz, CDCl$_3$) δ; 2.53(3H, s), 3.14(3H, d, J=4.8 Hz), 3.82(3H, s), 4.04(3H, s), 5.15(1H, br s), 7.09(1H, s), 7.13(1H, s), 7.27(1H, dt, J=7.6, 1.6 Hz), 7.38(1H, t, J=7.6 Hz), 7.41(1H, dt, J=7.6, 1.6 Hz), 7.53(1H, t, J=1.6 Hz), 7.60(1H, t, J=7.6 Hz), 7.68(1H, dt, J=7.6, 1.6 Hz), 7.73(1H, dt, J=7.6, 1.6 Hz), 7.90(1H, t, J=1.6 Hz).

m.p.; 195–197° C.

MASS 418 (MH$^+$)

EXAMPLE 55

6,7-Dimethoxy-2-methylamino-4-(3'-methylsulfinyl-3-biphenylyl)quinazoline

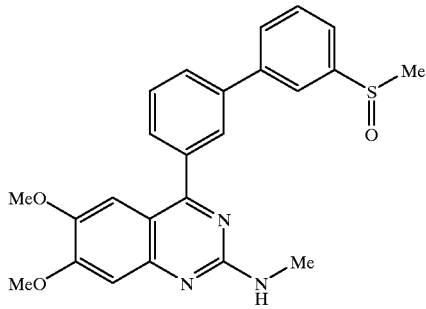

Starting from 250 mg of 6,7-dimethoxy-2-methylamino-4-(3'-methylthio-3-biphenylyl)quinazoline obtained in Example 54, 145 mg of the title compound was obtained as pale yellow crystals in the same manner as in Example 27.

$^1$H-NMR (400 MHz, CDCl$_3$) δ; 2.78(3H, s), 3.14(3H, d, J=5.2 Hz), 3.82(3H, s), 4.04(3H, s), 5.15(1H, br s), 7.09(1H, s), 7.10(1H, s), 7.61–7.65(3H, m), 7.71(1H, dt, J=7.6, 1.6 Hz), 7.77–7.80(2H, m), 7.95–7.97(2H, m).

m.p.; 163–165° C.

MASS 434 (MH$^+$)

EXAMPLE 56

6,7-Dimethoxy-2-methylamino-4-(3'-phenyl-3-biphenylyl)quinazoline

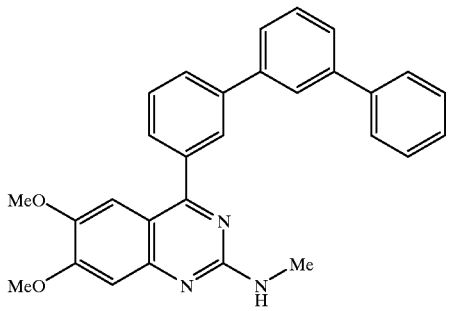

Starting from 200 mg of 3-biphenylboric acid, 202 mg of the title compound was obtained as pale yellow crystals in the same manner as in Example 48.

$^1$H-NMR (400 MHz, CDCl$_3$) δ; 3.13(3H, d, J=5.2 Hz), 3.82(3H, s), 4.04(3H, s), 5.16(1H, br s), 7.10(1H, s), 7.17(1H, s), 7.37(1H, m), 7.43–7.48(2H, m), 7.53(1H, t, J=7.6 Hz), 7.59–7.65(5H, m), 7.69(1H, dt, J=7.6, 1.6 Hz), 7.81(1H, dt, J=7.6, 1.6 Hz), 7.86(1H, t, J=1.6 Hz), 7.98(1H, t, J=1.6 Hz).

m.p.; 193–195° C.

MASS 448 (MH$^+$)

EXAMPLE 57

6,7-Dimethoxy-4-[3-(5-methoxy-3-pyridyl)phenyl]-2-methylaminoquinazoline

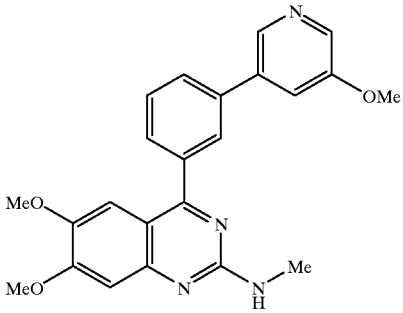

Starting from 250 mg of 3-methoxypyridin-5-yl diethyl borane obtained from 3-bromo-5-methoxypyridine according to the method of *Heterocycles*, 22, 2471, 1984., 206 mg of the title compound was obtained as pale yellow crystals in the same manner as in Example 49.

$^1$H-NMR (400 MHz, CDCl$_3$) δ; 3.14(3H, d, J=4.8 Hz), 3.82(3H, s), 3.92(3H, s), 4.04(3H, s), 5.14(1H, br s), 7.10(1H, s), 7.11(1H, s), 7.42(1H, dd, J=2.8, 1.8 Hz), 7.64(1H, t, J=7.6 Hz), 7.71–7.75(2H, m), 7.91(1H, t, J=1.6 Hz), 8.33(1H, d, J=2.8 Hz), 8.52(1H, d, J=1.8 Hz).

m.p.; 225–227° C.

MASS 403 (MH$^+$)

EXAMPLE 58

6,7-Dimethoxy-2-methylamino-4-[3-(5-methylthio-3-pyridyl)phenyl]quinazoline

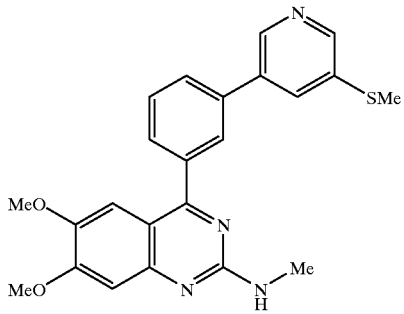

Starting from 550 mg of 3-methylthiopyridin-5-yl diethyl borane obtained from 3-bromo-5-methylthiopyridine according to the method of *Heterocycles,* 22, 2471, 1984., 440 mg of the title compound was obtained as pale yellow crystals in the same manner as in Example 52.

$^1$H-NMR (400 MHz, CDCl$_3$) δ; 2.56(3H, s), 3.14(3H, d, J=5.2 Hz), 3.82(3H, s), 4.04(3H, s), 5.15(1H, br s), 7.10(2H, s), 7.65(1H, t, J=7.6 Hz), 7.71–7.75(2H, m), 7.79(1H, t, J=2.2 Hz), 7.90(1H, t, J=1.6 Hz), 8.50(1H, d, J=2.2 Hz), 8.66(1H, d, J=2.2 Hz).

m.p.; 184–186° C.

MASS 419 (MH$^+$)

EXAMPLE 59

6,7-Dimethoxy-2-methylamino-4-[3-(5-methylsulfinyl-3-pyridyl)phenyl]quinazoline

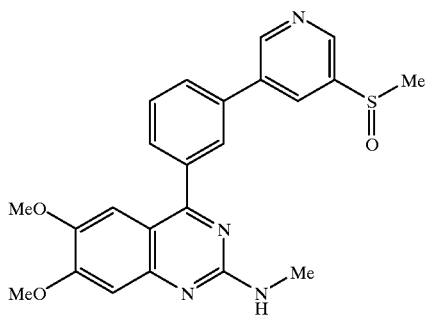

Starting from 250 mg of 6,7-dimethoxy-2-methylamino-4-[3-(5-methylthio-3-pyridyl)phenyl]quinazoline obtained in Example 58, 124 mg of the title compound was obtained as pale yellow crystals in the same manner as in Example 27.

$^1$H-NMR (400 MHz, CDCl$_3$) δ; 2.86(3H, s), 3.14(3H, d, J=5.2 Hz), 3.82(3H, s), 4.04(3H, s), 5.16(1H, br s), 7.08(1H, s), 7.10(1H, s), 7.68(1H, t, J=7.6 Hz), 7.77–7.82(2H, m), 7.98(1H, t, J=1.6 Hz), 8.35(1H, t, J=2.0 Hz), 8.75(1H, d, J=2.0 Hz), 9.03(1H, d, J=2.0 Hz).

m.p.; 208–210° C.

MASS 435 (MH$^+$)

EXAMPLE 60

6,7-Diethoxy-2-methylamino-4-[3-(3-quinolyl)phenyl]quinazoline

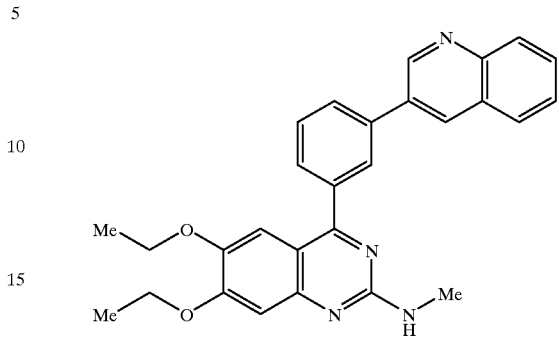

Starting from 250 mg of 4-(3-bromophenyl)-6,7-diethoxy-2-methylaminoquinazoline obtained in Production Example 15 and 200 mg of 3-quinolyl diethyl borane, 121 mg of the title compound was obtained as yellow crystals in the same manner as in Example 49.

m.p.; 157–159° C.

MASS 451 (MH$^+$)

$^1$H-NMR (400 MHz, CDCl$_3$) δ; 1.43(3H, t, J=7.2 Hz), 1.55(3H, t, J=7.2 Hz), 3.14(3H, d, J=5.2 Hz), 4.00(2H, q, J=7.2 Hz), 4.27(2H, q, J=7.2 Hz), 5.12(1H, br s), 7.08(1H, s), 7.15(1H, s), 7.60(1H, m), 7.71(1H, t, J=8.0 Hz), 7.73–7.78(2H, m), 7.86–7.91 (2H, m), 8.05(1H, t, J=1.6 Hz), 8.15(1H, d, J=8.4 Hz), 8.38(1H, d, J=2.4 Hz), 9.25(1H, d, J=2.4 Hz).

EXAMPLE 61

6,7-Diethoxy-2-methylamino-4-[3-(5-methylthio-3-pyridyl)phenyl]quinazoline

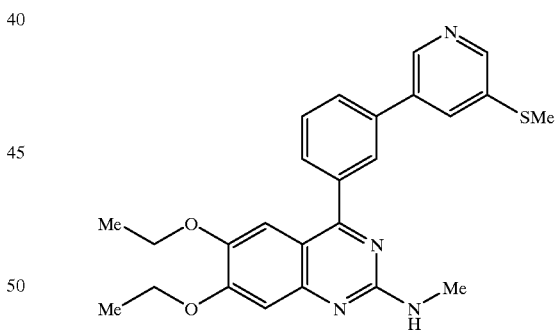

Starting from 1.00 g of 4-(3-bromophenyl)-6,7-diethoxy-2-methylaminoquinazoline obtained in Production Example 15 and 700 mg of 3-methylthiopyridin-5-yl diethyl borane, 472 mg of the title compound was obtained as pale yellow crystals in the same manner as in Example 49.

m.p.; 105–107° C.

MASS 447 (MH$^+$)

$^1$H-NMR (400 MHz, CDCl$_3$) δ; 1.43(3H, t, J=7.2 Hz), 1.55(3H, t, J=7.2 Hz), 2.56(3H, s), 3.13(3H, d, J=4.8 Hz), 4.00(2H, q, J=7.2 Hz), 4.27(2H, q, J=7.2 Hz), 5.12(1H, br s), 7.07(1H, s), 7.12(1H, s), 7.64(1H, t, J=7.6 Hz), 7.70–7.75 (2H, m), 7.78(1H, t, J=2.2 Hz), 7.89(1H, t, J=1.8 Hz), 8.50(1H, d, J=2.2 Hz), 8.66(1H, d, J=2.2 Hz).

EXAMPLE 62

6,7-Diethoxy-2-methylamino-4-[3-(5-methylsulfinyl-3-pyridyl)phenyl]quinazoline

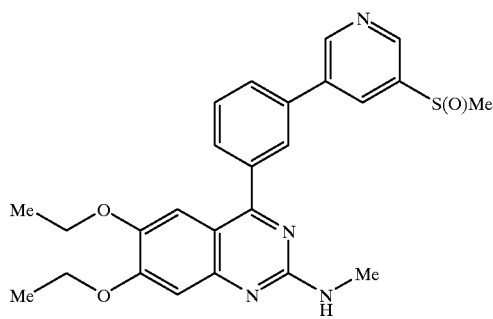

Starting from 360 mg of 6,7-diethoxy-2-methylamino-4-[3-(5-methylthio-3-pyridyl)phenyl]quinazoline obtained in Example 61, 84 mg of the title compound was obtained as yellow crystals in the same manner as in Example 27.

m.p.; 188–190° C.

MASS 463 (MH$^+$)

$^1$H-NMR (400 MHz, CDCl$_3$) δ; 1.43(3H, t, J=7.2 Hz), 1.56(3H, t, J=7.2 Hz), 2.86(3H, s), 3.13(3H, d, J=5.2 Hz), 4.00(2H, q, J=7.2 Hz), 4.26(2H, q, J=7.2 Hz), 5.17(1H, br s), 7.07(1H, s), 7.09(1H, s), 7.68(1H, t, J=7.6 Hz), 7.74–7.81 (2H, m) 7.97(1H, t, J=1.6 Hz), 8.34(1H, t, J=2.0 Hz), 8.75(1H, d, J=2.0 Hz), 9.03(1H, d, J=2.0 Hz).

EXAMPLE 63

6,7-Dimethoxy-2-methylamino-4-[3-(5-phenyl-3-pyridyl)phenyl]quinazoline

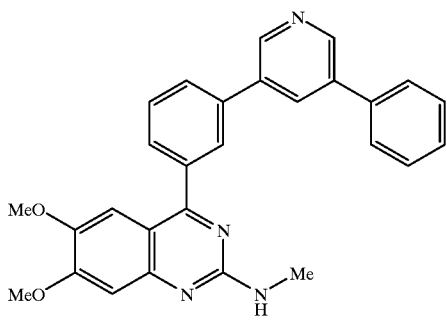

Starting from 250 mg of 4-(3-bromophenyl)-6,7-dimethoxy-2-methylaminoquinazoline obtained in Production Example 8 and 250 mg of 5-phenyl-3-pyridyl diethyl borane, 190 mg of the title compound was obtained as yellow crystals in the same manner as in Example 49.

m.p.; 200–202° C.

MASS 449 (MH$^+$)

$^1$H-NMR (400 MHz, CDCl$_3$) δ; 3.14(3H, d, J=5.2 Hz), 3.82(3H, s), 4.04(3H, s), 5.16(1H, br s), 7.10(1H, s),7.13 (1H, s), 7.44(1H, m), 7.47–7.53(2H, m), 7.62–7.70(3H, m), 7.75(1H, m), 7.81(1H, m), 7.98(1H, t, J=1.4 Hz), 8.11(1H, t, J=2.0 Hz), 8.85(1H, d, J=2.0 Hz), 8.89(1H, d, J=2.0 Hz).

EXAMPLE 64

6,7-Dimethoxy-4-[3-(8-methyl-3-quinolyl)phenyl]-2-methylaminoquinazoline

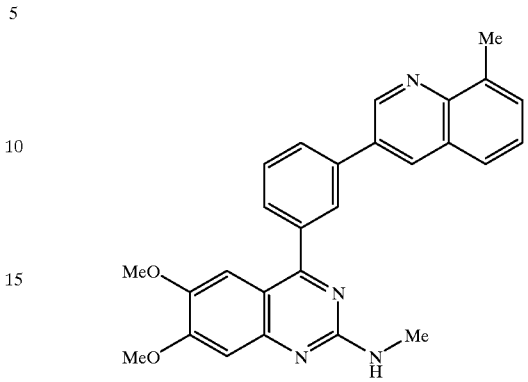

Starting from 250 mg of 4-(3-bromophenyl)-6,7-dimethoxy-2-methylaminoquinazoline obtained in Production Example 8 and 220 mg of 8-methyl-3-quinolyl diethyl borane, 110 mg of the title compound was obtained as yellow crystals in the same manner as in Example 49.

m.p.; 188–190° C.

MASS 437 (MH$^+$)

$^1$H-NMR (400 MHz, CDCl$_3$) δ; 2.86(3H, s), 3.15(3H, d, J=4.8 Hz), 3.83(3H, s), 4.05(3H, s), 5.17(1H, br s), 7.11(1H, s), 7.16(1H, s), 7.48(1H, dd, J=8.0, 7.2 Hz), 7.60(1H, m), 7.68–7.78(3H, m), 7.89(1H, m), 8.07(1H, t, J=1.6 Hz), 8.35(1H, d, J=1.6 Hz), 9.27(1H, d, J=1.6 Hz).

EXAMPLE 65

6,7-Dimethoxy-2-methylamino-4-[3-(2-phenyl ethynyl)phenyl]quinazoline

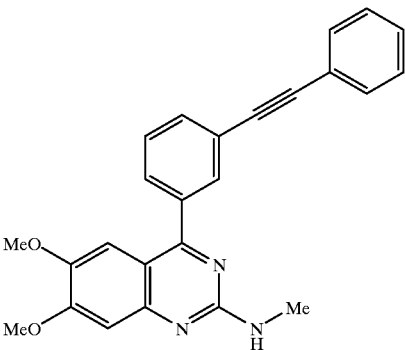

374 mg of 4-(3-bromophenyl)6,7-dimethoxy-2-methylaminoquinazoline obtained in Production Example 8, 153 mg of phenyl acetylene, 70.2 mg of bis(triphenyl phosphine)palladium dichloride, 19.0 mg copper iodide and 202 mg triethylamine were suspended in 10 ml N,N-dimethylformamide and heated under reflux for 6 hours. After ethyl acetate was added thereto, the mixture was washed with water twice and with brine, and then dried over anhydrous magnesium sulfate. The solvent was evaporated, and the crude product was purified and separated by silica gel column chromatography (hexane:ethyl acetate=2:1). The product was recrystallized from hexane-ethanol to give 111 mg of the title compound as pale yellow crystals.

m.p.; 102–104° C.

MASS 396 (MH⁺)

¹H-NMR (400 MHz, CDCl₃) δ; 3.13(3H, d, J=5.0 Hz), 3.83(3H, s), 4.04(3H, s), 5.15(1H, br s), 7.06(1H, s), 7.08 (1H, s), 7.33–7.40(3H, m), 7.50–7.57(3H, m), 7.64(1H, dt, J=7.7, 1.6 Hz), 7.68(1H, dt, J=7.7, 1.6 Hz), 7.87(1H, t, J=1.6 Hz).

EXAMPLE 66

6,7-Dimethoxy-2-methylamino-4-[3-(2-phenylethyl)phenyl]quinazoline

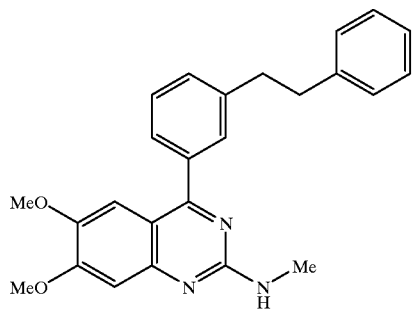

70.0 mg of 6,7-dimethoxy-2-methylamino-4-[3-(2-phenyl ethynyl)phenyl]quinazoline obtained in Example 65, 50.0 mg Lindlar catalyst and 50.0 mg triethylamine were suspended in a mixed solvent of 5 ml ethanol and 5 ml tetrahydrofuran. After the atmosphere was replaced with hydrogen, the mixture was stirred for 6 hours at ordinary pressure at room temperature. The reaction solution was filtered, and the filtrate was evaporated. Then, the crude product was purified and separated by silica gel column chromatography (hexane:ethyl acetate=2:1). The product was recrystallized from hexane-isopropanol to give 45.0 mg of the title compound as colorless crystals.

m.p.; 95–97° C.

MASS 400 (MH⁺)

¹H-NMR (400 MHz, CDCl₃) δ; 2.95–3.06(4H, m), 3.13 (3H, d, J=4.9 Hz), 3.80(3H, s), 4.03(3H, s), 5.17(1H, brs), 7.08(1H, s), 7.09(1H, s), 7.17–7.24(3H, m), 7.25–7.36(3H, m), 7.45(1H, t, J=7.5 Hz), 7.51–7.58 (2H, m).

EXAMPLE 67

6,7-Dimethoxy-2-methylamino-4-[3-[2-(3-pyridyl)ethynyl]phenyl]quinazoline

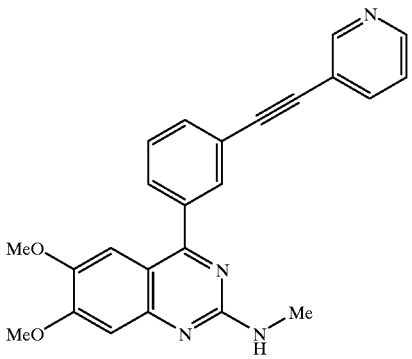

Starting from 374 mg of 4-(3-bromophenyl)-6,7-dimethoxy-2-methylaminoquinazoline obtained in Production Example 8 and 163 mg of 3-pyridylacetylene obtained from 3-bromopyridine, 35 mg of the title compound was obtained as yellow crystals in the same manner as in Example 65.

m.p.; 103–105° C.

MASS 397 (MH⁺)

¹H-NMR (400 MHz, CDCl₃) δ; 3.13(3H, d, J=4.9 Hz), 3.83(3H, s), 4.04(3H, s), 5.17(1H, br s), 7.05(1H, s), 7.09 (1H, s), 7.30(1H, ddd, J=8.0, 5.0, 1.0 Hz), 7.55(1H, t, J=8.0 Hz), 7.66–7.72(2H, m), 7.82(1H, dt, J=8.0, 2,0 Hz), 7.89 (1H, dt, J=2.0 Hz), 8.56(1H, dd, J=5.0, 2.0 Hz), 8.78(1H, dd, J=2.0, 1.0 Hz).

EXAMPLE 68

6,7-Dimethoxy-2-methylamino-4-[3-[2-(6-methylamino-3pyridyl)ethynyl]phenyl]quinazoline

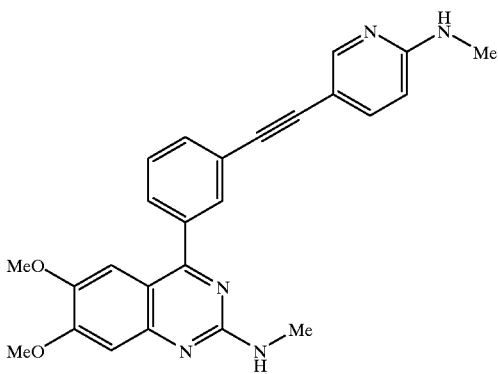

Starting from 250 mg of 4-(3-bromophenyl)-6,7-dimethoxy-2-methylaminoquinazoline obtained in Production Example 8 and 166 mg of 6-methylamino-3-pyridylacetylene obtained from 2,5-dibromopyridine, 68 mg of the title compound was obtained as pale yellow crystals in the same manner as in Example 65.

m.p.; 136–138° C.

MASS 426 (MH⁺)

¹H-NMR (400 MHz, CDCl₃) δ; 2.95(3H, d, J=5.1 Hz), 3.13(3H, d, J=4.9 Hz), 3.82(3H, s), 4.03(3H, s), 4.74(1H, br s), 5.15(1H, br s), 6.36(1H, dd, J=8.6, 2.0 Hz), 7.06(1H, s), 7.08(1H, s), 7.50(1H, t, J=7.8 Hz), 7.56(1H, dd, J=8.6, 2.0 Hz), 7.60–7.66(2H, m), 7.83(1H, t, J=1.6 Hz), 8.29(1H, d, J=2.0 Hz).

EXAMPLE 69

6,7-Dimethoxy-2-methylamino-4-[3-(2-phenylethenyl)phenyl]quinazoline

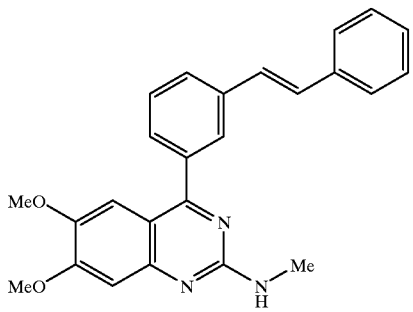

6,7-Dimethoxy-4-(3-formylphenyl)-2-methylaminoquinazoline (323 mg) obtained in Production Example 18 was subjected in a usual manner to Wittig-Horner reaction with diethyl benzyl phosphonate to give 145 mg of the title compound was obtained as pale yellow crystals.

m.p.; 110–112° C.

MASS 398 (MH$^+$)

$^1$H-NMR (400 MHz, CDCl$_3$) δ; 3.14(3H, d, J=4.9 Hz), 3.81(3H, s), 4.04(3H, s), 5.17(1H, br s), 7.09(1H, s), 7.11 (1H, s), 7.19(2H, s), 7.28(1H, m), 7.34–7.40(2H, m), 7.50–7.60(4H, m), 7.66(1H, dt, J=7.5, 1.5 Hz), 7.85(1H, t, J=1.5 Hz).

EXAMPLE 70

6,7-Dimethoxy-2-methylamino-4-(3-phenylcarbamoylphenyl)quinazoline

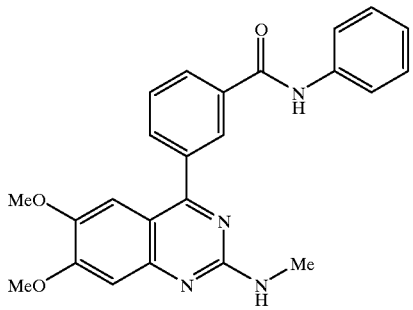

2-Chloro-4-(3-chloroformylphenyl)-6,7-dimethoxyquinazoline (310 mg) obtained in Production Example 17 was reacted with aniline in a conventional manner, and then treated in the same manner as in Example 46 to give 226 mg of the title compound as pale yellow crystals.

m.p.; 242–244° C.

MASS 415 (MH$^+$)

$^1$H-NMR (400 MHz, CDCl$_3$) δ; 3.13(3H, d, J=4.8 Hz), 3.81(3H, s), 4.03(3H, s), 5.16(1H, br s), 7.00(1H, s), 7.08 (1H, s), 7.17(1H, m), 7.36–7.42(2H, m), 7.64–7.70(3H, m), 7.87(1H, m), 7.98(1H, br s), 8.04(1H, m), 8.19(1H, t, J=1.6 Hz).

EXAMPLE 71

6,7-Dimethoxy-2-methylamino-4-[3-(3-pyridyl)carbamoylphenyl]quinazoline

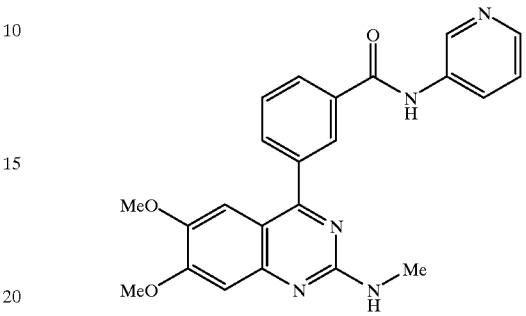

2-Chloro-4-(3-chloroformylphenyl)-6,7-dimethoxyquinazoline (310 mg) obtained in Production Example 17 was reacted with 3-aminopyridine in a conventional manner, and then treated in the same manner as in Example 46 to give 182 mg of the title compound as pale yellow crystals.

m.p.; 238–240° C.

MASS 416 (MH$^+$)

$^1$H-NMR (400 MHz, CDCl$_3$) δ; 3.13(3H, d, J=5.2 Hz), 3.79(3H, s), 4.02(3H, s), 5.17(1H, br s), 6.97(1H, s), 7.06 (1H, s), 7.34(1H, dd, J=8.4, 4.4 Hz), 7.68(1H, t, J=8.0 Hz), 7.88(1H, m), 8.08(1H, m), 8.20–8.26(2H, m), 8.33(1H, m), 8.41(1H, dd, J=4.4, 2.0 Hz), 8.72(1H, d, J=2.0 Hz).

EXAMPLE 72

4-(3-Benzyloxyphenyl)-6,7-dimethoxy-2-methylaminoquinazoline

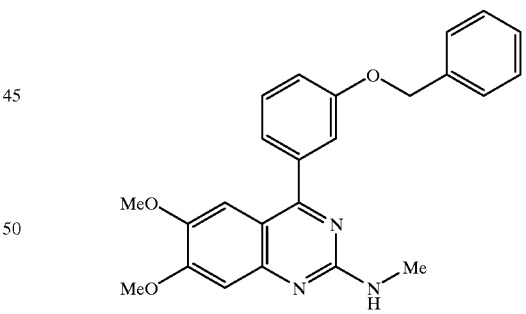

Starting from 500 mg of 2-chloro-6,7-dimethoxy-4-(3-benzyloxyphenyl)quinazoline obtained from 3,4-dichloro-6,7-dimethoxyquinazoline and 3-benzyloxyphenyl boric acid in the same manner as in Production Example 1, 391 mg of the title compound was obtained as pale yellow crystals in the same manner as in Example 46.

m.p.; 116–118° C.

MASS 402 (MH$^+$)

$^1$H-NMR (400 MHz, CDCl$_3$) δ; 3.12(3H, d, J=4.8 Hz), 3.78(3H, s), 4.03(3H, s), 5.13(2H, s), 7.07(1H, s), 7.09(1H, s), 7.13(1H, dd, J=6.8, 0.8 Hz), 7.27(1H, m), 7.31–7.46(7H, m).

EXAMPLE 73

6,7-Dimethoxy-2-methylamino-4-(3-phenoxylphenyl)quinazoline

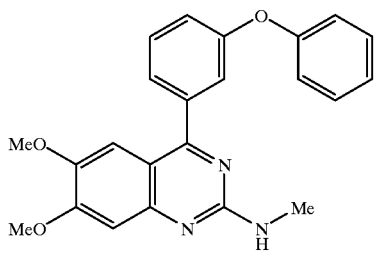

Starting from 250 mg of 2-chloro-6,7-dimethoxy-4-(3-phenoxyphenyl)quinazoline obtained from 3,4-dichloro-6,7-dimethoxyquinazoline and 3-phenoxyphenyl boric acid in the same manner as in Production Example 1, 146 mg of the title compound was obtained as yellow crystals in the same manner as in Example 46.

m.p.; 157–159° C.

MASS 388 (MH$^+$)

$^1$H-NMR (400 MHz, CDCl$_3$) δ; 3.11(3H, d, J=4.8 Hz), 3.79(3H, s), 4.02(3H, s), 4.12(1H, br s), 7.05(1H, s), 7.06 (1H, s), 7.08(2H, m), 7.12(1H, m), 7.17(1H, m), 7.32–7.37 (3H, m), 7.43(1H, dt, J=7.6, 1.2 Hz), 7.50(1H, t, J=7.6 Hz).

EXAMPLE 74

6,7-Dimethoxy-2-methylamino-4-(5-phenyl-2=thienyl)quinazoline

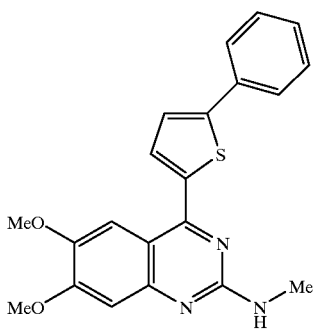

Starting from 286 mg of 2-chloro-6,7-dimethoxy-4-(5-phenyl-2-thienyl)quinazoline obtained from 3,4-dichloro-6,7-dimethoxyquinazoline and 5-phenyl-2-thienylboric acid in the same manner as in Production Example 1, 180 mg of the title compound was obtained as yellow crystals in the same manner as in Example 46.

m.p.; 201–203° C.

MASS 378 (MH$^+$)

$^1$H-NMR (400 MHz, CDCl$_3$) δ; 3.13(3H, d, J=5.0 Hz), 3.97(3H, s), 4.03(3H, s), 5.09(1H, br s), 7.05(1H, s), 7.35 (1H, m), 7.40–7.46(3H, m), 7.58(1H, s), 7.68–7.74(3H, m).

EXAMPLE 75

6,7-Dimethoxy-2-methylamino-4-(5-phenyl-3-pyridyl)quinazoline

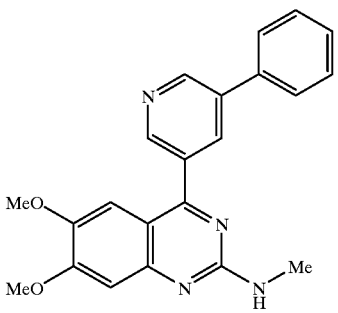

Starting from 445 mg of 2-chloro-6,7-dimethoxy-4-(5-phenyl-3-pyridyl)quinazoline obtained from 3,4-dichloro-6,7-dimethoxyquinazoline and 5-phenyl-3-pyridylboric acid in the same manner as in Production Example 1, 220 mg of the title compound was obtained as pale yellow crystals in the same manner as in Example 46.

m.p.; 177–179° C.

MASS 373 (MH$^+$)

1H-NMR (400 MHz, CDCl$_3$) δ; 3.11(3H, d, J=4.9 Hz), 3.84(3H, s), 4.05(3H, s), 5.16(1H, br s), 7.07(H, s), 7.10(1H, s), 7.45(1H, m), 7.49–7.54(2H, m), 7.65–7.69(2H, m), 8.24 (1H, t, J=2.0 Hz), 8.93(1H, d, J=2.0 Hz), 9.00(1H, d, J=2.0 Hz).

EXAMPLE 76

4-(5-Bromo-3-pyridyl)-6,7-dimethoxy-2-methylaminoquinazoline

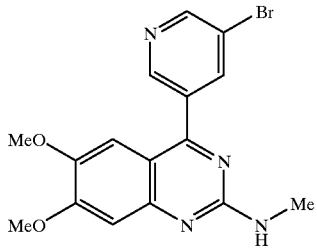

Starting from 2.40 g of 2-chloro-6,7-dimethoxy-4-(5-bromo-3-pyridyl)quinazoline obtained from 3,4-dichloro-6,7-dimethoxyquinazoline and 5-bromo-3-pyridylboric acid in the same manner as in Production Example 1, 1.46 g of the title compound was obtained as pale yellow crystals in the same manner as in Example 46.

m.p.; 228–230° C.

MASS 375, 377 (MH$^+$)

$^1$H-NMR (400 MHz, CDCl$_3$) δ; 3.12(3H, d, J=5.0 Hz), 3.85(3H, s), 4.04(3H, s), 5.15(1H, br s), 6.96(1H,s 5), 7.07(1H, s), 8.21(1H, t, J=2.0 Hz), 8.83(1H, d, J=2.0 Hz), 8.88(1H, d, J=2.0 Hz).

EXAMPLE 77

6,7-Dimethoxy-2-methylamino-4-[5-(4-methylthiophenyl)-3-pyridyl]quinazoline

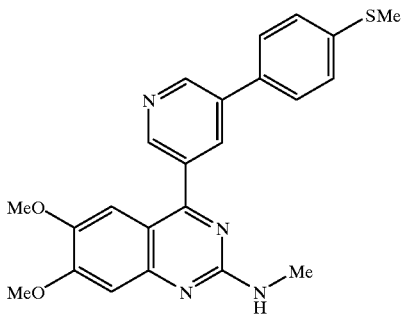

Starting from 375 mg of 4-(5-bromo-3pyridyl)-6,7-dimethoxy-2-methylaminoquinazoline obtained in Example 76 and 225 mg of 4-methylthiophenylboric acid, 440 mg of the title compound was obtained as pale yellow crystals in the same manner as in Example 48.

m.p.; 170–172° C.
MASS 419 (MH+)
$^1$H-NMR (400 MHz, CDCl$_3$) δ; 2.54(3H, s), 3.13(3H, d, J=5.0 Hz), 3.84(3H, s), 4.04(3H, s), 5.18(1H, br s), 7.06(1H, s), 7.10(1H, s), 7.35–7.40(2H, m), 7.57–7.62(2H, m), 8.21 (1H, t, J=2.0 Hz), 8.91(1H, d, J=2.0 Hz), 8.97(1H, d, J=2.0 Hz).

EXAMPLE 78

6,7-Dimethoxy-2-methylamino-4-[5-[2-(3-pyridyl)ethynyl]-3-pyridyl]quinazoline

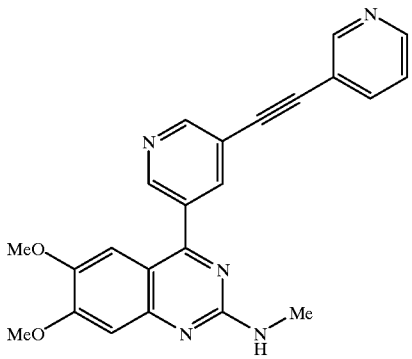

Starting from 250 mg of 4-(5-bromo-3-pyridyl)-6,7-dimethoxy-2-methylaminoquinazoline obtained in Example 76 and 195 mg of 3-pyridylacetylene obtained from 3-bromopyridine, 184 mg of the title compound was obtained as yellow crystals in the same manner as in Example 71.

m.p.; 208–211° C.
MASS 398 (MH+)
$^1$H-NMR (400 MHz, CDCl$_3$) δ; 3.13(3H, d, J=5.0 Hz), 3.85(3H, s), 4.05(3H, s), 5.17(1H, br s), 6.99(1H, s), 7.09 (1H, s), 7.33(1H, ddd, J=8.0, 5.0, 1.0 Hz), 7.85(1H, dt, J=8.0, 2.0 Hz), 8.20(1H, t, J=2.0 Hz), 8.61(1H, dd, J=5.0, 2.0 Hz), 8.81(1H, dd, J=2.0, 1.0 Hz), 8.91(2H, d, J=2.0 Hz).

EXAMPLE 79

6,7-Dimethoxy-2-methylamino-4-[5-[2-(6-methylamino-3-pyridyl)ethynyl]-3-pyridyl]quinzoline

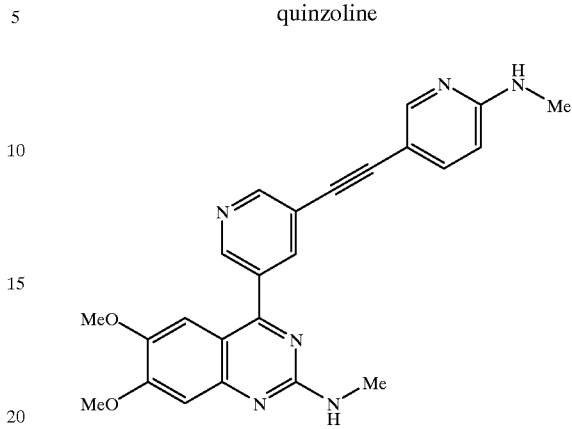

Starting from 250 mg of 4-(5-bromo-3-pyridyl)-6,7-dimethoxy-2-methylaminoquinazoline obtained in Example 76 and 166 mg of 6-methylamino-3-pyridylacetylene obtained from 2,5-dibromopyridine, 215 mg of the title compound was obtained as yellow crystals in the same manner as in Example 65.

m.p.; 160–162° C.
MASS 427 (MH+)
$^1$H-NMR (400 MHz, CDCl$_3$) δ; 2.97(3H, d, J=5.4 Hz), 3.13(3H, d, J=4.9 Hz), 3.85(3H, s), 4.04(3H, s), 4.82(1H, br s), 5.17(1H, br s), 6.38(1H, dd, J=8.6, 0.6 Hz), 6.99(1H, s), 7.09(1H, s), 7.58(1H, dd, J=8.6, 2.2 Hz), 8.12(1H, t, J=2.0 Hz), 8.31(1H, dd, J=2.2, 0.6 Hz), 8.83(1H, d, J=2.0 Hz), 8.85(1H, d, J=2.0 Hz).

EXAMPLE 80

4-(3-Aminophenyl)-6-benzyloxy-7-methoxy-2-methylaminoquinazoline

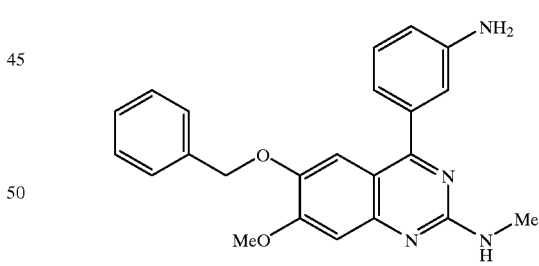

Starting from 289 mg of 4-(3-aminophenyl)-6-benzyloxy-2-chloro-7-methoxyquinazoline obtained from 6-benzyloxy-2,4-dichloro-7-methoxyquinazoline obtained in Production Example 19 and 3-aminophenyl boric acid in the same manner as in Production Example 1, 295 mg of the title compound was obtained as yellow crystals in the same manner as in Example 46.

MASS 387 (MH+)
$^1$H-NMR (400 MHz, CDCl$_3$) δ; 3.10(3H, d, J=5.0 Hz) 3.72(2H, m), 4.03(3H, s), 5.06–5.14(3H, m), 6.78–6.84(3H, m), 7.06(1H, s), 7.14(1H, s), 7.21(1H, t, J=7.8 Hz), 7.28–7.40(5H, m).

EXAMPLE 81

4-(3-Benzoylaminophenyl)-6-benzyloxy-7-methoxy-2-methylaminoquinazoline

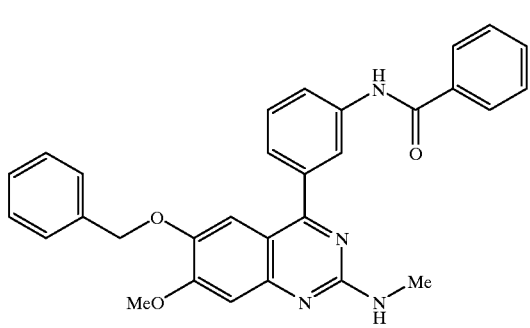

4-(3-Aminophenyl)-6-benzyloxy-7-methoxy-2-methylaminoquinazoline (248 mg) obtained in Example 80 was benzoylated in a conventional manner to give 298 mg of the title compound as pale yellow crystals.

m.p.; 204–206° C.

MASS 491 (MH$^+$)

$^1$H-NMR (400 MHz, CDCl$_3$) δ; 3.13(3H, d, J=5.0 Hz), 4.04(3H, s), 5.11(1H, br s), 5.15(2H, s), 7.08(1H, s), 7.18 (1H, s), 7.20–7.25 (2H, m), 7.29–7.34(2H, m), 7.36–7.41 (2H, m), 7.43–7.61 (4H, m), 7.78(1H, m), 7.85–7.93(4H, m).

EXAMPLE 82

4-(3-Benzoylaminophenyl)-6-hydroxy-7-methoxy-2-methylaminoquinazoline

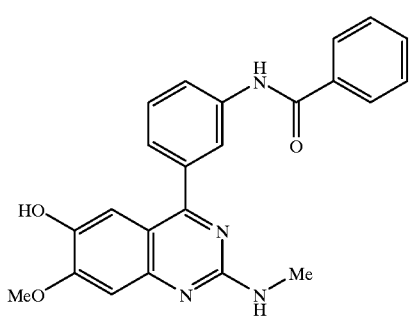

4-(3-Benzoylaminophenyl)-6-benzyloxy-7-methoxy-2-methylaminoquinazoline (245 mg) obtained in Example 81 was catalytically reduced in a conventional manner to give 166 mg of the title compound as pale yellow crystals.

m.p.; 145–147° C.

MASS 401 (MH$^+$)

$^1$H-NMR (400 MHz, CDCl$_3$) δ; 3.09(3H, d, J=5.1 Hz), 4.01(3H, s), 5.18(1H, br s), 7.06(1H, s), 7.24(1H, s), 7.39 (1H, m), 7.42–7.50(3H, m), 7.54(1H, m), 7.82–7.92(4H, m), 8.11(1H, br s).

EXAMPLE 83

2-Amino-4-(3-biphenylyl)-6,7-dimethoxyquinoline

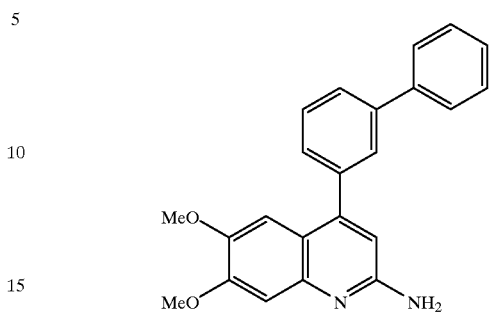

Starting from 180 mg of 2-amino-4-(3-bromophenyl)-6,7-dimethoxyquinoline obtained in Production Example 20 and 91.4 mg of phenyl boric acid, 168 mg of the title compound was obtained as a pale yellow oil in the same manner as in Example 48.

MASS 357 (MH$^+$)

$^1$H-NMR (400 MHz, CDCl$_3$) δ; 3.79(3H, s), 4.01(3H, s), 4.60(2H, m), 6.61(1H, s), 7.08(1H, s), 7.16(1H, s), 7.38(1H, m), 7.43–7.50 (3H, m), 7.58(1H, t, J=7.6 Hz), 7.62–7.67(2H, m), 7.69–7.74(2H, m).

EXAMPLE 84

2-Amino-6,7-dimethoxy-4-[3-(3-pyridyl)phenyl]quinoline

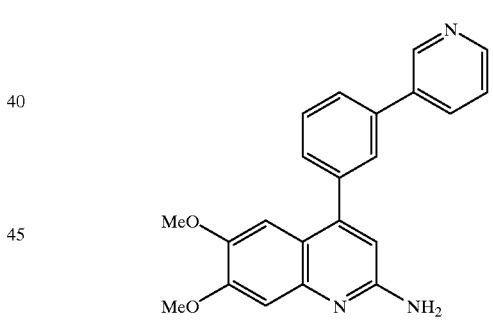

Starting from 180 mg of 2-amino-4-(3-bromophenyl)-6,7-dimethoxyquinoline obtained in Production Example 20 and 92 mg of 3-pyridyl boric acid, 95 mg of the title compound was obtained as a pale yellow oil in the same manner as in Example 48.

MASS 358 (MH$^+$)

$^1$H-NMR (400 MHz, CDCl$_3$) δ; 3.79(3H, s), 4.01(3H, s), 4.61(2H, m), 6.61(1H, s), 7.03(1H, s), 7.17(1H, s), 7.39(1H, m), 7.54(1H, m), 7.63(1H, t, J=7.6 Hz), 7.68–7.72(2H, m), 7.93(1H, m), 7.92–7.95 (2H, m), 8.62(1H, dd, J=4.8, 2.0 Hz), 8.92(1H, dd, J=2.0, 0.8 Hz).

We claim:

1. A nitrogen-containing heterocyclic compound represented by the following formula, its pharmaceutically acceptable salt or hydrates thereof,

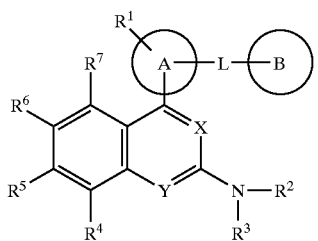

wherein, the ring A is an aromatic hydrocarbon ring, optionally having a heteroatom,
the ring B represents:
1) a saturated hydrocarbon ring, optionally having a substituent group,
2) an unsaturated hydrocarbon ring, optionally having a substituent group,
3) a saturated heterocyclic ring optionally having a substituent group, or
4) an unsaturated heterocyclic ring, optionally having a substituent group,
$R^1$ represents:
1) a hydrogen atom,
2) a halogen atom,
3) a $C_{1-6}$ alkyl group optionally substituted with a halogen atom,
4) a $C_{1-6}$ alkoxy group optionally substituted with a halogen atom, or
5) an amino group, optionally substituted with a $C_{1-6}$ alkyl group or an acyl group,
$R^2$ and $R^3$ are the same as or different from each other and each represents:
1) a hydrogen atom,
2) a $C_{1-6}$ alkyl group, optionally having a substituent group,
3) a $C_{3-7}$ cycloalkyl group, optionally having a substituent group,
4) a $C_{2-6}$ alkenyl group optionally having a substituent group, or
5) an acyl group,
$R^4$, $R^5$, $R^6$ and $R^7$ are the same as or different from each other and each represents:
1) a hydrogen atom,
2) a halogen atom,
3) a $C_{1-6}$ alkyl group, optionally substituted with a halogen atom,
4) a $C_{3-7}$ cycloalkyl group, optionally having a substituent group,
5) an aryl group, optionally having a substituent group,
6) a $C_{1-6}$ alkoxy group, optionally having a substituent group,
7) a $C_{3-7}$ cycloalkoxy group, optionally having a substituent group,
8) an aryl alkoxy group, optionally having a substituent group,
9) a $C_{1-6}$ alkyl thio group optionally having a substituent group,
10) a hydroxyl group,
11) an amino group, optionally substituted with a $C_{1-6}$ alkyl group or an acyl group,
12) a nitro group,
13) a cyano group,
14) a carboxyl group, or
15) a $C_{1-6}$ alkoxy carbonyl group, L represents:
1) a $C_{1-6}$ alkylene group, optionally having a substituent group,
2) a $C_{2-6}$ alkenylene group, optionally having a substituent group,
3) a $C_{2-6}$ alkynylene group optionally having a substituent group, or
4) a group represented by the formula —E—G—,
wherein E represents:
a) an oxygen atom,
b) a sulfur atom,
c) formula —CO—,
d) —SO—,
e) —SO$_2$—,
f) —N($R^8$)— (wherein $R^8$ represents a hydrogen atom, a $C_{1-6}$ alkyl group or an acyl group),
g) —N($R^9$)—CO— (wherein $R^9$ represents a hydrogen atom or a $C_{1-6}$ alkyl group), or
h) —(CH$_2$)$_m$— (wherein m is an integer of 0 to 6) optionally having a substituent group; and
G represents:
a) a sulfonyl group,
b) formula —N($R^{10}$)—, wherein $R^{10}$ represents a hydrogen atom, a $C_{1-6}$ alkyl group or an acyl group or
c) —(CH$_2$)$_n$—, wherein n is an integer of 0 to 6, and X and Y are the same or different from each other and each represents:
1) a nitrogen atom,
2) =CH— or
3) a carbon atom optionally substituted with a $C_{1-6}$ alkyl group optionally having a substituent group,
wherein X and Y are not simultaneously a carbon atom optionally substituted with a $C_{1-3}$ alkyl group, X and Y are not simultaneously =CH—, and X and Y are not simultaneously a nitrogen atom.

2. A nitrogen-containing heterocyclic compound represented by the following formula, its pharmaceutically acceptable salt or hydrates thereof,

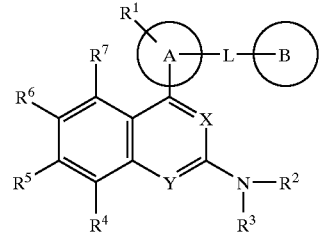

wherein, the ring A is a benzene ring, a naphthalene ring, a pyridine ring or a thiophene ring,
the ring B represents:
1) a saturated hydrocarbon ring, optionally having a substituent group,
2) an unsaturated hydrocarbon ring, optionally having a substituent group,
3) a saturated heterocyclic ring optionally having a substituent group, or
4) an unsaturated heterocyclic ring, optionally having a substituent group,
$R^1$ represents:
1) a hydrogen atom,
2) a halogen atom,
3) a $C_{1-6}$ alkyl group optionally substituted with a halogen atom,
4) a $C_{1-6}$ alkoxy group optionally substituted with a halogen atom, or 5) an amino group, optionally substituted with a $C_{1-6}$ alkyl group or an acyl group, $R^2$ and $R^3$ are the same as or different from each other and each represents:
1) a hydrogen atom,
2) a $C_{1-6}$ alkyl group, optionally having a substituent group,
3) a $C_{3-7}$ cycloalkyl group, optionally having a substituent group,
4) a $C_{2-6}$ alkenyl group optionally having a substituent group, or
5) an acyl group, $R^4$, $R^5$, $R^6$ and $R^7$ are the same as or different from each other and each represents:
1) a hydrogen atom,
2) a halogen atom,
3) a $C_{1-6}$ alkyl group, optionally substituted with a halogen atom,
4) a $C_{3-7}$ cycloalkyl group, optionally having a substituent group,
5) an aryl group, optionally having a substituent group,
6) a $C_{1-6}$ alkoxy group, optionally having a substituent group,
7) a $C_{3-7}$ cycloalkoxy group, optionally having a substituent group,
8) an aryl alkoxy group, optionally having a substituent group,
9) a $C_{1-6}$ alkyl thio group optionally having a substituent group,
10) a hydroxyl group,
11) an amino group, optionally substituted with a $C_{1-6}$ alkyl group or an acyl group,
12) a nitro group,
13) a cyano group,
14) a carboxyl group, or
15) a $C_{1-6}$ alkoxy carbonyl group, L represents:
1) a single bond,
2) a $C_{1-6}$ alkylene group, optionally having a substituent group,
3) a $C_{2-6}$ alkenylene group, optionally having a substituent group,
4) a $C_{2-6}$ alkynylene group optionally having a substituent group, or
5) a group represented by the formula —E—G—, wherein E represents:
  a) an oxygen atom,
  b) a sulfur atom,
  C) formula —CO—,
  d) —SO—,
  e) —SO$_2$—,
  f) —N($R^8$)— (wherein $R^8$ represents a hydrogen atom, a $C_{1-6}$ alkyl group or an acyl group),
  g) —N($R^9$)—CO— (wherein $R^9$ represents a hydrogen atom or a $C_{1-6}$ alkyl group), or
  h) —CH$_2$)$_m$— (wherein m is an integer of 0 to 6) optionally having a substituent group; and
G represents:
  a) a sulfonyl group,
  b) formula —N($R^{10}$)—, wherein $R^{10}$ represents a hydrogen atom, a $C_{1-6}$ alkyl group or an acyl group or
  c) —(CH$_2$)$_n$—, wherein n is an integer of 0 to 6, and X and Y are the same or different from each other and each represents:
1) a nitrogen atom,
2) =CH— or
3) a carbon atom optionally substituted with a $C_{1-6}$ alkyl group optionally having a substituent group, wherein X and Y are not simultaneously a carbon atom optionally substituted with a $C_{1-3}$ alkyl group, X and Y are not simultaneously =CH—, and X and Y are not simultaneously a nitrogen atom.

3. A nitrogen-containing heterocyclic compound, its pharmaceutically acceptable salt or hydrates thereof,

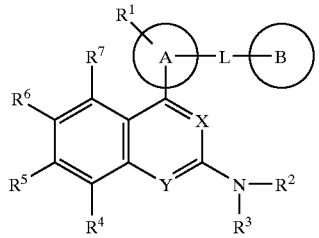

wherein, the ring A is an aromatic hydrocarbon ring, optionally having a heteroatom, the ring B represents a benzene ring having a substituent group, a naphthalene ring optionally having a substituent group, a pyridine ring optionally having a substituent group, a pyrrole ring optionally having a substituent group, a quinoline ring optionally having a substituent group, an imidazopyridine ring optionally having a substituent group, an isoindole ring, a phthalimide ring or a benzene ring substituted with an alkylene dioxy group, $R^1$ represents:
1) a hydrogen atom,
2) a halogen atom,
3) a $C_{1-6}$ alkyl group optionally substituted with a halogen atom,
4) a $C_{1-6}$ alkoxy group optionally substituted with a halogen atom, or
5) an amino group, optionally substituted with a $C_{1-6}$ alkyl group or an acyl group, $R^2$ and $R^3$ are the same as or different from each other and each represents:
1) a hydrogen atom,
2) a $C_{1-6}$ alkyl group, optionally having a substituent group,
3) a $C_{3-7}$ cycloalkyl group, optionally having a substituent group,
4) a $C_{2-6}$ alkenyl group optionally having a substituent group, or
5) an acyl group, $R^4$, $R^5$, $R^6$ and $R^7$ are the same as or different from each other and each represents:
1) a hydrogen atom,
2) a halogen atom,
3) a $C_{1-6}$ alkyl group, optionally substituted with a halogen atom,
4) a $C_{3-7}$ cycloalkyl group, optionally having a substituent group,
5) an aryl group, optionally having a substituent group,
6) a $C_{1-6}$ alkoxy group, optionally having a substituent group,
7) a $C_{3-7}$ cycloalkoxy group, optionally having a substituent group,
8) an aryl alkoxy group, optionally having a substituent group,
9) a $C_{1-6}$ alkyl thio group optionally having a substituent group, 10) a hydroxyl group,
11) an amino group, optionally substituted with a $C_{1-6}$ alkyl group or an acyl group,
12) a nitro group,
13) a cyano group,
14) a carboxyl group, or
15) a $C_{1-6}$ alkoxy carbonyl group, L represents:
1) a single bond,
2) a $C_{1-6}$ alkylene group, optionally having a substituent group,
3) a $C_{2-6}$ alkenylene group, optionally having a substituent group,
4) a $C_{2-6}$ alkynylene group optionally having a substituent group, or
5) a group represented by the formula —E—G—, wherein E represents:
   a) an oxygen atom,
   b) a sulfur atom,
   c) formula —CO—,
   d) —SO—,
   e) —SO$_2$—,
   f) —N(R$^8$)— (wherein R$^8$ represents a hydrogen atom, a $C_{1-6}$ alkyl group or an acyl group),
   g) —N(R$^9$)—CO— (wherein R$^9$ represents a hydrogen atom or a $C_{1-6}$ alkyl group), or
   h) —(CH$_2$)$_m$— (wherein m is an integer of 0 to 6) optionally having a substituent group; and
G represents:
   a) a sulfonyl group,
   b) formula —N(R$^{10}$)—, wherein R$^{10}$ represents a hydrogen atom, a $C_{1-6}$ alkyl group or an acyl group or
   c) —(CH$_2$)$_n$—, wherein n is an integer of 0 to 6, and X and Y are the same or different from each other and each represents:
1) a nitrogen atom,
2) =CH— or
3) a carbon atom optionally substituted with a $C_{1-6}$ alkyl group optionally having a substituent group, wherein X and Y are not simultaneously a carbon atom optionally substituted with a $C_{1-3}$ alkyl group, X and Y are not simultaneously =CH—, and X and Y are not simultaneously a nitrogen atom.

4. The nitrogen-containing heterocyclic compound as claimed in claim 1 or 2, its pharmaceutically acceptable salt or hydrates thereof, in which the ring B is a $C_{3-7}$ hydrocarbon ring optionally having a substituent group, a benzene ring optionally having a substituent group, a naphthalene ring optionally having a substituent group, a pyridine ring optionally having a substituent group, a pyrrole ring optionally having a substituent group, a quinoline ring optionally having a substituent group, an imidazopyridine ring optionally having a substituent group, an isoindole ring, a phthalimide ring or a benzene ring optionally substituted with an alkylene dioxy group.

5. The nitrogen-containing heterocyclic compound as claimed in claim 1 or 3, its pharmaceutically acceptable salt or hydrates thereof, in which the ring A is a benzene ring optionally having a substituent group.

6. The nitrogen-containing heterocyclic compound as claimed in claim 1, 2 or 3, its pharmaceutically acceptable salt or hydrates thereof, in which R$^1$ is a hydrogen atom.

7. The nitrogen-containing heterocyclic compound as claimed in claim 1, 2 or 3, its pharmaceutically acceptable salt or hydrates thereof, in which R$^2$ and R$^3$ are the same or different from each other and each represents a $C_{1-6}$ alkyl group optionally substituted with a halogen atom.

8. The nitrogen-containing heterocyclic compound as claimed in claim 1, 2 or 3, its pharmaceutically acceptable salt or hydrates thereof, in which R$^2$ is methyl group or ethyl group, and R$^3$ is hydrogen atom.

9. The nitrogen-containing heterocyclic compound as claimed in claim 1, 2 or 3, its pharmaceutically acceptable salt or hydrates thereof, in which R$^4$, R$^5$, R$^6$ and R$^7$ are the same or different and represent a hydrogen atom, a hydroxyl group, a $C_{1-6}$ alkoxy group optionally having a substituent group, a $C_{3-7}$ cycloalkyl, group optionally having a substituent group or an aryl alkoxy group optionally having a substituent group.

10. The nitrogen-containing heterocyclic compound as claimed in claim 1, 2 or 3, its pharmaceutically acceptable salt or hydrates thereof, in which both R$^4$ and R$^7$ are hydrogen atoms, R$^5$ and R$^6$ are the same or different and represent a methoxy group, ethoxy group, hydroxyl group or benzyloxy group optionally substituted with a halogen atom.

11. The nitrogen-containing heterocyclic compound as claimed in claim 2 or 3, its pharmaceutically acceptable salt or hydrates thereof, in which L is a single bond.

12. The nitrogen-containing heterocyclic compound as claimed in claim 1, 2 or 3, its pharmaceutically acceptable salt or hydrates thereof, in which L is a $C_{1-6}$ alkylene chain optionally having a substituent group, a $C_{2-6}$ alkenylene chain optionally having a substituent group or a $C_{2-6}$ alkynylene chain optionally having a substituent group.

13. The nitrogen-containing heterocyclic compound as claimed in claim 1, 2 or 3, its pharmaceutically acceptable salt or hydrates thereof, in which L is a group represented by —N(R$^9$)—CO—(CH$_2$)$_n$— wherein R$^9$ represents a hydrogen atom or a $C_{1-6}$ alkyl group and n is an integer of 0 to 6.

14. The nitrogen-containing heterocyclic compound as claimed in claim 1, 2 or 3, its pharmaceutically acceptable salt or hydrates thereof, in which L is a group represented by the formula —N(R$^8$)—(CH$_2$)$_n$— wherein R$^8$ represents a hydrogen atom, a $C_{1-6}$ alkyl group or an acyl group and n is an integer of 0 to 6.

15. The nitrogen-containing heterocyclic compound as claimed in claim 1, 2 or 3, its pharmaceutically acceptable salt or hydrates thereof, in which L is —CH$_2$—, —(CH$_2$)$_2$—, —(CH$_2$)$_3$—, —CH=CH— or —C≡C—.

16. The nitrogen-containing heterocyclic compound as claimed in claim 1, 2 or 3, its pharmaceutically acceptable salt or hydrates thereof, in which L is the formula —NH—CO—, —N(CH$_3$)—CO—, —CO—NH—, —NH—SO$_2$— or —NH—CO—NH—.

17. A pharmaceutical composition, comprising:
a pharmacologically effective amount of the nitrogen-containing heterocyclic compound as claimed in claim 1, 2 or 3, its salt or hydrates thereof, and
a pharmaceutically acceptable carrier.

18. A method of treating a disease against which an inhibitory action on phosphodiesterase-4 is effective for therapy, comprising the step of:
administering a pharmacologically effective amount of the nitrogen-containing heterocyclic compound as claimed in claim 1, 2 or 3, its salt or hydrates thereof to a patient for whom an inhibitory action on phosphodiesterase-4 is effective for therapy.

19. The method of claim 18, wherein the disease is an inflammatory disease.

20. The method of claim 18, wherein the disease is arthritis.

21. The method of claim 18, wherein the disease is diabetes.

22. The method of claim 18, wherein the disease is asthma.

23. The method of claim 18, wherein the disease is an autoimmune disease.

24. The method of claim 18, wherein the disease is allograft rejection.

25. The method of claim 18, wherein the disease is graft versus host disease.

26. The method of claim 18, wherein the disease is chronic joint rheumatism.

27. The method of claim 18, wherein the disease is multiple sclerosis.

28. The method of claim 18, wherein the disease is sepsis.

29. The method of claim 18, wherein the disease is psoriasis.

30. The method of claim 18, wherein the disease is osteoporosis.

31. The nitrogen-containing heterocyclic compound, its pharmaceutically acceptable salt or hydrates thereof of claim 2, wherein said $R^2$ represents a $C_{1-6}$ alkyl group optionally having a substituent group.

32. The nitrogen-containing heterocyclic compound, its pharmaceutically acceptable salt or hydrates thereof of claim 2, wherein said $R^3$ represents a $C_{1-6}$ alkyl group optionally having a substituent group.

33. A nitrogen-containing heterocyclic compound, its pharmaceutically acceptable salt or hydrates thereof,

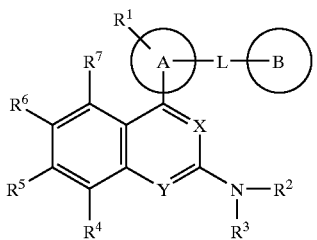

wherein the ring A is an aromatic hydrocarbon ring, optionally having a heteroatom, the ring B represents a $C_{3-7}$ hydrocarbon ring optionally having a substituent group, an aromatic ring optionally having a substituent group or an aromatic heterocyclic ring optionally having a substituent group, $R^1$ represents:
1) a hydrogen atom,
2) a halogen atom,
3) a $C_{1-6}$ alkyl group optionally substituted with a halogen atom,
4) a $C_{1-6}$ alkoxy group optionally substituted with a halogen atom, or
5) an amino group, optionally substituted with a $C_{1-6}$ alkyl group or an acyl group, $R^2$ and $R^3$ are the same as or different from each other and each represents:
1) a hydrogen atom,
2) a $C_{1-6}$ alkyl group, optionally having a substituent group,
3) a $C_{3-7}$ cycloalkyl group, optionally having a substituent group,
4) a $C_{2-6}$ alkenyl group optionally having a substituent group, or
5) an acyl group, each of $R^4$, $R^5$, $R^6$ and $R^7$ represents:
1) a hydrogen atom,
2) a halogen atom,
3) a $C_{1-6}$ alkyl group, optionally substituted with a halogen atom,
4) a $C_{3-7}$ cycloalkyl group, optionally having a substituent group,
5) an aryl group, optionally having a substituent group,
6) a $C_{1-6}$ alkoxy group, optionally having a substituent group,
7) a $C_{3-7}$ cycloalkoxy group, optionally having a substituent group,
8) an aryl alkoxy group, optionally having a substituent group,
9) a $C_{1-6}$ alkyl thio group optionally having a substituent group,
10) a hydroxyl group,
11) an amino group, optionally substituted with a $C_{1-6}$ alkyl group or an acyl group,
12) a nitro group,
13) a cyano group,
14) a carboxyl group, or
15) a $C_{1-6}$ alkoxy carbonyl group, wherein $R^4$, $R^5$, $R^6$ and $R^7$ are the same as or different from each other and at least one of $R^4$, $R^5$, $R^6$ and $R^7$ is other than a hydrogen atom, L represents:
1) a single bond,
2) a $C_{1-6}$ alkylene group, optionally having a substituent group,
3) a $C_{2-6}$ alkenylene group, optionally having a substituent group,
4) a $C_{2-6}$ alkynylene group optionally having a substituent group, or
5) a group represented by the formula —E—G—,
   wherein E represents:
   a) an oxygen atom,
   b) a sulfur atom,
   c) formula —CO—,
   d) —SO—,
   e) —SO$_2$—,
   f) —N($R^8$)— (wherein $R^8$ represents a hydrogen atom, a $C_{1-6}$ alkyl group or an acyl group),
   g) —N($R^9$)—CO— (wherein $R^9$ represents a hydrogen atom or a $C_{1-6}$ alkyl group), or
   h) —(CH$_2$)$_m$— (wherein m is an integer of 0 to 6) optionally having a substituent group; and
   G represents:
   a) a sulfonyl group,
   b) formula —N($R^{10}$)—, wherein $R^{10}$ represents a hydrogen atom, a $C_{1-6}$ alkyl group or an acyl group or
   c) —(CH$_2$)$_n$—, wherein n is an integer of 0 to 6, and X and Y are the same or different from each other and each represents:
1) a nitrogen atom,
2) =CH— or
3) a carbon atom optionally substituted with a $C_{1-6}$ alkyl group optionally having a substituent group, wherein X and Y are not simultaneously a carbon atom optionally substituted with a $C_{1-3}$ alkyl group, X and Y are not simultaneously =CH—, and X and Y are not simultaneously a nitrogen atom.

* * * * *